(12) United States Patent
Alexander et al.

(10) Patent No.: US 7,888,344 B2
(45) Date of Patent: Feb. 15, 2011

(54) FUSED THIAZOLE DERIVATIVES AS KINASE INHIBITORS

(75) Inventors: Rikki Peter Alexander, Berkshire (GB); Pavandeep Aujla, Berkshire (GB); Mark James Batchelor, Berkshire (GB); Daniel Christopher Brookings, Berkshire (GB); George Martin Buckley, Cambridge (GB); Karen Viviane Lucile Crepy, Berkshire (GB); Claire Louise Kulisa, Berkshire (GB); James Petrie Turner, Berkshire (GB)

(73) Assignee: UCB Pharma S.A., Brussels (BE)

( * ) Notice: Subject to any disclaimer, the term of this patent is extended or adjusted under 35 U.S.C. 154(b) by 423 days.

(21) Appl. No.: 11/912,801

(22) PCT Filed: Apr. 25, 2006

(86) PCT No.: PCT/GB2006/001505

§ 371 (c)(1), (2), (4) Date: Jun. 24, 2008

(87) PCT Pub. No.: WO2006/114606

PCT Pub. Date: Nov. 2, 2006

(65) Prior Publication Data

US 2008/0306060 A1    Dec. 11, 2008

(30) Foreign Application Priority Data

Apr. 26, 2005  (GB) .................................. 0508471.0

(51) Int. Cl.
- *A61K 31/55* (2006.01)
- *A61K 31/535* (2006.01)
- *C07D 498/04* (2006.01)
- *C07D 413/14* (2006.01)

(52) U.S. Cl. .................. 514/212.06; 540/521; 544/133; 514/233.8

(58) Field of Classification Search ................. 540/521; 514/212.06, 233.8; 544/133
See application file for complete search history.

(56) References Cited

PUBLICATIONS

Byrn et al., Solid-State Chemistry of Drugs, Second Edition, 1999, pp. 233-247.*
Voskoglou-Nomikos et al., Clinical Cancer Research, vol. 9, 4227-4239.*
Ptcl.chem.ox.ac.uk/MSDS structure activity relationship; Jaworska, 1-8, 2004.*
Science (1999), vol. 286, 531-537.*
Cancer and Metastasis Reviews (1998), 17(1), 91-106.*
Mandel et al., CNS Drugs, 2003: 17(10); 729-62.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Stepanov, D. E. et al., New Derivatives of 4,5,6,7-tetrahydrobenzothiazol-7-one and 5,6,7,8-tetrahydro-4H-thiazolo [5,4-c] azepin-8-one, Russian Journal of General Chemistry, 2000, vol. 70, No. 5, pp. 784-787.
Gaile, I. et al., Heterocyclic compounds based on diketones. VII. 2-Amino-5, 5-dimethyl-4,5,6,7-tetrahydro-m-benzothiazolone and its derivatives, 1967, vol. 1, pp. 54-59.

* cited by examiner

*Primary Examiner*—Rebecca L Anderson
(74) *Attorney, Agent, or Firm*—McDonnell Boehnen Hulbert & Berghoff LLP

(57) ABSTRACT

A series of 5,6-dihydro-1,3-benzothiazol-7(4H)-one derivatives, and analogues thereof, which are substituted in the 2-position by an optionally substituted morpholin-4-yl moiety, being selective inhibitors of PD kinase enzymes, are accordingly of benefit in medicine, for example in the treatment of inflammatory, autoimmune, cardiovascular, neurodegenerative, metabolic, oncological, nociceptive or ophthalmic conditions.

16 Claims, No Drawings

FUSED THIAZOLE DERIVATIVES AS KINASE INHIBITORS

This is a National Stage of International Application No. PCT/GB2006/001505, filed Apr. 25, 2006.

The present invention relates to the use of a class of fused thiazole derivatives in therapy. More particularly, the invention provides a therapeutic use for a family of 5,6-dihydro-1,3-benzothiazol-7(4H)-one derivatives, and analogues thereof, which are substituted in the 2-position by an optionally substituted morpholin-4-yl moiety. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymaun et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds of use in the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human PI3K enzymes.

The specific compounds 2-(morpholin-4-yl)-5,6-dihydro-1,3-benzothiazol-7(4H)-one, 5,5-dimethyl-2-(morpholin-4-yl)-5,6-dihydro-1,3-benzothiazol-7(4H)-one, 2-(morpholin-4-yl)-5,6,7,8-tetrahydro-4H-[1,3]thiazolo[5,4-c]azepin-4-one and 7,7-dimethyl-2-(morpholin-4-yl)-5,6,7,8-tetrahydro-4H-[1,3]thiazolo[5,4-c]azepin-4-one are disclosed in *Russian Journal of General Chemistry* (translation of *Zhurnzal Obshchei Klzimii*), 2000, 70-[5], 784-787; but no therapeutic utility is ascribed therein to those compounds.

The compounds of use in the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides the use of a compound of formula (I), or a pharmaceutically acceptable salt or solvate thereof:

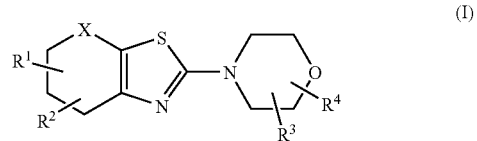

wherein

—X— represents a group of formula (a), (b), (c), (d), (e), (f), (g) or (h):

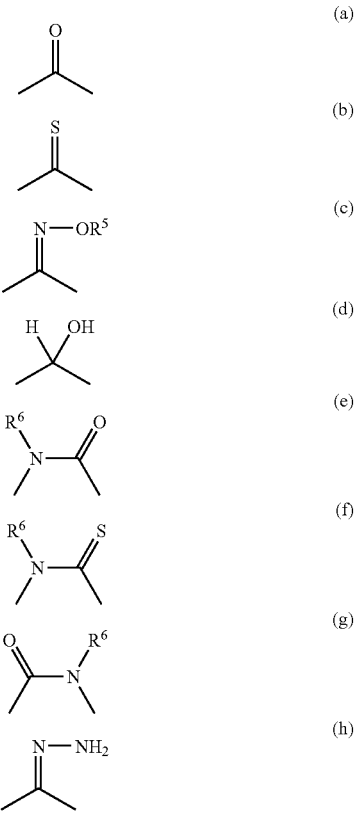

$R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents; and $R^5$ and $R^6$ independently represent hydrogen or $C_{1-6}$ alkyl;

for the manufacture of a medicament for the treatment and/or prevention of disorders for which the administration of a selective PI3K inhibitor is indicated.

More particularly, the present invention provides the use of a compound of formula (I) as depicted above, or a pharmaceutically acceptable salt or solvate thereof, wherein —X— represents a group of formula (a), (b), (c), (d) or (e) as defined above;

$R^1$ and $R^2$ are as defined above; and $R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

for the manufacture of a medicament for the treatment and/or prevention of disorders for which the administration of a selective PI3K inhibitor is indicated.

The present invention also provides a method for the treatment and/or prevention of disorders for which the administration of a selective PI3K inhibitor is indicated which comprises administering to a patient in need of such treatment an effective amount of a compound of formula (I) as defined above, or a pharmaceutically acceptable salt or solvate thereof.

Where $R^1$ and/or $R^2$ and/or $R^3$ and/or $R^4$ in the compounds of formula (I) above is other than hydrogen, this group may be unsubstituted, or substituted by one or more substituents.

Typically, $R^1$ and/or $R^2$ and/or $R^3$ and/or $R^4$ will be unsubstituted, or substituted by one or two substitutents. Suitably, $R^1$ and/or $R^2$ and/or $R^3$ and/or $R^4$ will be unsubstituted or monosubstituted.

For use in medicine, the salts of the compounds of formula (I) will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fiunaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope the use of solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Specific aryl($C_{2-6}$)alkenyl groups include 2-phenylethenyl and 3-phenylprop-2-en-1-yl.

A specific aryl($C_{2-6}$)alkynyl group is 3-phenylprop-2-yn-1-yl.

Particular biaryl($C_{1-6}$)alkyl groups include biphenyl and naphthylphenyl.

Suitable heterocycloalkyl groups include azetidinyl, tetrahydrofuranyl, pyrrolidinyl, imidazolidinyl, tetrahydropyranyl, piperidinyl, piperazinyl, morpholinyl and thiomorpholinyl.

Typical $C_{3-7}$ heterocycloalkyl($C_{1-6}$)alkyl groups, which may comprise benzo-fused analogues thereof, include indolinylmethyl, 1,2,3,4-tetrahydroquinolinylmethyl and 1,2,3,4-tetrahydroisoquinolinylmethyl.

Typical $C_{3-7}$ heterocycloalkylcarbonyl groups, which may comprise benzo-fused analogues thereof, include piperidinylcarbonyl, 1,2,3,4-tetrahydroquinolinylcarbonyl, 1,2,3,4-tetrahydroisoquinolinylmethyl and 1,2,3,4-tetrahydroquinoxalinylcarbonyl.

Suitable heteroaryl groups include furyl, benzofuryl, dibenzofuryl, thienyl, benzothienyl, pyrrolyl, indolyl, pyrrolo[2,3-b]pyridinyl, pyrazolyl, indazolyl, oxazolyl, isoxazolyl, thiazolyl, isothiazolyl, imidazolyl, benzimidazolyl, oxadiazolyl, thiadiazolyl, triazolyl, benzotriazolyl, tetrazolyl, pyridinyl, quinolinyl, isoquinolinyl, pyridazinyl, pyrimidinyl and pyrazinyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)-enol ($CH=CHOH$) tautomers. Formula (I) and the formulae depicted hereinafter are intended to represent all individual tautomers and all possible mixtures thereof, unless stated or shown otherwise.

Specific sub-classes of compounds of use in the present invention are represented by the compounds of formula (IA), (IB), (IC), (ID), (IE), (IF), (IG) and (IH):

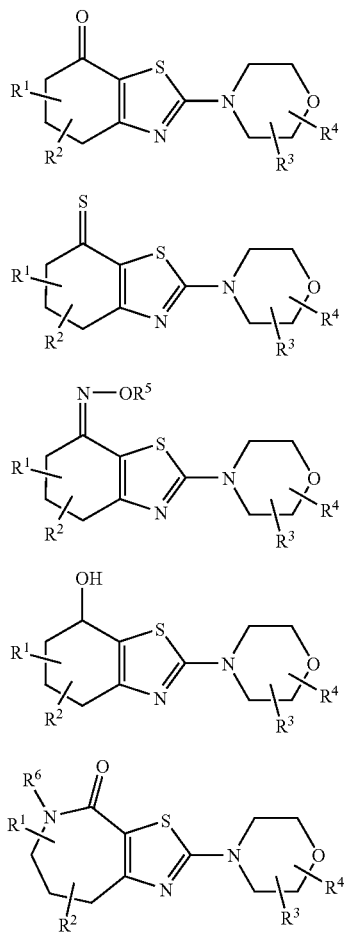

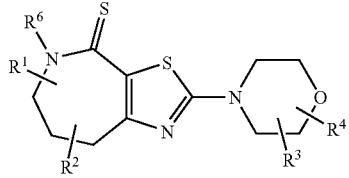

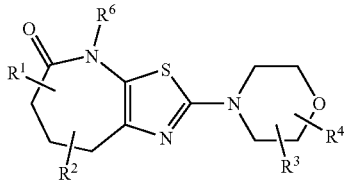

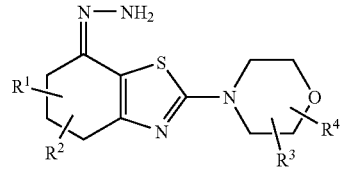

wherein $R^1$, $R^2$, $R^3$, $R^4$, $R^5$ and $R^6$ are as defined above.

In a specific embodiment, the present invention provides the use, for the manufacture of a medicament for the treatment and/or prevention of disorders for which the administration of a selective PI3K inhibitor is indicated, of a compound selected from the following:

2-(morpholin-4-yl)-5,6-dihydro-1,3-benzothiazol-7(4H)-one;
5,5-dimethyl-2-(morpholin-4-yl)-5,6-dihydro-1,3-benzothiazol-7(4H)-one;
2-(morpholin-4-yl)-5,6,7,8-tetrahydro-4H-[1,3]thiazolo[5,4-c]azepin-4-one;
7,7-dimethyl-2-(morpholin-4-yl)-5,6,7,8-tetrahydro-4H-[1,3]thiazolo[5,4-c]azepin-4-one;

and pharmaceutically acceptable salts and solvates thereof.

Likewise, the present invention provides a method for the treatment and/or prevention of disorders for which the administration of a selective PI3K inhibitor is indicated which comprises administering to a patient in need of such treatment an effective amount of a compound selected from the following:

2-(morpholin-4-yl)-5,6-dihydro-1,3-benzothiazol-7(4H)-one;
5,5-dimethyl-2-(morpholin-4-yl)-5,6-dihydro-1,3-benzothiazol-7(4H)-one;
2-(morpholin-4-yl)-5,6,7,8-tetrahydro-4H-[1,3]thiazolo[5,4-c]azepin-4-one;
7,7-dimethyl-2-(morpholin-4-yl)-5,6,7,8-tetrahydro-4H-[1,3]thiazolo[5,4-c]azepin-4-one;

and pharmaceutically acceptable salts and solvates thereof.

Certain compounds falling within the definition of formula (I) above are novel. Accordingly, in one aspect, the present invention provides a compound of formula (IB) as depicted above, or a pharmaceutically acceptable salt or solvate thereof, wherein $R^1$, $R^2$, $R^3$ and $R^4$ are as defined above. In another aspect, the present invention provides a compound of formula (IC) as depicted above, or a pharmaceutically acceptable salt or solvate thereof, wherein $R^1$, $R^2$, $R^3$, $R^4$ and $R^5$ are as defined above. In an additional aspect, the present invention provides a compound of formula (ID) as depicted above, or a pharmaceutically acceptable salt or solvate thereof, wherein $R^1$, $R^2$, $R^3$ and $R^4$ are as defined above. In a further aspect, the present invention provides a compound of formula (IF) as depicted above, or a pharmaceutically acceptable salt or solvate thereof, wherein $R^1$, $R^2$, $R^3$, $R^4$ and $R^6$ are as defined above. In a still further aspect, the present invention provides a compound of formula (IG) as depicted above, or a pharmaceutically acceptable salt or solvate thereof, wherein $R^1$, $R^2$, $R^3$, $R^4$ and $R^6$ are as defined above. In yet further aspect, the present invention provides a compound of formula (IH) as depicted above, or a pharmaceutically acceptable salt or solvate thereof, wherein $R^1$, $R^2$, $R^3$ and $R^4$ are as defined above.

In a further aspect, the present invention provides a compound of formula (IA) as depicted above, or a pharmaceutically acceptable salt or solvate thereof, wherein $R^1$, $R^2$, $R^3$ and $R^4$ are as defined above, with the exception of the following compounds: 2-(morpholin-4-yl)-5,6-dihydro-1,3-benzothiazol-7(4H)-one; and 5,5-dimethyl-2-(morpholin-4-yl)-5,6-dihydro-1,3-benzothiazol-7(4H)-one.

In a still further aspect, the present invention provides a compound of formula (IE) as depicted above, or a pharmaceutically acceptable salt or solvate thereof, wherein $R^1$, $R^2$, $R^3$, $R^4$ and $R^6$ are as defined above, with the exception of the following compounds: 2-(morpholin-4-yl)-5,6,7,8-tetrahydro-4H-[1,3]thiazolo[5,4-c]azepin-4-one; and 7,7-dimethyl-2-(morpholin-4-yl)-5,6,7,8-tetrahydro-4H-[1,3]thiazolo[5,4-c]azepin-4-one.

In one embodiment, the present invention provides a compound of formula (IA) or (IE) as depicted above, or a pharmaceutically acceptable salt or solvate thereof, wherein $R^1$ represents hydrogen; or $C_{2-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and $R^2$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents; and $R^6$ represents hydrogen or $C_{1-6}$ alkyl.

In a particular aspect of this embodiment, the present invention provides a compound of formula (IA) or (IE) as depicted above, or a pharmaceutically acceptable salt or solvate thereof, wherein $R^1$ represents hydrogen; or $C_{2-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and $R^2$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents; and $R^6$ represents hydrogen or $C_{1-6}$ alkyl.

In another embodiment, the present invention provides a compound of formula (IA) or (IE) as depicted above, or a pharmaceutically acceptable salt or solvate thereof, wherein $R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when talken together with the carbon atoms to which they are attached, $C_{1-57}$ cycloalkyl, phenyl or heteroaryl, any of which groups may be optionally benzo-fused and/or substituted by one or more substituents;

$R^3$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; and $R^4$ represents $C_{1-6}$ alkyl, $C_{3-7}$ cycloalkyl, $C_{3-7}$ cycloalkyl($C_{1-6}$)alkyl, aryl, aryl-($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl-($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents; and $R^6$ represents hydrogen or $C_{1-6}$ alkyl.

In a particular aspect of this embodiment, the present invention provides a compound of formula (IA) or (IE) as depicted above, or a pharmaceutically acceptable salt or solvate thereof, wherein $R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and $R^4$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents; and $R^6$ represents hydrogen or $C_{1-6}$ alkyl.

Suitably, $R^1$ represents hydrogen; or $C_{1-6}$ alkyl, aryl or heteroaryl, any of which groups may be optionally substituted by one or more substituents.

Suitably, $R^2$ represents hydrogen or optionally substituted $C_{1-6}$ alkyl.

Examples of typical substituents on $R^1$ and/or $R^2$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^1$ and/or $R^2$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^1$ include hydrogen, methyl, n-propyl, isopropyl, phenyl, chlorophenyl, methoxyphenyl, methylthiophenyl and furyl. A particular value of $R^1$ is methyl.

Typical values of $R^2$ include hydrogen and methyl. In one embodiment, $R^2$ is hydrogen. In another embodiment, $R^2$ is $C_{1-6}$ alkyl, especially methyl.

Alternatively, $R^1$ and $R^2$, when both are attached to the same carbon atom, may together form an optionally substituted spiro linkage. Thus, $R^1$ and $R^2$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^1$ and $R^2$, when taken together with the carbon atom to which they are both attached, may suitably represent an optionally substituted cyclopentyl, cyclohexyl, pyrrolidine or piperidine ring, especially cyclopentyl or cyclohexyl.

Alternatively, $R^1$ and $R^2$, when attached to adjacent carbon atoms, may together form an optionally benzo-fused and/or substituted cycloalkyl, phenyl or heteroaryl (e.g. pyridinyl) ring fused to the ring containing the variable X. Thus, $R^1$ and $R^2$, when attached to adjacent carbon atoms, may represent, when taken together with the carbon atoms to which they are attached, $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^1$ and $R^2$, when taken together with the adjacent carbon atoms to which they are attached, suitably represent a phenyl ring fused to the ring containing the variable X. Also in this context, in another embodiment, $R^1$ and $R^2$, when taken together with the adjacent carbon atoms to which they are attached, suitably represent a benzo-fused cyclopentyl ring, i.e. an indanyl moiety fused to the ring containing the variable X.

Typically, $R^3$ represents hydrogen; or $C_{1-6}$ alkyl, aryl, aryl($C_{1-6}$)alkyl, aryl-($C_{2-6}$)alkynyl, biaryl($C_{1-6}$)alkyl, $C_{3-7}$ heterocycloalkyl($C_{1-6}$)alkyl, $C_{3-7}$ heterocycloalkyl-carbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Suitably, $R^3$ represents hydrogen; or $C_{1-6}$ allyl, aryl, aryl ($C_{1-6}$)alkyl, $C_{3-7}$ heterocycloalkyl($C_{1-6}$)alkyl or heteroaryl (C$_{1-6}$)alkyl, any of which groups may be optionally substituted by one or more substituents.

In a representative embodiment, R$^3$ represents C$_{1-6}$ alkyl, aryl(C$_{1-6}$)alkyl, biaryl-(C$_{1-6}$)alkyl, heteroaryl(C$_{1-6}$)alkyl or heteroaryl-aryl(C$_{1-6}$)alkyl, any of which groups may be optionally substituted by one or more substituents. Preferably, R$^3$ represents methyl, arylmethyl, biarylmethyl, heteroarylmethyl or heteroaryl-arylmethyl, any of which groups may be optionally substituted by one or more substituents.

In a particular embodiment, R$^3$ represents substituted or unsubstituted indolyl-(C$_{1-6}$)alkyl. Advantageously, R$^3$ represents substituted or unsubstituted indolylmethyl.

Illustratively, R$^3$ represents hydrogen; or methyl, phenyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinyl-methyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofuiylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Suitably, R$^4$ represents hydrogen or optionally substituted C$_{1-6}$ alkyl.

Examples of suitable substituents on R$^3$ and/or R$^4$ include halogen, cyano, nitro, C$_{1-6}$ alkyl, hydroxy(C$_{1-6}$)alkyl, trifluoromethyl, aryl(C$_{1-6}$)alkyl, hydroxy, C$_{1-6}$ alkoxy, difluoromethoxy, trifluoromethoxy, aryloxy, aryl(C$_{1-6}$)alkoxy, methylenedioxy, C$_{1-6}$ alkylthio, arylthio, C$_{1-6}$ alkylsulphonyl, arylsulphonyl, C$_{1-6}$ alkylsulphonyloxy, amino, C$_{1-6}$ alkylamino, di(C$_{1-6}$)alkylamino, phenylamino, [(C$_{1-6}$)alkyl](phenyl)amino, pyridinylamino, pyrrolidinyl, morpholinyl, C$_{2-6}$ alkylcarbonylamino, benzofurylcarbonylamino, C$_{2-6}$ alkoxycarbonylamino, C$_{1-6}$ alkylsulphonylamino, arylsulphonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, benzothienylmethylaminocarbonyl, aminosulphonyl, C$_{1-6}$ alkylaminosulphonyl and di(C$_{1-6}$)alkylaminosulphonyl.

Selected examples of suitable substituents on R$^3$ and/or R$^4$ include halogen, cyano, C$_{1-6}$ alkyl, hydroxy(C$_{1-6}$)alkyl, trifluoromethyl, aryl(C$_{1-6}$)alkyl, hydroxy, C$_{1-6}$ alkoxy, trifluoromethoxy, aryloxy, aryl(C$_{1-6}$)alkoxy, methylenedioxy, C$_{1-6}$ alkylthio, arylthio, arylsulphonyl, C$_{1-6}$ alkylsulphonyloxy, amino, phenylamino, [(C$_{1-6}$)alkyl](phenyl)amino, pyridinylamino, pyrrolidinyl, morpholinyl, C$_{2-6}$ alkylcarbonylamino, benzofurylcarbonylamino, C$_{1-6}$ alkylsulphonylamino, arylsulphonylamino, C$_{2-6}$ alkylcarbonyl, aminocarbonyl and benzothienylmethylaminocarbonyl.

Examples of typical substituents on R$^3$ and/or R$^4$ include halogen, cyano, nitro, C$_{1-6}$ alkyl, trifluoromethyl, hydroxy, C$_{1-6}$ alkoxy, difluoromethoxy, trifluoromethoxy, aryloxy, C$_{1-6}$ alkylthio, C$_{1-6}$ alkylsulphonyl, amino, C$_{1-6}$ alkylamino, di(C$_{1-6}$)alkylamino, phenylamino, [(C$_{1-6}$)alkyl](phenyl)amino, morpholinyl, C$_{2-6}$ alkylcarbonylamino, C$_{2-6}$ alkoxycarbonylamino, C$_{1-6}$ alkylsulphonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulphonyl, C$_{1-6}$ alkylaminosulphonyl and di(C$_{1-6}$)alkylaminosulphonyl; especially halogen, C$_{1-6}$ alkyl, phenylamino, [(C$_{1-6}$)alkyl](phenyl)amino, morpholinyl or C$_{2-6}$ alkylcarbonyl.

Examples of representative substituents on R$^3$ and/or R$^4$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Selected examples of representative substituents on R$^3$ and/or R$^4$ include fluoro, chloro, bromo, cyano, methyl, hydroxymethyl, trifluoromethyl, benzyl, hydroxy, methoxy, ethoxy, trifluoromethoxy, phenoxy, benzyloxy, methylenedioxy, methylthio, phenylthio, phenylsulphonyl, methylsulphonyloxy, amino, phenylamino, N-methyl-N-phenylamino, pyridinylamino, pyrrolidinyl, morpholinyl, acetylamino, benzofurylcarbonylamino, methylsulphonylamino, phenylsulphonylamino, acetyl, aminocarbonyl and benzothienylmethylaminocarbonyl.

Examples of particular substituents on R$^3$ and/or R$^4$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, phenylamino, N-methyl-N-phenylamino, morpholinyl, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, bromo, methyl, phenylamino, N-methyl-N-phenylamino, morpholinyl or acetyl.

Specific values of R$^3$ include hydrogen, methyl, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenyl-methyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxy-biphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methyl-indolylmethyl, hydroxyindolylmethyl, benzyloxyindolylmethyl, acetylindolylmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbelizyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Typical values of $R^3$ include hydrogen, methyl, phenylaminomethyl, N-methyl-N-phenylaminomethyl, phenyl, benzyl, chlorobenzyl, bromobenzyl, morpholinyl-benzyl, phenylethyl, naphthylmethyl, indolinylmethyl, 1,2,3,4-tetrahydroquinolinylmethyl, 1,2,3,4-tetrahydroisoquinolinylmethyl, indolylmethyl, methylindolyl-methyl and acetylindolyl-methyl.

Typical values of $R^4$ include hydrogen and methyl. In a preferred embodiment, $R^4$ is hydrogen. In another embodiment, $R^4$ is $C_{1-6}$ alkyl, especially methyl.

Alternatively, $R^3$ and $R^4$, when both are attached to the same carbon atom, may together form an optionally substituted spiro linkage. Thus, $R^3$ and $R^4$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^3$ and $R^4$, when taken together with the carbon atom to which they are both attached, may suitably represent an optionally substituted cyclopentyl, cyclohexyl, pyrrolidine or piperidine ring, especially cyclopentyl or cyclohexyl.

Alternatively, $R^3$ and $R^4$, when attached to adjacent carbon atoms, may together form an optionally benzo-fused and/or substituted cycloalkyl, phenyl or heteroaryl (e.g. pyridinyl) ring fused to the morpholine ring. Thus, $R^3$ and $R^4$, when attached to adjacent carbon atoms, may represent, when taken together with the carbon atoms to which they are attached, $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^3$ and $R^4$, when taken together with the adjacent carbon atoms to which they are attached, suitably represent a phenyl ring fused to the morpholine ring. Also in this context, in another embodiment, $R^3$ and $R^4$, when taken together with the adjacent carbon atoms to which they are attached, suitably represent a benzo-fused cyclopentyl ring, i.e. an indanyl moiety fused to the morpholine ring.

In one embodiment, $R^5$ represents hydrogen. In another embodiment, $R^5$ represents $C_{1-6}$ alkyl, especially methyl.

In one embodiment, $R^6$ represents hydrogen. In another embodiment, $R^6$ represents $C_{1-6}$ alkyl, especially methyl.

One sub-class of novel compounds according to the invention is represented by the compounds of formula (IIA), and pharmaceutically acceptable salts and solvates thereof:

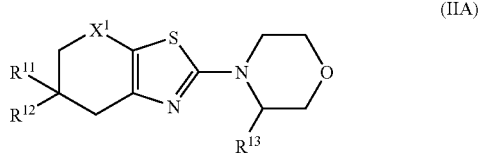

(IIA)

wherein
—$X^1$— represents a group of formula (a) or (e) as defined above;

$R^{11}$ represents hydrogen or optionally substituted $C_{2-6}$ alkyl; and $R^{12}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$) alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

The present invention also provides a compound of formula (IIA) as depicted above, or a pharmaceutically acceptable salt or solvate thereof, wherein $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and
—$X^1$—, $R^{11}$ and $R^{12}$ are as defined above.

In one embodiment, —$X^1$— represents a group of formula (a). In another embodiment, —$X^1$— represents a group of formula (e).

Where $R^{11}$ and/or $R^{12}$ and/or $R^{13}$ in the compounds of formula (IIA) above is stated to be optionally substituted, this group may be unsubstituted, or substituted by one or more substituents. Typically, $R^{11}$ and/or $R^{12}$ and/or $R^{13}$ will be unsubstituted, or substituted by one or two substitutents. Suitably, $R^{11}$ and/or $R^{12}$ and/or $R^{13}$ will be unsubstituted or monosubstituted.

Suitably, $R^{11}$ represents hydrogen or unsubstituted $C_{2-6}$ alkyl, especially hydrogen.

Suitably, $R^{12}$ represents $C_{1-6}$ alkyl, aryl or heteroaryl, any of which groups may be optionally substituted by one or more substituents.

Examples of typical substituents on $R^{11}$ and/or $R^{12}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylamino-carbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^{11}$ and/or $R^{12}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^{12}$ include methyl, n-propyl, isopropyl, phenyl, chlorophenyl, methoxyphenyl, methylthiophenyl and furyl.

Alternatively, $R^{11}$ and $R^{12}$ may together form an optionally substituted spiro linkage. Thus, $R^{11}$ and $R^{12}$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^{11}$ and $R^{12}$, when taken together with the carbon atom to which they are both attached, may suitably represent an optionally substituted cyclopentyl, cyclohexyl, pyrrolidine or piperidine ring, especially cyclopentyl or cyclohexyl.

Typically, $R^{13}$ represents hydrogen; or $C_{1-6}$ alkyl, aryl($C_{1-6}$)alkyl, aryl($C_{2-6}$)alkynyl, biaryl($C_{1-6}$)alkyl, $C_{3-7}$ heterocycloalkyl($C_{1-6}$)alkyl, $C_{3-7}$ heterocycloalkylcarbonyl, heteroaryl($C_{1-6}$)allyl, heteroaryl-aryl($C_{1-6}$)alkyl or aryl-heteroaryl($C_{1-6}$)alkyl, any of which groups may be optionally substituted by one or more substituents.

Suitably, $R^{13}$ represents hydrogen; or $C_{1-6}$ alkyl, aryl($C_{1-6}$)alkyl, $C_{3-7}$ heterocycloalkyl($C_{1-6}$)alkyl or heteroaryl($C_{1-6}$)alkyl, any of which groups may be optionally substituted by one or more substituents.

In a representative embodiment, $R^{13}$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^{13}$ represents methyl, arylmethyl, biarylmethyl, heteroarylmethyl or heteroaryl-arylmethyl, any of which groups may be optionally substituted by one or more substituents.

In a particular embodiment, $R^{13}$ represents substituted or unsubstituted indolyl-($C_{1-6}$)alkyl. Advantageously, $R^{13}$ represents substituted or unsubstituted indolylmethyl.

Illustratively, $R^{13}$ represents hydrogen; or methyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Examples of suitable substituents on $R^{13}$ include halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, methylenedioxy, $C_{1-6}$ alkylthio, arylthio, $C_{1-6}$ alkylsulphonyl, arylsulphonyl, $C_{1-6}$ alkylsulphonyloxy, amino, $C_{1-6}$ alkylamino, di($C_{1-6}$)alkylamino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, benzothienylmethylaminocarbonyl, aminosulphonyl, $C_{1-6}$ alkylaminosulphonyl and di($C_{1-6}$)alkylaminosulphonyl.

Selected examples of suitable substituents on $R^{13}$ include halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$)alkoxy, methylenedioxy, $C_{1-6}$ alkylthio, arylthio, arylsulphonyl, $C_{1-6}$ alkylsulphonyloxy, amino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{1-6}$ alkylsulphonylamino, arylsulphonylamino, $C_{2-6}$ alkylcarbonyl, aminocarbonyl and benzothienylmethylaminocarbonyl.

Examples of typical substituents on $R^{13}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, phenylamino, [($C_{1-6}$)alkyl](phenyl)amino, morpholinyl, $C_{2-6}$ alkylcarbonylamino, $C_{2-6}$ alkoxycarbonyl-amino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkyl, phenylamino, [($C_{1-6}$)alkyl](phenyl)amino, morpholinyl or $C_{2-6}$ alkylcarbonyl.

Examples of representative substituents on $R^{13}$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Selected examples of representative substituents on $R^{13}$ include fluoro, chloro, bromo, cyano, methyl, hydroxymethyl, trifluoromethyl, benzyl, hydroxy, methoxy, ethoxy, trifluoromethoxy, phenoxy, benzyloxy, methylenedioxy, methylthio, phenylthio, phenylsulphonyl, methylsulphonyloxy, amino, phenylamino, N-methyl-N-phenylamino, pyridinylamino, pyrrolidinyl, morpholinyl, acetylamino, benzofurylcarbonylamino, methylsulphonylamino, phenylsulphonylamino, acetyl, aminocarbonyl and benzothienylmethylaminocarbonyl.

Examples of particular substituents on $R^{13}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, phenylamino, N-methyl-N-phenylamino, morpholinyl, acetylamino, methoxycarbonyl-amino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, bromo, methyl, phenylamino, N-methyl-N-phenylamino, morpholinyl or acetyl.

Specific values of $R^{13}$ include hydrogen, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, benzyl, chlorobenzyl, bromobenzyl, pyrrolidinylbenzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylethyl, cyanobiphenylmethyl, methylbiphenylmethyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methyl-indolylmethyl, hydroxyindolylmethyl, benzyloxyindolylmethyl, acetylindolylhmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Typical values of $R^{13}$ include hydrogen, phenylaminomethyl, N-methyl-N-phenylaminomethyl, benzyl, chlorobenzyl, bromobenzyl, morpholinyl-benzyl, phenylethyl, naphthylmethyl, indolinylmethyl, 1,2,3,4-tetrahydroquinolinylmethyl, 1,2,3,4-tetrahydroisoquinolinylmethyl, indolylmethyl, methylindolyl-methyl and acetylindolyl-methyl.

Another sub-class of novel compounds according to the invention is represented by the compounds of formula (IIB), and pharmaceutically acceptable salts and solvates thereof:

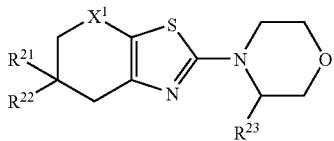

(IIB)

wherein

—$X^1$— is as defined above;

$R^{21}$ represents hydrogen or optionally substituted $C_{1-6}$ alkyl; and $R^{22}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{21}$ and $R^{22}$, when taken together with the carbon atom to which they are both attached, represent $C_{3-7}$ cycloalkyl or $C_{3-7}$ heterocycloalkyl, either of which groups may be optionally substituted by one or more substituents; and $R^{23}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

The present invention also provides a compound of formula (IIB) as depicted above, or a pharmaceutically acceptable salt or solvate thereof, wherein $R^{23}$ represents $C_{1-6}$ alkyl, $C_{3-7}$ cycloalkyl, $C_{3-7}$ cycloalkyl($C_{1-6}$)allyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; and —$X^1$—, $R^{21}$ and $R^{22}$ are as defined above.

Where $R^{21}$ and/or $R^{22}$ and/or $R^{23}$ in the compounds of formula (IIB) above is stated to be optionally substituted, this group may be unsubstituted, or substituted by one or more substituents. Typically, $R^{21}$ and/or $R^{22}$ and/or $R^{23}$ will be unsubstituted, or substituted by one or two substitutents. Suitably, $R^{21}$ and/or $R^{22}$ and/or $R^{23}$ will be unsubstituted or monosubstituted.

Suitably, $R^{21}$ represents hydrogen or unsubstituted $C_{1-6}$ alkyl.

Suitably, $R^{22}$ represents hydrogen; or $C_{1-6}$ alkyl, aryl or heteroaryl, any of which groups may be optionally substituted by one or more substituents.

Examples of typical substituents on $R^{21}$ and/or $R^{22}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylamino-carbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^{21}$ and/or $R^{22}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^{21}$ include hydrogen and methyl. In one embodiment, $R^{21}$ is hydrogen. In another embodiment, $R^{21}$ is methyl.

Typical values of $R^{22}$ include hydrogen, methyl, n-propyl, isopropyl, phenyl, chlorophenyl, methoxyphenyl, methylthiophenyl and furyl. A particular value of $R^{22}$ is methyl.

Alternatively, $R^{21}$ and $R^{22}$ may together form an optionally substituted spiro linkage. Thus, $R^{21}$ and $R^{22}$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^{21}$ and $R^{22}$, when taken together with the carbon atom to which they are both attached, may suitably represent an optionally substituted cyclopentyl, cyclohexyl, pyrrolidine or piperidine ring, especially cyclopentyl or cyclohexyl.

Typically, $R^{23}$ represents $C_{1-6}$ alkyl, aryl($C_{1-6}$)alkyl, aryl ($C_{2-6}$)alkynyl, biaryl-($C_{1-6}$)alkyl, $C_{3-7}$ heterocycloalkyl($C_{1-6}$) alkyl, $C_{3-7}$ heterocycloalkylcarbonyl, heteroaryl-($C_{1-6}$)alkyl, heteroaryl-aryl($C_{1-6}$)alkyl or aryl-heteroaryl($C_{1-6}$)alkyl, any of which groups may be optionally substituted by one or more substituents.

Suitably, $R^{23}$ represents $C_{1-6}$ alkyl, aryl($C_{1-6}$)alkyl, $C_{3-7}$ heterocycloalkyl($C_{1-6}$)alkyl or heteroaryl($C_{1-6}$)alkyl, any of which groups may be optionally substituted by one or more substituents.

In a representative embodiment, $R^{23}$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^{23}$ represents methyl, arylmethyl, biarylmethyl, heteroarylmethyl or heteroaryl-arylmethyl, any of which groups may be optionally substituted by one or more substituents.

In a particular embodiment, $R^{23}$ represents substituted or unsubstituted indolyl-($C_{1-6}$)alkyl. Advantageously, $R^{23}$ represents substituted or unsubstituted indolylmethyl.

Illustratively, $R^{13}$ represents methyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]-pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Examples of suitable substituents on $R^{23}$ include halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, methylenedioxy, $C_{1-6}$ alkylthio, arylthio, $C_{1-6}$ alkylsulphonyl, arylsulphonyl, $C_{1-6}$ alkylsulphonyloxy, amino, $C_{1-6}$ alkylamino, di($C_{1-6}$)alkylamino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, benzothienylmethylaminocarbonyl, aminosulphonyl, $C_{1-6}$ alkylaminosulphonyl and di($C_{1-6}$)alkylaminosulphonyl.

Selected examples of suitable substituents on $R^{23}$ include halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$)alkoxy, methylenedioxy, $C_{1-6}$ alkylthio, arylthio, arylsulphonyl, $C_{1-6}$ alkylsulphonyloxy, amino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{1-6}$ alkylsulphonylamino, arylsulphonylamino, $C_{2-6}$ alkylcarbonyl, aminocarbonyl and benzothienylmethylaminocarbonyl.

Examples of typical substituents on $R^{23}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, phenylamino, [($C_{1-6}$)alkyl](phenyl)amino, morpholinyl, $C_{2-6}$ alkylcarbonylamino, $C_{2-6}$ alkoxycarbonyl-amino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkyl, phenylamino, [($C_{1-6}$)alkyl](phenyl)amino, morpholinyl or $C_{2-6}$ alkylcarbonyl.

Examples of representative substituents on $R^{23}$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Selected examples of representative substituents on $R^{23}$ include fluoro, chloro, bromo, cyano, methyl, hydroxymethyl, trifluoromethyl, benzyl, hydroxy, methoxy, ethoxy, trifluoromethoxy, phenoxy, benzyloxy, methylenedioxy, methylthio, phenylthio, phenylsulphonyl, methylsulphonyloxy, amino, phenylamino, N-methyl-N-phenylamino, pyridinylamino, pyrrolidinyl, morpholinyl, acetylamino, benzofurylcarbonylamino, methylsulphonylamino, phenylsulphonylamino, acetyl, aminocarbonyl and benzothienylmethylaminocarbonyl.

Examples of particular substituents on $R^{23}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, phenylamino, N-methyl-N-phenylamino, morpholinyl, acetylamino, methoxycarbonyl-amino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, bromo, methyl, phenylamino, N-methyl-N-phenylamino, morpholinyl or acetyl.

Specific values of $R^{23}$ include phenoxymethyl, phenylthiomethyl, aminomethyl, phenylaminomethyl, N-methyl-N-phenylaminomethyl, pyridinylaminomethyl, benzofurylcarbonylaminomethyl, phenylsulphonylaminomethyl, benzothienylmethylaminocarbonylmethyl, benzyl, chlorobenzyl, bromobenzyl, pyrrolidinylbenzyl, morpholinylbenzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenylmethyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methyl-indolylmethyl, hydroxyindolylmethyl, benzyloxyindolylmethyl, acetylindolylmethyl, methylsulphoniyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Typical values of $R^{23}$ include phenylaminomethyl, N-methyl-N-phenylaminomethyl, benzyl, chlorobenzyl, bromobenzyl, morpholinyl-benzyl, phenylethyl, naphthylmethyl, indolinylmethyl, 1,2,3,4-tetrahydroquinolinylmethyl, 1,2,3,4-tetrahydroisoquinolinylmethyl, indolylmethyl, methylindolyl-methyl and acetylindolyl-methyl.

A further sub-class of novel compounds according to the invention is represented by the compounds of formula (IIC), and pharmaceutically acceptable salts and solvates thereof:

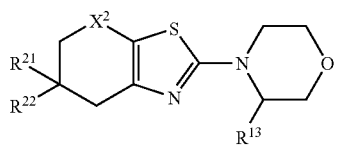

(IIC)

wherein

—$X^2$— represents a group of formula (b), (c), (d), (f), (g) or (h) as defined above;

$R^{13}$ is as defined above in relation to formula (IIA); and $R^{21}$ and $R^{22}$ are as defined above in relation to formula (IIB).

Suitably, —$X^2$— represents a group of formula (b), (c) or (d) as defined above.

In one embodiment, —$X^2$— represents a group of formula (b). In another embodiment, —$X^2$— represents a group of formula (c). In a further embodiment, —$X^2$— represents a group of formula (d). In a still further embodiment, —$X^2$— represents a group of formula (f). In a yet further embodiment, —$X^2$— represents a group of formula (g). In an additional embodiment, —$X^2$— represents a group of formula (h).

One particular sub-group of the compounds of formula (IIB) is represented by the compounds of formula (IID), and pharmaceutically acceptable salts and solvates thereof:

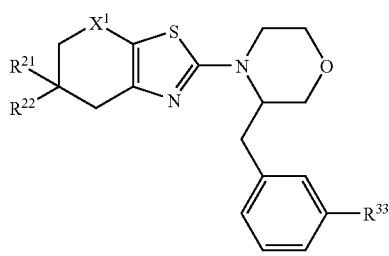

(IID)

wherein

—$X^1$—, $R^{21}$ and $R^{22}$ are as defined above; and $R^{33}$ represents aryl or heteroaryl, either of which groups may be optionally substituted by one or more substituents.

In one embodiment, $R^{33}$ represents unsubstituted or substituted aryl. In another embodiment, $R^{33}$ represents unsubstituted or substituted heteroaryl.

Illustratively, $R^{33}$ represents phenyl, naphthyl, benzofuryl, thienyl, benzothienyl, indolyl, isoxazolyl, pyrazolyl, pyridinyl or pyrimidinyl, any of which groups may be optionally substituted by one or more substituents.

Selected examples of suitable substituents on $R^{33}$ include halogen, cyano, $C_{1-6}$ alkyl, hydroxy($C_{1-6}$)alkyl, trifluoromethyl, $C_{1-6}$ alkoxy, trifluoromethoxy, aryloxy, methylenedioxy, $C_{1-6}$ alkylthio, arylsulphonyl, amino, $C_{2-6}$ alkylcarbonylamino, $C_{1-6}$ alkylsulphonylamino, $C_{2-6}$ alkylcarbonyl and aminocarbonyl.

Selected examples of representative substituents on $R^{33}$ include fluoro, chloro, bromo, cyano, methyl, hydroxymethyl, trifluoromethyl, methoxy, ethoxy, trifluoromethoxy, phenoxy, methylenedioxy, methylthio, phenylsulphonyl, amino, acetylamino, methylsulphonylamino, acetyl and aminocarbonyl.

Specific values of $R^{33}$ include phenyl, fluorophenyl, difluorophenyl, chlorophenyl, dichlorophenyl, bromophenyl, cyanophenyl, methylphenyl, (fluoro)(methyl)phenyl, dimethylphenyl, hydroxymethylphenyl, trifluoromethylphenyl, bis(trifluoromethyl)-phenyl, methoxyphenyl, dimethoxyphenyl, ethoxyphenyl, methylenedioxyphenyl, trifluoromethoxyphenyl, phenoxyphenyl, methylthiophenyl, aminophenyl, acetylamino-phenyl, methylsulphonylaminophenyl, acetylphenyl, aminocarbonylphenyl, naphthyl, benzofuryl, thienyl, methylthienyl, acetylthienyl, benzothienyl, phenylsulphonylindolyl, dimethylisoxazolyl, methylpyrazolyl, benzylpyrazolyl, pyridinyl, fluoropyridinyl, chloropyridinyl, methoxypyridinyl and pyrimidinylbenzyl.

Another particular sub-group of the compounds of formula (IIB) is represented by the compounds of formula (IIE), and pharmaceutically acceptable salts and solvates thereof:

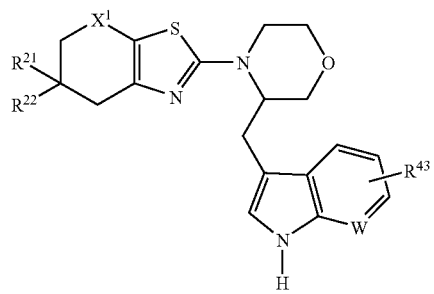

(IIE)

wherein

—$X^1$—, $R^{21}$ and $R^{22}$ are as defined above;

W represents CH or N; and $R^{43}$ represents hydrogen, halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$) alkoxy, $C_{1-6}$ alkylthio, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl or aminocarbonyl.

In a preferred embodiment, W is CH. In another embodiment, W is N.

Suitable values of $R^{43}$ include hydrogen, $C_{1-6}$ alkyl, hydroxy, aryl($C_{1-6}$)alkoxy and $C_{1-6}$ alkylsulphonyloxy.

Specific values of $R^{43}$ include hydrogen, fluoro, chloro, bromo, cyano, methyl, hydroxymethyl, trifluoromethyl, benzyl, hydroxy, methoxy, ethoxy, trifluoromethoxy, phenoxy, benzyloxy, methylthio, phenylsulphonyl, methylsulphonyloxy, amino, acetylamino, methylsulphonylamino, acetyl and aminocarbonyl; especially hydrogen, methyl, hydroxy, benzyloxy or methylsulphonyloxy.

A particular value of $R^{43}$ is hydrogen.

Specific novel compounds in accordance with the present invention include each of the compounds whose preparation is described in accompanying Examples 1-5, 7-42, 45-47, 49, 50, and 51-158, and pharmaceutically acceptable salts and solvates thereof.

The present invention also provides a pharmaceutical composition which comprises a novel compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

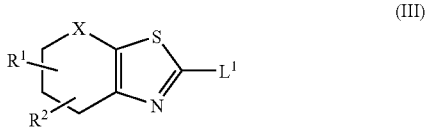

(III)

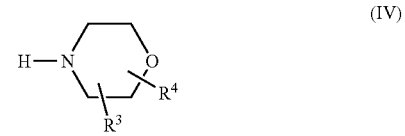

(IV)

wherein $R^1$, $R^2$, $R^3$, $R^4$ and X are as defined above, and $L^1$ represents a suitable leaving group.

The leaving group $L^1$ is typically a halogen atom, e.g. bromo.

The reaction is conveniently effected at an elevated temperature in a suitable solvent, e.g. a lower alkanol such as isopropanol or a cyclic ether such as tetrahydrofuran, typically under basic conditions, e.g. in the presence of an organic base such as N,N-diisopropylethylamine.

Alternatively, the reaction may be effected at an elevated temperature in a solvent such as 2-ethoxyethanol in the presence of a catalytic quantity of a mineral acid, e.g. concentrated hydrochloric acid.

The intermediates of formula (III) above wherein $L^1$ is bromo may be prepared from a compound of formula (V):

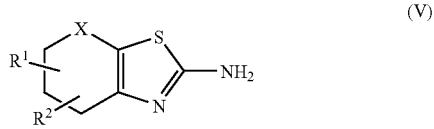

(V)

wherein $R^1$, $R^2$ and X are as defined above; by diazotization/bromination.

The reaction is conveniently effected by stirring compound (V) with tert-butyl nitrite and copper(II) bromide in a suitable solvent, e.g. acetonitrile.

The intermediates of formula (V) above may be prepared by reacting thiourea with a compound of formula (VI):

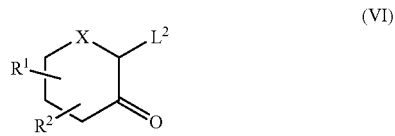

(VI)

wherein $R^1$, $R^2$ and X are as defined above, and $L^2$ represents a suitable leaving group.

The leaving group $L^2$ is typically a halogen atom, e.g. bromo.

The reaction is conveniently effected at an elevated temperature in a suitable solvent, e.g. a cyclic ether such as tetrahydrofuran, typically under basic conditions, e.g. in the presence of an organic base such as N,N-diisopropylethylamine.

In another procedure, the compounds of formula (I) may be prepared by a process which comprises reacting a compound of formula (VI) as defined above with a compound of formula (VII):

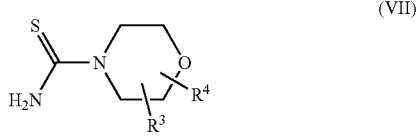

(VII)

wherein $R^3$ and $R^4$ are as defined above; under conditions analogous to those described above for the reaction between thiourea and compound (VI).

Where they are not commercially available, the starting materials of formula (IV), (VI) and (VII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (IA) may be converted into the corresponding compound of formula (IB) by treatment with Lawesson's Reagent (i.e. 2,4-bis(4-methoxyphenyl)-1,3-dithia-2,4-diphosphetane-2,4-disulphide). Similarly, a compound of formula (IE) may be converted into the corresponding compound of formula (IF) by treatment with Lawesson's Reagent. A compound of formula (IA) may be converted into the corresponding compound of formula (IC) by treatment with a hydroxylamine derivative of formula $H_2N$—$OR^5$. A compound of formula (IA) may be converted into the corresponding compound of formula (ID) by treatment with a reducing agent such as lithium aluminium hydride. A compound of formula (IA) may be converted into the corresponding compound of formula (IG) by treatment with hydroxylamine-O-sulfonic acid, typically in the presence of formic acid at an elevated temperature. A compound of formula (IA) may be converted into the corresponding compound of formula (IH) by treatment with hydrazine hydrate. A compound of formula (IC) may be converted into the corresponding compound of formula (IE) by treatment with p-toluenesulphonyl chloride, typically in the presence of pyridine at an elevated temperature. A compound of formula (IA) wherein $R^1$ is hydrogen may be converted into the corresponding compound wherein $R^1$ is methyl by treatment with a methyl halide, e.g. iodomethane, in the presence of a strong base, e.g. lithium diisopropylamide.

A compound of formula (I) wherein $R^3$ represents aryl($C_{1-6}$)alkyl, substituted on the aryl moiety by a halogen atom such as bromo, may be converted into the corresponding compound wherein $R^3$ represents biaryl($C_{1-6}$)alkyl or heteroaryl-aryl($C_{1-6}$)alkyl by treatment with, respectively, an aryl or heteroaryl boronic acid, in the presence of a catalyst. Similarly, a compound of formula (I) wherein $R^3$ represents heteroaryl($C_{1-6}$)allyl, substituted on the heteroaryl moiety by a halogen atom such as bromo, may be converted into the corresponding compound wherein $R^3$ represents aryl-heteroaryl($C_{1-6}$)alkyl by treatment with an aryl boronic acid, in the presence of a catalyst. The catalyst may typically be a transition metal catalyst. A suitable catalyst is tetrakis(triphenylphosphine)palladium(0), in which case the transformation may conveniently be effected at an elevated temperature in the presence of a base such as sodium carbonate or potassium carbonate, in an inert solvent such as 1,2-dimethoxyethane or 1,4-dioxane. Alternatively, the catalyst may be palladium(II) acetate, in which case the transformation may conveniently be effected at an elevated temperature in the presence of 2-dicyclohexylphosphino-2',6'-dimethoxybiphenyl and potassium phosphate.

A compound of formula (I) wherein $R^3$ represents hydroxymethyl may be converted into the corresponding compound wherein $R^3$ represents a substituted aminomethyl moiety, e.g. phenylaminomethyl, N-methyl-N-phenylaminomethyl, pyridin-3-ylaminomethyl, indolin-1-ylmethyl, 1,2,3,4-tetrahydroquinolin-1-ylmethyl or 1,2,3,4-tetrahydroisoquinolin-2-ylmethyl, by a two-stage procedure which comprises (i) Swern oxidation of the hydroxymethyl derivative by treatment with oxalyl chloride and dimethyl sulphoxide in the presence of triethylamine; and (ii) reductive amination of the formyl derivative thereby obtained by treatment with the appropriate amine, e.g. aniline, N-methylaniline, 3-aminopyridine, indoline, 1,2,3,4-tetrahydroquinoline or 1,2,3,4-tetrahydroisoquinoline, in the presence of a reducing agent such as sodium cyanoborohydride.

A compound of formula (I) wherein $R^3$ represents hydroxymethyl may be converted into the corresponding compound wherein $R^3$ represents an optionally substituted $C_{3-7}$ heterocycloalkylcarbonyl moiety, e.g. piperidin-1-ylcarbonyl, 1,2,3,4-tetrahydroquinolin-1-ylcarbonyl, 6-methyl-1,2,3,4-tetrahydroquinolin-1-ylcarbonyl, 6-methoxy-1,2,3,4-tetrahydroquinolin-1-ylcarbonyl, 1,2,3,4-tetrahydroisoquinolin-2-ylcarbonyl or 1,2,3,4-tetrahydroquinoxalin-1-ylcarbonyl, by a two-stage procedure which comprises (i) oxidation of the hydroxymethyl moiety by treatment with potassium permanganate; and (ii) reaction of the carboxy derivative thereby obtained with the appropriate amine, e.g. piperidine, 1,2,3,4-tetrahydroquinoline, 6-methyl-1,2,3,4-tetrahydroquinoline, 6-methoxy-1,2,3,4-tetrahydroquinoline, 1,2,3,4-tetrahydro-isoquinoline or 1,2,3,4-tetrahydroquinoxaline, in the presence of a condensing agent such as 1-(3-dimethylaminopropyl)-3-ethylcarbodiimide, or O-(benzotriazol-1-yl)-N,N,N',N'-tetramethyluronium hexafluorophosphate (HBTU).

A compound of formula (I) wherein $R^3$ contains a phenyl moiety substituted by chloro may be converted into the corresponding compound wherein the phenyl ring is substituted by morpholin-4-yl by treatment with morpholine in the presence of tris(dibenzylideneacetone)dipalladium(0), 2-(di-tert-butylphosphino)biphenyl and sodium tert-butoxide. A compound of formula (I) wherein $R^3$ contains a phenyl moiety substituted by bromo may be converted into the corresponding compound wherein the phenyl ring is substituted by pyrrolidin-1-yl by treatment with pyrrolidine in the presence of tris(dibenzylideneacetone)dipalladium(0), 2-dicyclohexylphosphino-2',4',6'-triisopropyl-1,1'-biphenyl and a base such as potassium carbonate. A compound of formula (I) wherein $R^3$ contains an indole moiety may be methylated on the indole ring by treatment with a methyl halide, e.g. iodomethane, in the presence of a strong base such as sodium hydride. A compound of formula (I) wherein $R^3$ contains an indole moiety may be acetylated on the indole ring by treatment with acetic anhydride and 4-dimethylamino-pyridine, typically in the presence of an organic base such as triethylamine. A compound of formula (I) wherein $R^3$ contains an indoline moiety may be converted into the corresponding compound wherein $R^3$ contains an indole moiety by treatment with an oxidising agent such as manganese dioxide. A compound of formula (I) wherein $R^3$ contains a hydroxy substituent may be converted into the corresponding compound wherein $R^3$ contains a $C_{1-6}$ alkylsulphonyloxy substituent, e.g. methylsulphonyloxy, by treatment with a $C_{1-6}$ alkylsulphonyl halide, e.g. methanesulphonyl chloride. A compound of formula (I) wherein $R^3$ contains an amino (—$NH_2$) or carboxy (—$CO_2H$) moiety may be converted into the corresponding compound wherein $R^3$ contains an amido moiety (—NHCO— or —CONH— respectively) by treatment with, respectively, a compound containing a carboxy or amino group, in the presence of O-(benzotriazol-1-yl)-N,N,N',N'-tetramethyluronium hexafluorophosphate (HBTU), typically in a dipolar aprotic solvent such as N,N-dimethylformamide. A compound of formula (I) wherein R contains an amino substituent may be converted into the corresponding compound wherein $R^3$ contains an arylsulphonylamino substituent, e.g. phenylsulphonylamino, by treatment with an arylsulphonyl halide, e.g. benzenesulphonyl chloride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 μM or better.

EXAMPLES

| | |
|---|---|
| AcOH—acetic acid | EtOAc—ethyl acetate |
| $Et_2O$—diethyl ether | Me—methyl |
| MeCN—acetonitrile | MeOH—methanol |
| DCM—dichloromethane | DMSO—dimethylsulphoxide |
| IPA—isopropanol | THF—tetrahydrofuran |
| DMAP—4-dimethylaminopyridine | PhMe—toluene |
| $Pd_2dba_3$—tris(dibenzylideneacetone)dipalladium(0) | |
| Ac—acetyl | dba—dibenzylideneacetone |
| NMM—N-methylmorpholine | BOC—tert-butoxycarbonyl |
| DMF—N,N-dimethylformamide | EtOH—ethanol |

-continued

| | |
|---|---|
| ${}^i$Pr—isopropyl | ${}^t$Bu—tert-butyl |
| BINAP—2,2'-bis(diphenylphosphino)-1,1'-binaphthyl | |
| DIPEA—N,N-diisopropylethylamine | $SiO_2$—silica |
| TMEDA—N,N,N',N'-tetramethylethylenediamine | |
| HBTU—O-(benzotriazol-1-yl)-N,N,N',N'-tetramethyluronium hexafluorophosphate | |
| r.t.—room temperature | RT—retention time |
| conc.—concentrated | sat.—saturated |
| h—hour | br—broad |
| HPLC—High Performance Liquid Chromatography | |
| LCMS—Liquid Chromatography Mass Spectrometry | |
| ES+—Electrospray Positive Ionisation | |

Analytical Conditions

All NMRs were obtained either at 300 MHz or 400 MHz.

Compounds were named with the aid of ACD Labs Name (v. 7.0) supplied by Advanced Chemical Development, Toronto, Canada.

Chiral purity was determined by HPLC using a CHIRALPAK AD 250*4.6 mm 10 μm column; mobile phase 40% IPA, 60% heptane; flow rate 1.0 ml/min; column temperature 40° C.

Examples 85-141 were prepared as a library and final purities were determined by LCMS using a Luna C18, 4.6 mm, 5 μm column: mobile phase A: 99.9% water, 0.1% formic acid; mobile phase B; 99.9% MeCN, 0.1% formic acid. Gradient program (flow rate 6.5 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Preparative LC was performed at pH 3.2 using a Luna C18, 21.2 mm, 5 μm column: mobile phase A: 90% water, 10% MeCN, 0.1% formic acid; mobile phase B: 90% MeCN, 10% water, 0.1% formic acid.

Gradient program for pH 3.2 method (flow rate 20 mL/min, column temperature 35° C.):

| Time | A % | B % |
|---|---|---|
| 0.00 | 95.0 | 5.0 |
| 11.00 | 5.0 | 95.0 |
| 11.50 | 95.0 | 5.0 |
| 12.00 | 95.0 | 5.0 |

All reactions involving air- or moisture-sensitive reagents were performed under a nitrogen atmosphere using dried solvents and glassware.

Intermediate 1

Method A

2-Bromocyclohexane-1,3-dione

To a stirred solution of cyclohexane-1,3-dione (1.12 g, 10 mmol) in AcOH (20 mL) at r.t. was added bromine (1.6 g, 0.51 mL, 10 mmol) dropwise. The reaction mixture was stirred for 2 h and then the product was isolated by filtration. The precipitate was washed twice with $Et_2O$ (100 mL) and then dried in vacuo to give the title compound in quantitative yield as a buff solid, which was used without further purification. LCMS (ES+) 190.9 $(M+H)^+$.

Intermediate 2

2-Bromo-5,5-dimethylcyclohexane-1,3-dione

To a stirred solution of 5,5-dimethylcyclohexane-1,3-dione (1.4 g, 10 mmol) in AcOH (20 mL) at r.t. was added bromine (1.6 g, 0.51 mL, 10 mmol) dropwise. The reaction was carried out according to Method A to give the title compound in quantitative yield as a light brown solid, which was used without further purification. LCMS (ES+) 218.9 $(M+H)^+$.

Intermediate 3

2-Bromo-5-isopropylcyclohexane-1,3-dione

To a stirred solution of 5-isopropylcyclohexane-1,3-dione (2 g, 12.9 mmol) in AcOH (20 mL) at r.t. was added bromine (2.06 g, 0.66 mL, 12.9 mmol) dropwise. The reaction was then carried out according to Method A to give the title compound (2.91 g, 96%) as a white solid. $\delta_H$ (DMSO-$d_6$) 2.55-2.48 (4H, m), 2.38-2.32 (1H, m), 1.91-1.82 (1H, m), 1.79-1.54 (1H, m), 0.87 (6H, d, J 6.7 Hz). LCMS (ES+) 234.9 $(M+H)^+$.

Intermediate 4

2-Bromo-5-propylcyclohexane-1,3-dione

To a stirred solution of 5-propylcyclohexane-1,3-dione (1.54 g, 10 mmol) in AcOH (20 mL) at r.t. was added bromine (1.6 g, 0.51 mL, 1 mmol) dropwise. The reaction was carried out according to Method A to give the title compound in quantitative yield as a light brown solid, which was used without further purification. LCMS (ES+) 232.9 $(M+H)^+$.

Intermediate 5

2-Bromo-5-phenylcyclohexane-1,3-dione

To a stirred solution of 5-phenylcyclohexane-1,3-dione (1.88 g, 10 mmol) in AcOH (20 mL) at r.t. was added bromine (1.6 g, 0.51 mL, 10 mmol) dropwise. The reaction was carried out according to Method A to give the title compound in quantitative yield as a light brown solid, which was used without further purification. LCMS (ES+) 266.8 $(M+H)^+$.

Intermediate 6

2-Bromo-5-(4-chlorophenyl)cyclohexane-1,3-dione

To a stirred solution of 5-(4-chlorophenyl)cyclohexane-1,3-dione (5 g, 22.6 mmol) in AcOH (40 mL) was added bromine (3.61 g, 1.15 mL, 22.6 mmol) dropwise. The reaction was then carried out according to Method A to give the title compound (2.0 g, 66%) as a white solid. $\delta_H$ (DMSO-$d_6$) 7.38 (4H, m), 3.41-3.38 (1H, m), 2.97-2.85 (2H, m), 2.67 (2H, dd, J 16.4 and 4.2 Hz), 2.50 (1H, bs).

Intermediate 7

2-Bromo-4,4-dimethylcyclohexane-1,3-dione

To a stirred solution of 4,4-dimethylcyclohexane-1,3-dione (1.4 g, 10 mmol) in AcOH (20 mL) at r.t. was added bromine (1.6 g, 0.51 mL, 10 mmol) dropwise. The reaction was carried out according to Method A to give the title compound in quantitative yield as a light brown solid which was used without further purification. LCMS (ES+) 218.9 (+H)$^+$.

Intermediate 8

2-Bromo-5-methylcyclohexane-1,3-dione

To a stirred solution of 5-methylcyclohexane-1,3-dione (1.26 g, 10 mmol) in AcOH (20 mL) at r.t. was added bromine (1.6 g, 0.51 mL, 10 mmol) dropwise. The reaction was carried out according to Method A to give the title compound in quantitative yield as a light brown solid which was used without further purification. LCMS (ES+) 204.9 (M+H)$^+$.

Intermediate 9

2-Bromo-5-(4-methoxyphenyl)cyclohexane-1,3-dione

To a stirred solution of 5-(4-methoxyphenyl)cyclohexane-1,3-dione (5 g, 22.6 mmol) in AcOH (40 mL) at r.t. was added bromine (3.61 g, 1.18 mL, 22.6 mmol) dropwise. The reaction was then carried out according to Method A to give the title compound in quantitative yield as a white solid. $\delta_H$ (DMSO-$d_6$) 7.24 (2H, d, J 8.6 Hz), 6.87 (2H, d, J 8.6 Hz), 3.72 (3H, s), 3.31-3.21 (1H, m), 2.88-2.82 (2H, m), 2.77-2.62 (3H, m). LCMS (ES+) 296.9 (M+H)$^+$.

Intermediate 10

2-Bromo-5-[4-(methylthio)phenyl]cyclohexane-1,3-dione

To a stirred solution of 5-[4-(methylthio)phenyl]cyclohexane-1,3-dione (1.08 g, 4.6 mmol) in AcOH (10 mL) at r.t. was added bromine (0.74 g, 0.23 mL, 4.6 mmol) dropwise. The reaction was then carried out according to Method A to give the title compound (1.03 g, 70%) as a white solid. LCMS (ES+) 314.9 (M+H)$^+$.

Intermediate 11

2-Bromo-5-(2-furyl)cyclohexane-1,3-dione

To a stirred solution of 5-(2-furyl)cyclohexane-1,3-dione (1 g, 5.6 mmol) in THF (50 mL) was added N-bromosuccinimide (1 g, 5.6 mmol). The reaction mixture was heated to 85° C. for 12 h and on completion was filtered. The filtrate was concentrated in vacuo to give the title compound (1.0 g, 69%) as a white solid. LCMS (ES+) 256.8 (M+H)$^+$.

Intermediate 12

3-Bromospiro[5,5]undecane-2,4-dione

To a stirred solution of spiro[5,5]undecane-2,4-dione (1.29 g, 5 mmol) in AcOH (10 mL) at r.t. was added bromine (0.8 g, 0.25 ml, 5 mmol) dropwise. The reaction was carried out according to Method A to give the title compound in quantitative yield as a light brown solid which was used without further purification. LCMS (ES+) 258.9 (M+H)$^+$.

Intermediate 13

Morpholine-4-carbothioamide

To a stirred solution of 1,1'-thiocarbonyldiimidazole (10.0 g, 56.1 mmol) in THF (150 mL) was added morpholine (4.24 g, 4.2 mL, 48.7 mmol). The reaction was stirred for 72 h at r.t. and then concentrated in vacuo to 30 mL. Ammonia (60 mL, 2.0M in MeOH) was added to the reaction mixture, which was then stirred at r.t. in a sealed flask overnight. The reaction mixture was filtered and the solid washed with Et$_2$O to give the title compound (2.0 g, 28%) as a white solid. $\delta_H$ (DMSO-$d_6$) 7.46 (2H, bs), 3.80-3.60 (4H, m), 3.60-3.50 (4H, m).

Intermediate 14

2-Amino-5,5-dimethyl-5,6-dihydro-1,3-benzothiazol-7(4H)-one

To a stirred solution of Intermediate 2 (12 g, 60 mmol) in THF (200 mL) was added thiourea (4.2 g, 60 mmol) and N,N-diisopropylethylamine (7.76 g, 10.45 mL, 60 mmol). The reaction was carried out according to Method B to yield the title compound (8.6 g, 73%) as a yellow solid. $\delta_H$ (DMSO-$d_6$) 8.07 (2H, s), 2.59 (2H, s), 2.27 (2H, s), 1.05 (6H, s). LCMS (ES+) 197.0 (M+H)$^+$.

Intermediate 15

Method C

2-Bromo-5,5-dimethyl-5,6-dihydro-1,3-benzothiazol-7(4H)-one

To a stirred solution of Intermediate 14 (7 g, 36 mmol) in MeCN (150 mL) was added copper(II) bromide (8.7 g, 39 mmol) and tert-butyl nitrite (5.1 g, 49 mmol). After stirring at r.t. for 2 h, the reaction mixture was poured into 10% HCl (100 mL) and extracted with DCM (2×150 mL). The organic fraction was dried over MgSO$_4$ and concentrated in vacuo to give the title compound (7.0 g, 74%) as an orange solid. $\delta_H$ (CDCl$_3$) 2.84 (2H, s), 2.41 (2H, s), 1.07 (6H, s). LCMS (ES+) 260.0 (4+H)$^+$.

Intermediate 16

Method D (2R)-2-Amino-3-(1H-indol-3-yl-propan-1-ol

To a solution of (R)-tryptophan (4.0 g, 20 mmol) in THF (100 mL) at 0° C. was slowly added borane-dimethylsulphide complex (5.9 mL, 10M solution in THF, 59 mmol). The reaction mixture was heated to 70° C. for 16 h and the excess borane was quenched by the addition of methanol (10 mL) at 0° C. The reaction mixture was concentrated, and the residue dissolved in EtOAc (120 mL) and washed with 20% NaOH solution (2×70 mL). The organic layer was then extracted into aqueous 2M HCl (2×100 mL). The combined acidic aqueous layers were then basified to pH 14 (addition of solid NaOH) and were re-extracted with EtOAc (2×150 mL). The combined organic fractions were washed with brine (70 mL), dried over MgSO$_4$ and concentrated in vacuo to give the title compound (3.5 g, 92%) as a white solid. δ$_H$ (MeOD-d$_3$) 7.46 (1H, d, J 7.9 Hz), 7.21 (1H, d, J 8.0 Hz), 6.96 (3H, m), 3.79 (1H, dd, J 11.3 and 3.6 Hz), 3.54 (1H, dd, J 11.2 and 6.2 Hz), 3.05 (1H, m), 2.80 (1H, m), 2.61 (1H, m). Note: exchangeable protons not evident in MeOD.

Intermediate 17

Method E

2-Chloro-N-[(1R)-2-hydroxy-1-(1H-indol-3-ylm-ethyl)ethyl]acetamide

To a stirred solution of Intermediate 16 (2 g, 10 mmol) and triethylamine (1.32 g, 1.8 mL, 13 mmol) in THF (120 ml) at 0° C. was added chloroacetyl chloride (1.36 g, 0.92 mL, 12 mmol) dropwise. The reaction mixture was then stirred at r.t. for 1.5 h before being quenched by the addition of water (5 mL). The reaction mixture was diluted with EtOAc (120 mL) and partitioned with water (100 mL). The organic fraction was washed with brine (100 mL), dried over MgSO$_4$ and concentrated in vacuo to give the title compound (2.4 g, 90%) as a solid. δ$_H$(CDCl$_3$) 8.15 (1H, s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.9 Hz), 3.59 (2H, m), 2.98 (2H, d, J 6.0 Hz), 2.52 (1H, br. s).

Intermediate 18

Method F (5R)-5-(1H-Indol-3-ylmethyl)morpholin-3-one

To a stirred solution of Intermediate 17 (2.4 g, 9.5 mmol) in THF (100 mL) at 0° C. was added sodium hydride (0.8 g, 60% dispersion in oil, 19 mmol) portionwise. The reaction mixture was then stirred at r.t. for 1.5 h before quenching by the addition of ice. The reaction mixture was then partitioned between EtOAc (100 mL) and water (100 mL) and the organic fraction was dried over MgSO$_4$ and concentrated in vacuo to give the title compound (1.8 g, 82%) as a solid. δ$_H$ (MeOD-d$_3$) 7.46 (1H, d, J 7.8 Hz), 7.25 (1H, d, J 7.8 Hz), 6.95 (3H, m), 3.99 (2H, s), 3.65 (2H, m), 3.52 (1H, m), 2.91 (2H, d, J 6.3 Hz). Exchangeable protons were not observed. LCMS (ES+) 231.0 (M+H)$^+$.

Intermediate 19

Method G

3-[(3R)-Morpholin-3-ylmethyl]-1H-indole

To a stirred solution of Intermediate 18 (1.8 g, 7.8 mmol) in THF (100 mL) was added, at 0° C., LiAlH$_4$ (1 g, 27 mmol). After stirring overnight at r.t. the reaction mixture was quenched by dropwise addition of Na$_2$CO$_3$ solution (20 mL). The resulting mixture was filtered through Celite® and the filtrate was concentrated in vacuo. The resulting solid was dissolved in PhMe and the solvent removed by evaporation in vacuo. Column chromatography (SiO$_2$, EtOAc-hexane) yielded the title compound (1.5 g, 89%) as a solid. δ$_H$(CDCl$_3$) 8.11 (1H, s), 7.55 (1H, d, J 7.8 Hz), 7.28 (1H, d, J 8.0 Hz), 7.11 (4H, m), 3.83 (1H, dd, J 10.9 and 2.8 Hz), 3.71 (1H, dt, J 11.1 and 2.2 Hz), 3.47 (1H, m), 3.24 (1H, t, J 9.8 Hz), 3.06 (1H, m), 2.78 (3H, m), 2.56 (1H, m), 1.92 (1H, br. s). LCMS (ES+) 217.0 (M+H)$^+$.

Intermediate 20

2-Amino-3-(2-naphthyl)propan-1-ol

The title compound was prepared from 3-(2-naphthyl)ala-nine according to Method D and was isolated as a solid in 89% yield. δ$_H$(CDCl$_3$) 7.68 (3H, d, J 8.9 Hz), 7.49 (1H, m), 7.31 (2H, m), 7.18 (1H, dd, J 8.5 and 1.5 Hz), 3.50 (2H, m), 3.32 (1H, m), 3.05 (1H, m), 2.79 (3H, m), 2.52 (1H, m).

Intermediate 21

2-Chloro-N-[2-hydroxy-1-(2-naphthylmethyl)ethyl]acetamide

The title compound was prepared from Intermediate 20 according to Method E and was isolated as an oil in 72% yield. δ$_H$ (CDCl$_3$) 7.75 (3H, m), 7.61 (1H, s), 7.35 (2H, m), 7.29 (1H, m), 6.82 (1H, bs), 4.21 (1H, m), 3.93 (2H, d, J 5.1 Hz), 3.61 (2H, m), 2.99 (2H, dd, J 7.3 and 1.7 Hz), 2.34 (1H, bs). LCMS (ES+) 277.9 (M+H)$^+$.

Intermediate 22

5-(2-Naphthylmethyl)morpholin-3-one

The title compound was prepared from Intermediate 21 according to Method E and was isolated as an oil in 53% yield. δ$_H$ (CDCl$_3$) 7.72 (3H, m), 7.56 (1H, s), 7.36 (2H, m), 7.17 (1H, m), 6.83 (1H, bs), 4.07 (2H, s), 3.75 (1H, m), 3.54 (1H, m), 2.98 (1H, m), 2.81 (2H, m). LCMS (ES+) 242.0 (M+H)$^+$.

Intermediate 23

3-(2-Naphthylmethyl)morpholine

The title compound was prepared from Intermediate 22 according to Method G and was isolated as a solid in 74% yield after purification by column chromatography (SiO$_2$, EtOAc). δ$_H$ (CDCl$_3$) 7.71 (3H, m), 7.57 (1H, s), 7.36 (2H, m), 7.25 (1H, dd, J 8.4 and 1.7 Hz), 3.79 (1H, dd, J 10.9 and 2.9 Hz), 3.70 (1H, dt, J 11.3 and 2.4 Hz), 3.47 (1H, m), 3.25 (1H, m), 3.04 (1H, m), 2.75 (3H, m), 2.56 (1H, m), 1.82 (1H, bs).

Intermediate 24

2-Amino-3-(1-naphtlyl)propan-1-ol

The title compound was prepared from 3-(1-naphthyl)ala-nine according to Method D and was isolated as a solid in 89% yield. δ$_H$ (CDCl$_3$) 7.94 (1H, d, J 7.1 Hz), 7.75 (1H, dd, J 7.0 and 2.5 Hz), 7.65 (1H, d, J 8.0 Hz), 7.42 (2H, m), 7.31 (2H, m), 3.55 (2H, m), 3.37 (1H, m), 3.23 (1H, m), 2.83 (1H, m), 2.65 (3H, bs).

Intermediate 25

2-Chloro-N-[2-hydroxy-1-(1-naphthylmethyl ethyl]acetamide

The title compound was prepared from Intermediate 24 according to Method E and was isolated as an oil in 92% yield. δ$_H$ (CDCl$_3$) 8.16 (1H, d, J 8.5 Hz), 7.79 (1H, dd, J 8.0 and 1.7 Hz), 7.69 (1H, d, J 7.8 Hz), 7.45 (2H, m), 7.30 (2H, m), 6.88 (1H, bs), 4.27 (1H, m), 3.94 (2H, d, J 4.2 Hz), 3.61 (2H, m), 3.30 (2H, m), 2.10 (1H, bs). LCMS (ES+) 278.0 (M+H)$^+$.

Intermediate 26

5-(1-Naphthylmethyl)morpholin-3-one

The title compound was prepared from Intermediate 25 according to Method F and was isolated as a yellow oil in 44% yield. $\delta_H$ (CDCl$_3$) 7.82 (1H, d, J 7.7 Hz), 7.72 (1H, d, J 7.3 Hz), 7.62 (1H, d, J 8.1 Hz), 7.12-7.42 (4H, m), 6.73 (1H, bs), 3.97 (2H, d, J 5.0 Hz), 3.63 (2H, m), 3.41 (1H, m), 3.11 (2H, m).

Intermediate 27

3-(1-Naphthylmethyl)morpholine

The title compound was prepared from Intermediate 26 according to Method G and was isolated as a yellow oil in 64% yield after purification by column chromatography (SiO$_2$, 9.5:1 EtOAc/MeOH). $\delta_H$ (CDCl$_3$) 8.04 (1H, d, J 8.0 Hz), 7.84 (1H, dd, J 7.6 and 2.3 Hz), 7.73 (1H, d, J 7.9 Hz), 7.32-7.54 (4H, m), 3.87 (1H, dd, J 10.5 and 2.2 Hz), 3.74 (1H, dt, J 11.0 and 2.4 Hz), 3.54 (1H, m), 3.35 (1H, ni), 3.14 (2H, m), 2.88 (1H, m), 2.71 (2H, m), 2.00 (1H, bs).

Intermediate 28

2-Amino-4-phenylbutan-1-ol

The title compound was prepared from 2-amino-4-phenylbutanoic acid according to Method D and was isolated as a solid in 94% yield. $\delta_H$ (CDCl$_3$) 7.21 (2H, m), 7.10 (3H, m), 3.53 (1H, dd, J 10.5 and 3.9 Hz), 3.24 (1H, m), 2.81 (1H, bs), 2.65 (2H, m), 2.17 (3H, bs), 1.49-1.76 (2H, m).

Intermediate 29

2-Chloro-N-[1-(hydroxymethyl)-3-phenylpropyl]acetamide

The title compound was prepared from Intermediate 28 according to Method E and was isolated as a solid in 87% yield. $\delta_H$ (CDCl$_3$) 7.24 (2H, m), 7.17 (3H, m), 6.59 (1H, bs), 3.97 (2H, d, J 0.8 Hz), 3.63 (2H, dq, J 11.1 and 3.8 Hz), 2.63 (2H, m), 1.86 (4H, m). LCMS 242.1 (M+H)$^+$.

Intermediate 30

5-(2-Phenethyl)morpholin-3-one

The title compound was prepared from Intermediate 29 according to Method F and was isolated as an oil in 51% yield. $\delta_H$ (CDCl$_3$) 6.95-7.09 (5H, m), 5.97 (1H, bs), 3.98 (3H, m), 3.65 (1H, m), 3.30 (1H, m), 2.44 (2H, m), 1.71 (2H, m). LCMS 206.0 (M+H)$^+$.

Intermediate 31

3-(2-Phenethyl)morpholine

The title compound was prepared from Intermediate 30 according to Method G and was isolated as an oil in 71% yield. $\delta_H$(CDCl$_3$) 7.21-7.32 (5H, m), 3.84 (2H, m), 3.52 (1H, dt, J 10.6 and 3.3 Hz), 3.20 (1H, t, J 9.9 Hz), 2.94 (3H, m), 2.66 (2H, m), 1.76 (3H, m).

Intermediate 32

N-[(1S)-1-Benzyl-2-hydroxyethyl]-2-chloroacetamide

The title compound was prepared from (2S)-2-amino-3-phenylpropan-1-ol according to Method E and was isolated as an oil in 86% yield. $\delta_H$ (CDCl$_3$) 7.13 (5H, m), 6.92 (1H, bd, J 8.2 Hz), 4.13 (1H, m), 3.85 (2H, d, J 4.3 Hz), 3.51 (3H, m), 2.80 (2H, m).

Intermediate 33

(5S)-5-Benzylmorpholin-3-one

The title compound was prepared from Intermediate 32 according to Method F and was isolated as an oil in 69% yield. $\delta_H$(CDCl$_3$) 7.27 (4H, m), 7.13 (1H, d, J 6.5 Hz), 5.86 (1H, bs), 4.10 (2H, d, J 2.2 Hz), 3.84 (1H, m), 3.72 (1H, m), 3.48 (1H, m), 2.82 (1H, dd, J 13.5 and 5.6 Hz), 2.64 (1H, m).

Intermediate 34

(3S)-3-Benzylmorpholine

The title compound was prepared from Intermediate 33 according to Method G and was isolated as a colourless oil in 81% yield after purification by column chromatography (SiO$_2$, EtOAc). $\delta_H$ (CDCl$_3$) 7.13 (5H, m), 3.72 (2H, t, J 11.1 Hz), 3.47 (1H, m), 3.19 (1H, t, J 9.8 Hz), 2.94 (1H, m), 2.74 (2H, m), 2.57 (1H, m), 2.41 (1H, dd, J 13.3 and 9.0 Hz), 1.67 (1H, bs).

Intermediate 35

2-Chloro-N-[(1S,2R)-2-hydroxy-2,3-dihydro-1H-inden-1-yl]acetamide

The title compound was prepared from (1S,2R)-1-aminoindan-2-ol according to Method E and was isolated as an oil in 79% yield. $\delta_H$ (DMSO-d$_6$) 8.20 (1H, d, J 8.4 Hz), 7.24 (4H, m), 5.16 (2H, m), 4.45 (1H, m), 4.24 (2H, m), 3.07 (1H, dd, J 16.2 and 5.0 Hz), 2.82 (1H, dd, J 16.2 and 1.5 Hz).

Intermediate 36

(4aS,9aR)-4,4-a,9,9a-Tetrahydroindeno[2,1-b][1,4]oxazin-3(2H)-one

The title confound was prepared from Intermediate 35 according to Method F and was isolated as an oil in 49% yield. $\delta_H$ (CDCl$_3$) 8.42 (1H, bs), 7.36 (1H, m), 7.28 (3H, m), 4.77 (1H, m), 4.53 (1H, m), 4.17 (2H, m), 3.20 (1H, dd, J 4.7 and 16.8 Hz), 3.09 (1H, d, J 16.8 Hz).

Intermediate 37

(4aS,9aR)-2,3,4,4a,9,9a-Hexahydroindeno[2,1-b][1,4]oxazine

The title compound was prepared from Intermediate 36 according to Method G and was isolated as a colourless oil in 84% yield after purification by column chromatography (SiO$_2$, EtOAc). $\delta_H$ (CDCl$_3$) 7.39 (1H, m), 7.26 (3H, m), 4.34 (1H, m), 4.26 (1H, m), 3.68 (2H, m), 2.94 (3H, m), 2.70 (1H, m), 2.05 (1H, bs).

Intermediate 38

2-Chloro-N-[1-(4-chlorobenzyl)-2-hydroxyethyl]acetamide

The title compound was prepared from 2-amino-3-(4-chlorophenyl)propan-1-ol according to Method E and was isolated as an oil in 82% yield. $\delta_H$ (CDCl$_3$) 7.20 (2H, d, J 8.4 Hz), 7.08 (2H, d, J 8.4 Hz), 6.76 (1H, bd, J 7.3 Hz), 4.13 (1H, m), 3.93 (2H, d, J 3.0 Hz), 3.53 (2H, m), 2.81 (2H, m), 2.45 (1H, bs).

Intermediate 39

5-(4-Chlorobenzyl)morpholin-3-one

The title compound was prepared from Intermediate 38 according to Method F and was isolated as an oil in 53% yield. $\delta_H$ (CDCl$_3$) 6.85-7.17 (5H, m), 3.95 (2H, m), 3.21-3.62 (4H, m), 2.52 (1H, m).

Intermediate 40

3-(4-Chlorobenzyl)morpholine

The title compound was prepared from Intermediate 39 according to Method G and was isolated as a colourless solid in 62% yield after purification by column chromatography (SiO$_2$, EtOAc). $\delta_H$ (CDCl$_3$) 7.04-7.33 (2H, m), 7.05 (2H, m), 3.73 (2H, m), 3.49 (1H, m), 3.17 (1H, t, J 5.0 Hz), 2.91 (1H, m), 2.82 (2H, m), 2.55 (1H, m), 2.41 (1H, m), 1.75 (1H, bs).

Intermediate 41

2-Amino-3-(5-methyl-1H-indol-3-yl)propan-1-ol

The title compound was prepared from 5-methyltryptophan according to Method D and was isolated as an oil in 97% yield. $\delta_H$ (CDCl$_3$) 7.89 (1H, bs), 7.40 (1H, d, J 8.1 Hz), 7.08 (1H, s), 6.89 (2H, m), 3.60 (1H, dd, J 10.5 and 3.9 Hz), 3.33 (1H, dd, J 10.5 and 7.1 Hz), 3.18 (1H, m), 2.83 (1H, dd, J 14.3 and 8.4 Hz), 2.39 (3H, s), 1.81 (3H, bs).

Intermediate 42

2-Chloro-N-{2-hydroxy-1-[(5-methyl-1H-indol-3-yl)methyl]ethyl}acetamide

The title compound was prepared from Intermediate 41 according to Method E and was isolated as a solid in 77% yield. $\delta_H$ (CDCl$_3$) 7.86 (1H, bs), 7.47 (1H, d, J 8.0 Hz), 7.09 (1H, s), 6.93 (2H, m), 6.80 (1H, bs), 4.22 (1H, m), 3.94 (2H, d, J 2.6 Hz), 3.64 (2H, m), 2.98 (2H, d, J 6.8 Hz), 2.39 (3H, s), 1.67 (1H, bs).

Intermediate 43

5-[(5-Methyl-1H-indol-3-yl)methyl]morpholin-3-one

The title compound was prepared from Intermediate 42 according to Method F and was isolated as an oil in 57% yield. $\delta_H$ (DMSO-d$_6$) 10.60 (1H, bs), 8.02 (1H, bs), 7.51 (1H, m), 7.05 (2H, m), 6.79 (1H, m), 3.98 (2H, m), 3.61 (2H, m), 3.41 (1H, m), 2.72 (2H, m), 2.31 (3H, s).

Intermediate 44

5-Methyl-3-(morpholin-3-ylmethyl)-1H-indole

The title compound was prepared from Intermediate 43 according to Method G and was isolated as a colourless solid in 52% yield after purification by column chromatography (SiO$_2$, EtOAc). $\delta_H$ (CDCl$_3$) 7.97 (1H, bs), 7.53 (1H, d, J 8.1 Hz), 7.18 (1H, s), 6.99 (2H, m), 3.96 (1H, dd, J 11.4 and 2.9 Hz), 3.82 (1H, m), 3.71 (1H, m), 3.50 (1H, m), 3.26 (1H, m), 2.94 (4H, m), 2.48 (3H, s), 1.99 (1H, bs).

Intermediate 45

2-Amino-3-(1H-indol-3-yl)propan-1-ol

The title compound was prepared from tryptophan according to Method D and was isolated as a solid in 92% yield. $\delta_H$ (MeOD-d$_3$) 7.46 (1H, d, J 7.9 Hz), 7.21 (1H, d, J 8.0 Hz), 6.96 (3H, m), 3.79 (1H, dd, J 11.3 and 3.6 Hz), 3.54 (1H, dd, J 11.2 and 6.2 Hz), 3.05 (1H, m), 2.80 (1H, m), 2.61 (1H, m). Note: exchangeable protons not evident in MeOD.

Intermediate 46

2-Chloro-N-[2-hydroxy-1-(1H-indol-3-ylmethyl)ethyl]acetamide

The title compound was prepared from Intermediate 45 according to Method E and was isolated as a solid in 82% yield. $\delta_H$ (CDCl$_3$) 8.15 (1H, s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.3 Hz), 3.59 (2H, m), 2.98 (2H, d, J 6.0 Hz), 2.52 (1H, br. s).

Intermediate 47

5-(1H-Indol-3-ylmethyl)morpholin-3-one

The title compound was prepared from Intermediate 46 according to Method F and was isolated as a solid in 72% yield. $\delta_H$ (MeOD-d$_3$) 7.46 (1H, d, J 7.8 Hz), 7.25 (1H, d, J 8.0 Hz), 6.95 (3H, m), 3.99 (2H, s), 3.65 (2H, m), 3.52 (1H, m), 2.91 (2H, d, J 6.3 Hz). Exchangeable protons were not observed. LCMS (ES+) 231.0 (M+H)$^+$.

Intermediate 48

3-(Morpholin-3-ylmethyl)-1H-indole

The title compound was prepared from Intermediate 47 according to Method G and was isolated as a colourless solid in 69% yield after purification by column chromatography (SiO$_2$, EtOAc). $\delta_H$(CDCl$_3$) 8.11 (1H, s), 7.55 (1H, d, J 7.8 Hz), 7.28 (1H, d, J 8.0 Hz), 7.11 (4H, m), 3.83 (1H, dd, J 10.9 and 2.8 Hz), 3.71 (1H, d, J 11.1 and 2.2 Hz), 3.47 (1H, m), 3.24 (1H, t, J 9.8 Hz), 3.06 (1H, m), 2.78 (2H, m), 2.56 (1H, m), 1.92 (1H, br. s). LCMS (ES+) 217.0 (+H)$^+$.

Intermediate 49

(2S)-2-Amino-3-(1H-indol-3-yl)propan-1-ol

The title compound was prepared from (S)-tryptophan according to Method D and was isolated as a solid in 92% yield. $\delta_H$ (MeOD-d$_3$) 7.46 (1H, d, J 7.9 Hz), 7.21 (1H, d, J 8.0 Hz), 6.96 (3H, m), 3.79 (1H, dd, J 11.3 and 3.6 Hz), 3.54 (1H, dd, J 11.3 and 6.2 Hz), 3.05 (1H, m), 2.80 (1H, m), 2.61 (1H, m). Note: exchangeable protons not evident in MeOD.

Intermediate 50

2-Chloro-N-[(1S)-2-hydroxy-1-(1H-indol-3-ylmethyl)ethyl]acetamide

The title compound was prepared from Intermediate 49 according to Method E and was isolated as a solid in 84% yield. $\delta_H$ (CDCl$_3$) 8.15 (1H, s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.9 Hz), 3.59 (2H, m), 2.98 (2H, d, J 6.0 Hz), 2.52 (1H, br. s).

Intermediate 51

(5S)-5-(1H-Indol-3-ylmethyl)morpholin-3-one

The title compound was prepared from Intermediate 50 according to Method F and was isolated as a solid in 70% yield. $\delta_H$ (MeOD-d$_3$) 7.46 (1H, d, J 7.8 Hz), 7.25 (1H, d, J 8.0 Hz), 6.95 (3H, m), 3.99 (2H, s), 3.65 (2H, m), 3.52 (1H, m), 2.91 (2H, d, J 6.3 Hz). Exchangeable protons were not observed. LCMS (ES+) 231.0 (+H)$^+$.

Intermediate 52

3-[(3S)-Morpholin-3-ylmethyl]-1H-indole

The title compound was prepared from Intermediate 51 according to Method G and was isolated as a colourless solid in 67% yield after purification by column chromatography (SiO$_2$, EtOAc). $\delta_H$ (CDCl$_3$) 8.11 (1H, s), 7.55 (1H, d, J 7.8 Hz), 7.28 (1H, d, J 8.0 Hz), 7.11 (4H, m), 3.83 (1H, dd, J 10.9 and 2.8 Hz), 3.71 (1H, dt, J 11.1 and 2.2 Hz), 3.47 (1H, m), 3.24 (1H, t, J 9.8 Hz), 3.06 (1H, m), 2.78 (2H, m), 2.56 (1H, m), 1.92 (1H, br. s). LCMS (ES+) 217.0 (M+H)$^+$.

Intermediate 53

2-Amino-3-(4-bromophenyl)propan-1-ol

The title compound was prepared from 4-bromophenylalanine according to Method D and was isolated as a solid in 90% yield. $\delta_H$ (CDCl$_3$) 7.36 (2H, d, J 8.4 Hz), 7.00 (2H, d, J 8.4 Hz), 3.54 (1H, dd, J 10.7 and 4.1 Hz), 3.30 (1H, dd, J 10.7 and 6.9 Hz), 3.03 (1H, m), 2.67 (1H, dd, J 13.6 and 5.4 Hz), 2.43 (1H, dd, J 13.5 and 8.5 Hz). Exchangeable protons were not observed.

Intermediate 54

N-[1-(4-Bromobenzyl)-2-hydroxyethyl]-2-chloroacetamide

The title compound was prepared from Intermediate 53 according to Method E and was isolated as an oil in 79% yield. $\delta_H$ (CDCl$_3$) 7.36 (2H, d, J 8.4 Hz), 7.03 (2H, d, J 8.4 Hz), 6.73 (1H, bd, J 7.3 Hz), 4.10 (1H, m), 3.94 (2H, d, J 3.0 Hz), 3.56 (2H, dq, J 11.0 and 3.9 Hz), 2.81 (2H, m), 2.45 (1H, bs).

Intermediate 55

5-(4-Bromobenzyl)morpholin-3-one

The title compound was prepared from Intermediate 54 according to Method F and was isolated as an oil in 61% yield. $\delta_H$ (CDCl$_3$) 7.47 (2H, d, J 8.3 Hz), 7.07 (2H, d, J 8.3 Hz), 6.26 (1H, bs), 4.39 (1H, m), 4.09 (1H, m), 3.87 (1H, dd, J 11.7 and 3.6 Hz), 3.75 (1H, m), 3.56 (1H, dd, J 11.7 and 5.9 Hz), 2.84 (2H, m).

Intermediate 56

3-(4-Bromobenzyl)morpholine

The title compound was prepared from Intermediate 55 according to Method G and was isolated as a colourless solid in 63% yield after purification by column chromatography (SiO$_2$, EtOAc). $\delta_H$ (CDCl$_3$) 7.35 (2H, d, J 8.4 Hz), 7.00 (2H, d, J 8.4 Hz), 3.68 (2H, m), 3.44 (1H, m), 3.15 (1H, t, J 5.0 Hz), 2.94 (1H, m), 2.75 (2H, m), 2.54 (1H, m), 2.35 (1H, m), 1.95 (1H, bs).

Intermediate 57

Method W

N-Benzylserine

Racemic serine (14.7 g, 140 mmol) was dissolved in 2M NaOH (70 mL) and benzaldehyde (14.64 g, 14.0 mL, 138 mmol) added with stirring. The mixture was stirred at r.t. for 1 h before cooling to 5° C. Sodium borohydride (1.5 g, 40 mmol) was added portionwise such that an internal temperature of between 6 and 10° C. was maintained. After addition the reaction mixture was allowed to stir at 5° C. for 30 minutes and then at r.t. for 1 h. The reaction mixture was cooled to 5° C. and a further portion of sodium borohydride (1.5 g, 40 mmol) added portionwise such that an internal temperature <10° C. was maintained. The ice bath was removed on completion of addition and the reaction stirred at r.t. for 16 h. The reaction mixture was extracted with Et$_2$O (3×100 mL) and the aqueous phase acidified to pH 5 with concentrated hydrochloric acid. The resultant white precipitate was filtered and washed with water. The product was dried in vacuo to give the title compound (24.0 g, 88%). $\delta_H$ (DMSO-d$_6$) 7.45-7.30 (5H, m), 4.04-3.91 (2H, m), 3.70-3.61 (3H, m), 3.17 (1H, t, J 5.8 Hz). Some exchangeable protons were not observed.

Intermediate 58

Method X

4-Benzyl-5-oxomorpholine-3-carboxylic acid

To a solution of Intermediate 57 (35.0 g, 179 mmol) in NaOH solution (9.3 g in 200 mL) at 0° C. was slowly added chloroacetyl chloride (24.17 g, 17.0 mL, 214 mmol). The reaction mixture was allowed to warm to r.t. and stirred for 30 minutes. NaOH solution (30 wt %; 45 mL) was added and the reaction mixture heated to 38° C. for 4 h. The reaction mixture was cooled to 110° C. and acidified to pH 1 with concentrated HCl. On standing at 4° C. the product crystallised from the mixture and was collected by filtration, washed with cold water and then dried in vacuo to give the title compound (18.0 g, 43%). $\delta_H$ (DMSO-$d_6$) 13.50-12.50 (1H, bs), 7.38-7.25 (5H, m), 5.27 (1H, d, J 15.3 Hz), 4.24-4.10 (3H, m), 3.94-3.88 (2H, m), 3.83 (1H, d, J 15.3 Hz). LCMS (ES+) 236.0 (M+H)$^+$.

Intermediate 59

Method Y (4-Benzylmorpholin-3-yl)methanol

To a solution of Intermediate 58 (17.7 g, 75.3 mmol) in THF (300 mL) was added triethylamine (7.29 g, 10.0 mL, 72 mmol). The solution was cooled to 0° C. and borane dimethylsulphide complex (~10M in THF, 45 mL, 450 mmol) added slowly. The reaction mixture was heated at reflux for 16 h. The reaction mixture was cooled to 0° C. and the excess borane destroyed by slow addition of water. Excess THF was removed in vacuo and the residue made strongly alkaline with 2M NaOH solution (250 mL) and extracted with EtOAc (3×150 mL). The aqueous phase was acidified with concentrated HCl until pH 1, then extracted with EtOAc (3×200 mL). The combined organic fractions were washed with brine (150 mL), dried (MgSO$_4$) and concentrated in vacuo to give the title compound (13.5 g, 87%) as a clear oil. $\delta_H$ (CDCl$_3$) 7.29-7.16 (5H, m), 4.05 (1H, d, J 12.8 Hz), 3.88 (1H, dd, J 11.5 and 4.5 Hz), 3.78 (1H, m), 3.70-3.53 (2H, m), 3.51-3.40 (2H, m), 3.20 (1H, d, J 13.2 Hz), 2.68 (1H, dt, J 12.1 and 2.8 Hz), 2.48 (1H, m), 2.27 (1H, m), 2.20-2.15 (1H, bs).

Intermediate 60

Morpholin-3-ylmethanol

To a nitrogen-flushed solution of Intermediate 59 (10.0 g, 48.3 mmol) in MeOH (300 mL) was added palladium on carbon (10 wt %; 2 g) and the reaction mixture placed in a Parr® apparatus under 50 psi of hydrogen for 18 h. The resulting mixture was filtered through Celite® and concentrated in vacuo to give the title compound (5.2 g, 92%) as a clear oil. $\delta_H$ (CDCl$_3$) 3.81-3.76 (2H, m), 3.58-3.43 (3H, m), 3.35-3.28 (1H, m), 2.99-2.91 (5H, bm). LCMS (MS+) 118.0 (M+H)$^+$.

Intermediate 61

2-[3-(Hydroxymethyl)morpholin-4-yl]-5,5-dimethyl-5,6-dihydro-1,3-benzothiazol-7(4H)-one To a solution of Intermediate 15 (5.0 g, 19.3 mmol) in IPA (15 mL) was added N,N-diisopropylethylamine (6.67 g, 8.99 mL, 51.6 mmol) and Intermediate 60 (5.0 g, 42.7 mmol). The reaction mixture was heated at reflux for 18 h. The volatiles were removed in vacuo and the residue partitioned between EtOAc (300 mL) and brine (500 mL). The aqueous fraction was extracted with two further portions of EtOAc (200 mL) and the organic fractions combined, dried (MgSO$_4$), filtered and the solvents removed in vacuo. The crude residue was subjected to column chromatography (SiO$_2$, 1:1 to 1:0 EtOAc/hexanes) to give the title compound (4.28 g, 75%) as an orange foam. $\delta_H$ (DMSO-$d_6$) 5.02 (1H, t, J 5.8 Hz), 3.97 (1H, d, J 10.7 Hz), 3.90-3.70 (4H, m), 3.58-3.35 (4H, m), 2.64 (2H, s), 2.31 (2H, s), 1.05 (3H, s), 1.04 (3H, s). LCMS (MS+) 297.0 (M+H)$^+$.

Intermediate 62

4-(5,5-Dimethyl-7-oxo-4,5,6,7-tetrahydro-1,3-benzothiazol-2-yl)morpholine-3-carbaldehyde To a solution of oxalyl chloride (1.79 g, 1.23 mL, 14.125 mmol) in DCM (50 mL) at −78° C. was added DMSO (2.34 g, 2.13 mL, 30 mmol) and the resultant solution allowed to stir at −78° C. for 15 minutes. A solution of Intermediate 61 (3.7 g, 12.5 mmol) in DCM (150 mL) was added via cannula and the reaction mixture stirred at −78° C. for a further 2 h. Triethylamine (6.32 g, 8.71 mL, 62.5 mmol) was added and the mixture stirred at −78° C. for 30 minutes, warmed to r.t. and stirred for a further 1 h. The reaction mixture was concentrated by evaporation in vacuo and the residue partitioned between water (200 mL) and EtOAc (200 mL). The aqueous fraction was extracted with EtOAc (2×200 mL) and the combined organic fractions washed with brine (300 mL), dried (MgSO$_4$), filtered and the solvents removed in vacuo to give a crude yellow solid. The crude product was purified by column chromatography (SiO$_2$, 1:1 EtOAc/hexanes) to give the title compound (3.1 g, 84%) as a pale yellow solid. $\delta_H$ (CDCl$_3$) 9.71 (1H, s), 4.90 (1H, bs), 4.54 (1H, d, J 12.3 Hz), 4.00 (1H, d, J 10.8 Hz), 3.86 (1H, dd, J 12.1 and 4.1 Hz), 3.75-3.55 (3H, m), 2.68 (2H, s), 2.41 (2H, s), 1.14 (3H, s), 1.13 (3H, s). LCMS (MS+) 313.0 (M+H)$^+$ for the hemi-acetal (aldehyde plus H$_2$O); 295.0 (M+H)$^+$ for the aldehyde.

Intermediate 63

Method J (7E,Z)-2-Bromo-5,5-dimethyl-5,6-dihydro-1,3-benzothiazol-7(4H)-one oxime To a stirred solution of Intermediate 15 (0.50 g, 1.92 mmol) in pyridine (5 mL) was added 4 Å molecular sieves (3 pellets) and hydroxylamine hydrochloride (0.66 g, 9.54 mmol). The reaction mixture was stirred for 16 h then filtered. The filtrate was concentrated in vacuo and water (10 mL) was added to the residue. The solid obtained was filtered, washed with water (5×10 mL) and dried in vacuo to give the title compound (0.33 g, 62%) as a white solid consisting of a mixture of two regioisomers in ratio 1:15. $\delta_H$ (DMSO-$d_6$) 11.85 (1H, s, minor regioisomer), 11.82 (1H, s, major regioisomer), 2.76 (2H, s, major regioisomer), 2.74 (2H, s, minor regioisomer), 2.41 (2H, s), 1.01 (6H, s). LCMS (ES+) 275.0 (M+H)$^+$.

Intermediate 64

4-(5,5-Dimethyl-7-oxo-4,5,6,7-tetrahydro-1,3-benzothiazol-2-yl)-morpholine-3-carboxylic acid To a stirred solution of Intermediate 62 (0.60 g, 2.04 mmol) in 1,4-dioxane (15 mL) was added a sat. aqueous solution of KMnO$_4$ in aqueous 2M NaOH (15 mL) and the resultant mixture allowed to stir at r.t. for 16 h. The reaction mixture was then filtered through Celite® to remove MnO$_2$ and concentrated by evaporation in vacuo. The crude residue was dissolved in aqueous 10% NaOH solution (200 mL) and washed with EtOAc (3×100 mL). The aqueous fraction was acidified to pH 3 with concentrated HCl and extracted with EtOAc (3×150 mL). The combined organic fractions were washed with brine (200 mL), dried (MgSO$_4$) and filtered. The solvents were removed in vacuo to give the title compound as a gum (0.55 g, 87%). $\delta_H$ (DMSO-$d_6$) 13.00-12.00 (1H, br. s), 4.73 (1H, br. s), 4.26 (1H, d, J 11.9 Hz), 3.94 (1H, d, J 11.5

Hz), 3.77 (1H, dd, J 11.8 and 3.8 Hz), 3.65-3.47 (3H, m), 2.66 (2H, d, J 2.0 Hz), 2.33 (2H, d, J 4.1 Hz), 1.05 (3H, s), 1.03 (3H, s). LCMS (ES+) 311.0 (M+H)$^+$ Intermediate 65

3-Bromo-L-phenylalanine (2S)-3-(3-Bromophenyl)-2-(tert-butoxycarbonylamino) propionic acid (5.0 g, 14.5 mmol) was suspended in 4M HCl in 1,4-dioxane (75 mL) and stirred for 16 h at r.t. The white precipitate was filtered and washed with Et$_2$O to give the title compound as a white solid (3.2 g, 89%) that required no farther purification. $\delta_H$(CDCl$_3$) 8.32 (2H, s), 7.50-7.48 (2H, m), 7.34-7.29 (2H, m), 4.22 (1H, t, J 6.2 Hz), 3.13-3.11 (2H, m). An exchangeable proton was not observed.

Intermediate 66

(2S)-2-Amino-3-(3-bromophenyl)propan-1-ol

The title compound was prepared from Intermediate 65 according to Method D and was isolated as a colourless oil (56%) that required no further purification. $\delta_H$(CDCl$_3$) 7.42-7.35 (2H, m), 7.29-7.19 (2H, m), 3.59 (1H, m), 3.39 (1H, m), 3.10 (1H, m), 2.78 (1H, dd, J 13.5 and 5.3 Hz), 2.51 (1H, dd, J 13.5 and 8.5 Hz). Exchangeable protons were not observed.

Intermediate 67

N-[(1S)-1-(3-Bromobenzyl)-2-hydroxyethyl]-2-chloroacetamide

The title compound was prepared from Intermediate 66 according to Method E and was isolated as a yellow oil (77%) after purification by column chromatography (SiO$_2$, 1:1 EtOAc/DCM). $\delta_H$ (DMSO-d$_6$) 8.06 (1H, d, J 8.4 Hz), 7.42 (1H, s), 7.39-7.35 (1H, m), 7.26-7.19 (2H, m), 4.85 (1H, t, J 5.6 Hz), 3.98 (2H, s), 3.87 (1H, m), 3.39-3.15 (2H, m), 2.84 (1H, dd, J 13.7 and 5.4 Hz), 2.65 (1H, dd, J 13.7 and 8.6 Hz).

Intermediate 68

(5S)-5-(3-Bromobenzyl)morpholin-3-one

The title compound was prepared from Intermediate 67 according to Method F and was isolated as a white solid (50%) after purification by column chromatography (SiO$_2$, 1:1 EtOAc/DCM). $\delta_H$ (CDCl$_3$) 7.36-7.32 (1H, m), 7.28 (1H, s), 7.19-7.11 (1H, m), 7.06-7.03 (1H, m), 6.26 (1H, br. s), 4.09 (2H, s), 3.81 (1H, dd, J 11.7 and 3.6 Hz), 3.71-3.62 (1H, m), 3.50 (1H, dd, J 11.6 and 6.0 Hz), 2.79 (1H, dd, J 13.6 and 6.1 Hz), 2.67 (1H, dd, J 13.6 and 8.2 Hz). LCMS (ES+) 270.0 and 272.0 (M+H)$^+$.

Intermediate 69

(3S)-3-(3-Bromobenzyl)morpholine

To a stirred solution of Intermediate 68 (0.8 g, 3.0 mmol) in THF (100 mL) at 0° C. was added, under nitrogen, BH$_3$.Me$_2$S complex (1.7 mL, 10M solution in THF, 17.7 mmol) dropwise. The reaction was then carried out according to Method D to give the title compound as a clear oil (0.7 g, 83%). LCMS (ES+) 256.0 and 258.0 (M+H)$^+$.

Intermediate 70

2-Amino-7,7-dimethyl-5,6,7,8-tetrahydro-4H-[1,3]thiazolo[5,4-c]azepin-4-one

To a stirred solution of Intermediate 14 (26.7 g, 100.0 mmol) in CHCl$_3$ (900 mL) was added concentrated H$_2$SO$_4$ (86 mL). NaN$_3$ (9.8 g, 200.0 mmol) was added portionwise over 2 h and the apparatus was fitted with a bubbler to monitor gas formation. The reaction mixture was then stirred for 48 h at r.t., after which time the solvent was decanted off and ice was added to the resulting oil. A solution of sat. aqueous Na$_2$CO$_3$ was added slowly until a pH of 9 was reached. The resulting brown solid was filtered and washed several times with water and Et$_2$O to give the title compound as a light brown solid (18.5 g, 63%) that was used crude. $\delta_H$ (DMSO-d$_6$) 7.55 (1H, t, J 4.9 Hz), 7.34 (2H, s), 2.91 (2H, d, J 5.1 Hz), 0.96 (6H, s). Some exchangeable protons were not observed. LCMS (ES+) 211.0 (M+H)$^+$.

Intermediate 71

2-Bromo-7,7-dimethyl-5,6,7,8-tetrahydro-4H-[1,3]thiazolo[5,4-c]azepin-4-one

The title compound was prepared from Intermediate 70 according to Method C and was isolated as a yellow solid (84%) that required no further purification. $\delta_H$ (DMSO-d$_6$) 8.29 (1H, br. s), 2.98 (2H, d, J 5.2 Hz), 2.89 (s, 2H), 0.99 (s, 6H). LCMS (ES+) 277.0 and 275.0 (M+H)$^+$.

Intermediate 72

4-Benzyl-3-(iodomethyl)morpholine

A solution of Intermediate 59 (0.10 g, 0.49 mmol), PPh$_3$ (0.10 g, 0.49 mmol) and imidazole (0.03 g, 0.49 mmol) in DCM (5 mL) was stirred at 0° C. for 5 minutes. I$_2$ (0.12 g, 0.47 mmol) was added portionwise and stirring was continued at 0° C. for 2.5 h. The reaction mixture was then concentrated in vacuo and purified by column chromatography (SiO$_2$, 7:3 hexanes/EtOAc) to give the title compound as a white solid (0.12 g, 77%). $\delta_H$ (CDCl$_3$) 7.53-7.17 (5H, m), 3.85 (1H, d, J 13.1 Hz), 3.72 (2H, m), 3.61 (2H, m), 3.35 (1H, m), 3.24 (2H, m), 2.59 (1H, m), 2.34 (1H, m), 2.21 (1H, m). LCMS (ES+) 317.9 (M+H)$^+$.

Intermediate 73

N-(4-Methoxybenzyl)-D-serine

The title compound was prepared from D-serine (29.6 g, 0.3 mmol) and p-methoxybenzaldehyde (68.0 mL, 0.6 mmol) according to Method W and was obtained as a white solid (36.2 g, 57%) that required no further purification. $\delta_H$ (DMSO-d$_6$) 7.37 (2H, dd, J 8.7 and 1.9 Hz), 6.93 (2H, dd, J 8.7 and 1.9 Hz), 3.99 (2H, s), 3.55 (3H, s), 3.73 (3H, m), 3.15 (1H, t, J 4.7 Hz). Some exchangeable protons were not observed. LCMS (ES+) 225.8 (M+H)$^+$.

Intermediate 74

(3R)-4-(4-Methoxybenzyl)-5-oxomorpholine-3-carboxylic acid

The title compound was prepared from Intermediate 73 (35.0 g, 159.0 mmol) according to Method X and was isolated as a white solid (17.0 g, 41%) that required no further purification. $\delta_H$ (DMSO-d$_6$) 7.20 (2H, d, J 8.6 Hz), 6.89 (2H, d, J 8.6 Hz), 5.19 (1H, d, J 15.5 Hz), 4.14-4.04 (3H, m), 3.88 (1H, m), 3.85 (1H, m), 3.83 (3H, s), 3.73 (1H, d, J 15.3 Hz). Exchangeable proton was not observed. LCMS (ES+) 266.2 (M+H)$^+$.

Intermediate 75

[(3S)-4-(4-Methoxybenzyl)morpholin-3-yl]methanol

The title compound was prepared from Intermediate 74 (17.7 g, 67.0 mmol) according to Method Y and was isolated as a white solid (14.0 g, 88%) that required no further purification. $\delta_H$ (CDCl$_3$) 7.25 (2H, d, J 8.6 Hz), 6.88 (2H, d, J 8.6 Hz), 4.12 (1H, d, J 13.1 Hz), 3.98 (1H, dd, J 11.5 and 4.4 Hz), 3.84 (1H, dd, J 11.6 and 3.9 Hz), 3.82 (3H, s), 3.75 (2H, m), 3.58 (2H, m), 3.26 (1H, d, J 13.1 Hz), 2.75 (1H, m), 2.57 (1H, br. m), 2.35 (1H, m). Exchangeable proton was not observed.

Intermediate 76

2-Amino-3-(1H-pyrrolo[2,3-b]pyridin-3-yl)propan-1-ol

To a stirred solution of 3-(1H-pyrrolo[2,3-b]pyridin-3-yl) alanine monohydrate (10.0 g, 50.0 mmol) in THF (140 mL) at 0° C. was slowly added BF$_3$.Et$_2$O complex (7.0 mL, 60.0 mmol) followed by BH$_3$.Me$_2$S complex (10M in THF, 14.5 mL, 145.0 mmol). The reaction mixture was stirred at r.t. for 16 h and on completion the excess borane was quenched by the addition of MeOH (5 mL) at 0° C. The reaction mixture was concentrated, dissolved in EtOAc (120 mL) and washed with aqueous 20% NaOH solution (2×60 mL). The organic layer was then extracted into aqueous 2M HCl (2×150 mL). The combined acidic aqueous layers were then basified to pH 14 (addition of solid NaOH) and re-extracted with EtOAc (2×100 mL). The combined organic fractions were then dried over MgSO$_4$, filtered and concentrated in vacuo to give the title compound as a white solid (4.9 g, 52%). $\delta_H$ (MeOD-d$_3$) 12.13 (1H, br. s), 8.97 (1H, dd, J 4.7 and 1.5 Hz), 8.06 (1H, s), 7.82 (1H, m), 4.12 (1H, dd, J 10.3 and 4.9 Hz), 4.01 (1H, dd, J 10.3 and 6.5 Hz), 3.75 (1H, m), 3.59 (1H, dd, J 14.0 and 5.5 Hz), 3.37 (1H, dd, J 14.0 and 7.3 Hz). Exchangeable protons were not observed.

Intermediate 77

2-Chloro-N-[2-hydroxy-1-(1H-pyrrolo[2,3-b]pyridin-3-ylmethyl)ethyl]acetamide

To a stirred solution of Intermediate 76 (0.5 g, 2.6 mmol) in MeCN (9 mL) and MeOH (2 mL) at −10° C. was added NEt$_3$ (0.4 mL, 3.1 mmol) followed by chloroacetyl chloride (0.2 mL, 2.9 mmol) dropwise. The reaction mixture was allowed to warm to r.t. and stirred for 40 minutes. On completion, the reaction mixture was concentrated in vacuo and the resulting pink solid was triturated with water, filtered and dried to give the title compound as a white solid (0.5 g, 72%). $\delta_H$ (MeOD-d$_3$) 12.13 (1H, br. s), 8.97 (1H, dd, J 4.7 and 1.5 Hz), 8.93 (1H, d, J 8.2 Hz), 8.80 (1H, dd, J 7.8 and 1.3 Hz), 8.04 (1H, d, J 2.2 Hz), 7.83 (1H, dd, J 7.8 and 4.7 Hz), 5.65 (1H, t, J 5.6 Hz), 4.84 (2H, s), 4.76 (1H, m), 4.21 (2H, m), 3.73 (1H, dd, J 14.6 and 6.3 Hz), 3.59 (1H, dd, J 14.5 and 7.0 Hz). LCMS (ES+) 268.1 (M+H)$^+$.

Intermediate 78

5-(1H-Pyrrolo[2,3-b]pyridin-3-ylmethyl)morpholin-3-one

To a solution of potassium tert-butoxide (0.7 g, 2.2 mmol) in tert-amyl alcohol (4 mL) was added dropwise, at r.t., Intermediate 77 (0.4 g, 1.4 mmol) as a solution in tert-amyl alcohol (3 mL). The reaction mixture was stirred at r.t. for 16 h and was then concentrated in vacuo to give a white solid. To this was added Et$_2$O (2 mL) and water (2 mL) and the resultant solid was isolated by filtration and dried in vacuo to give the title compound as a white solid (0.3 g, 75%). $\delta_H$ (MeOD-d$_3$) 8.20 (1H, dd, J 4.8 and 1.5 Hz), 8.05 (1H, dd, J 7.8 and 1.5 Hz), 7.30 (1H, s), 7.11 (1H, dd, J 7.8 and 4.8 Hz), 4.10 (2H, s), 3.78 (2H, m), 3.64 (1H, m), 3.05 (2H, m). Exchangeable protons were not observed. LCMS (ES+) 232.1 (M+H)$^+$.

Intermediate 79

3-(Morpholin-3-ylmethyl)-1H-pyrrolo[2,3-b]pyridine

Sodium bis(2-methoxyethoxy)aluminium dihydride (3.2 mL, 10.4 mmol, 65% wt solution in toluene) was added dropwise to a solution of Intermediate 78 (0.5 g, 2.1 mmol) in THF (10 mL) at 0° C. The reaction mixture was allowed to warm to r.t. and stirred for a further 5 h before it was quenched by the addition of aqueous sat. NaHCO$_3$ solution at 0° C. The precipitate formed on quenching was removed by filtration through Celite® and the filtrate was concentrated in vacuo. The resulting dark oil was purified by column chromatography (SiO$_2$, 1:9 MeOH/EtOAc) to give the title compound as a white solid (0.2 g, 42%). $\delta_H$ (CDCl$_3$) 9.59 (1H, br. s), 8.24 (1H, dd, J 4.8 and 1.4 Hz), 7.94 (1H, dd, J 7.9 and 1.4 Hz), 7.21 (1H, s), 7.07 (1H, dd, J 7.9 and 4.8 Hz), 3.92 (1H, dd, J 11.1 and 2.9 Hz), 3.82 (1H, m), 3.61 (1H, m), 3.38 (1H, dd, J 9.8 and 1.2 Hz), 3.15 (1H, m), 2.95 (2H, m), 2.85 (1H, dd, J 14.4 and 4.9 Hz), 2.72 (1H, dd, J 14.4 and 8.9 Hz), 2.55 (1H, br. s). LCMS (ES+) 218.0 (M+H)$^+$.

Intermediate 80

(3R)-3-(Iodomethyl)-4-(4-methoxybenzyl)morpholine

A solution of Intermediate 75 (0.20 g, 0.97 mmol), PPh$_3$ (0.25 g, 0.97 mmol) and imidazole (0.07 g, 0.97 mmol) in DCM (9 mL) was stirred at 0° C. for 5 minutes. I$_2$ (0.25 g, 0.97 mmol) was added portionwise and stirring was continued at 0° C. for 2.5 h. The reaction mixture was then concentrated in vacuo and purified by column chromatography (SiO$_2$, 3:1 hexanes/EtOAc) to give the title compound as a white solid (0.22 g, 65%). $\delta_H$ (CDCl$_3$) 7.29 (2H, d, J 8.3 Hz), 6.89 (2H, d, J 8.3 Hz), 3.85 (1H, d, J 13.1 Hz), 3.82 (3H, s), 3.70 (2H, m), 3.59 (2H, m), 3.35 (1H, m), 3.24 (2H, m), 2.57 (1H, m), 2.35 (1H, m), 2.25 (1H, m).

Intermediate 81

(3R)-4-(4-Methoxybenzyl)-3-[(phenylthio)methyl]morpholine

To a stirred solution of thiophenol (0.07 mL, 0.71 mmol) in DMF (5 mL) was slowly added, at 0° C., NaH (0.03 g, 0.71 mmol, 60% dispersion in oil). The reaction mixture was allowed to stir at r.t. for 30 minutes before the temperature was lowered to 0° C. again and Intermediate 80 (0.24 g, 0.71 mmol) was added slowly. The reaction mixture was then stirred at r.t. for 1.5 h before it was quenched by the addition of ice. EtOAc (20 mL) was added and this was then washed with water (30 mL) and brine (25 mL), dried (MgSO$_4$), filtered and concentrated to give the title compound as a yellow oil (0.17 g, 52%) that was used crude. LCMS (ES+) 330.3 (M+H)$^+$.

Intermediate 82

(3R)-3-[(Phenylthio)methyl]morpholine

To a stirred solution of Intermediate 81 (0.17 g, 0.50 mmol) in MeCN (5 mL) and water (5 mL) was added Ce(NH$_3$)$_4$NO$_2$ (0.82 g, 1.50 mmol) and the reaction mixture was stirred at r.t. for 16 h. On completion, aqueous 10% HCl (10 mL) was added and this was then washed with Et$_2$O (2×10 mL). The aqueous layer was then basified to pH 9 with solid NaHCO$_3$ and extracted with EtOAc (3×15 mL). The combined organic fractions were dried (MgSO$_4$), filtered and concentrated in vacuo to give the title compound as a yellow solid (0.09 g, 86%) that was used crude. LCMS (ES+) 209.8 (M+H)$^+$.

Intermediate 83

4-Benzyl-3-(phenoxymethyl)morpholine

To a stirred solution of Intermediate 72 (1.27 g, 4.00 mmol) and Ag$_2$CO$_3$ (1.32 g, 4.80 mmol) in MeCN (50 mL) was added phenol (0.51 g, 4.80 mmol). The reaction mixture was then stirred at 60° C. for 16 h in the absence of light. On completion the reaction mixture was partitioned between DCM (100 mL) and aqueous sat. NaHCO$_3$ solution (20 mL). The organic phase was then dried over MgSO$_4$, filtered and concentrated in vacuo. Purification by column chromatography (SiO$_2$, DCM/hexanes) gave the title compound as an orange oil (0.77 g, 68%) which also contained 4-benzyl-6-phenoxy-1,4-oxazepane. LCMS (ES+) 284.2 (M+H)$^+$.

Intermediate 84

2-Amino-3-(1-benzothien-3-yl)propan-1-ol

The title compound was prepared from 3-(1-benzothien-3-yl)alanine according to Method D and was isolated as a white solid (89%) that required no further purification. $\delta_H$ (MeOD-d$_3$) 7.89 (2H, m), 7.35 (3H, m), 3.58 (1H, dd, J 10.7 and 4.6 Hz), 3.44 (1H, dd, J 10.7 and 6.5 Hz), 3.19 (1H, m), 3.05 (1H, m), 2.85 (1H, m). Exchangeable protons were not observed.

Intermediate 85

N-[2-(1-Benzothien-3-yl)-1-(hydroxymethyl ethyl]-2-chloroacetamide

The title compound was prepared from Intermediate 84 according to Method E and was isolated as a pink solid (91%) that was used crude. $\delta_H$ (CDCl$_3$) 7.92 (2H, m), 7.35 (2H, m), 7.24 (1H, s), 6.96 (1H, br. s), 4.36 (1H, m), 4.04 (1H, d, J 2.4 Hz), 3.71 (2H, m), 3.18 (2H, m). Exchangeable protons were not observed.

Intermediate 86

5-(1-Benzothien-3-ylmethyl)morpholin-3-one

The title compound was prepared from Intermediate 85 according to Method F and was isolated as a white solid (61%) that was used crude. $\delta_H$ (CDCl$_3$) 7.73 (1H, m), 7.61 (1H, m), 7.26 (2H, m), 7.05 (1H, s), 4.03 (2H, s), 3.65 (2H, m), 3.43 (1H, m), 2.95 (2H, m). Exchangeable proton was not observed.

Intermediate 87

3-(1-Benzothien-3-ylmethyl)morpholine

The title compound was prepared from Intermediate 86 according to Method G and was isolated as a white solid (84%) after purification by column chromatography (SiO$_2$, EtOAc). LCMS (ES+) 234.0 (M+H)$^+$.

Intermediate 88

N-{[4-(4-Methoxybenzyl)morpholin-3-yl]methyl}benzenesulfonamide

To a stirred solution of benzenesulfonamide (0.14 g, 0.84 mmol) in DMF (5 mL) was added, at 0° C., NaH (0.04 g, 0.86 mmol, 60% dispersion in mineral oil). The reaction mixture was then stirred for 30 minutes before the addition of Intermediate 113 (0.30 g, 0.86 mmol) in one portion. After stirring at r.t. for 45 minutes, the reaction was quenched by the addition of ice and partitioned between water (10 mL) and EtOAc (12 mL). The organic layer was washed with brine (10 mL), dried (MgSO$_4$), filtered and concentrated in vacuo to give a yellow oil. The title compound was obtained as a white solid (0.11 g, 34%) after purification by column chromatography (SiO$_2$, 1:1 EtOAc/hexanes). LCMS (ES+) 376.9 (M+H)$^+$.

Intermediate 89

N-(Morpholin-3-ylmethyl)benzenesulfonamide

To a stirred solution of Intermediate 88 (0.30 g, 0.80 mmol) in a mixture of MeCN (6 mL) and water (6 mL) at r.t. was added Ce(NH$_3$)$_4$NO$_2$ (1.30 g, 2.39 mmol). After stirring for 16 h, 10% aqueous HCl (10 mL) was added and the solution was washed with Et$_2$O (2×20 mL). The aqueous layer was then basified to pH 9 with aqueous sat. NaHCO$_3$ solution and extracted with EtOAc (3×25 mL). The combined organic fractions were dried over MgSO$_4$, filtered and concentrated in vacuo to give the title compound as a yellow oil (0.10 g, 49%) that was used crude. LCMS (ES+) 256.8 (M+H)$^+$.

Intermediate 90 tert-Butyl 3-(hydroxymethyl)morpholine-4-carboxylate

To a stirred solution of Intermediate 60 (4.50 g, 40.00 mmol) in DCM (100 mL) was added NEt$_3$ (5.50 mL, 0.04 mol) and di-tert-butyl dicarbonate (8.20 g, 40.00 mmol). The reaction mixture was stirred at r.t. for 16 h and was then transferred to a separating funnel and washed with aqueous sat. NaHCO$_3$ (60 mL) and brine (50 mL). The organics were dried over MgSO$_4$, filtered and concentrated in vacuo to give the title compound (6.50 g, 75%) as a colourless oil that required no further purification. $\delta_H$(CDCl$_3$) 4.00 (1H, br. m), 3.94 (1H, d, J 11.9 Hz), 3.87-3.81 (3H, m), 3.74 (1H, br. d, J 13.3 Hz), 3.55 (1H, dd, J 11.9 and 3.5 Hz), 3.46 (1H, dt, J 12.1 and 3.1 Hz), 3.21 (1H, br. m), 2.05 (1H, br. s), 1.48 (9H, s).

Intermediate 91 tert-Butyl 3-formylmorpholine-4-carboxylate

To a stirred solution of oxalyl chloride (3.73 g, 2.56 mL, 29.00 mmol) in DCM (80 mL) at −78° C. was added DMSO (4.93 g, 4.47 mL, 63.00 mmol) and, after 15 minutes, a solution of Intermediate 90 (5.70 g, 26.26 mmol) in DCM (50 mL) was added. The reaction mixture was then stirred at −78° C. for a further 2 h. NEt$_3$ (13.12 g, 18.71 mL, 129.70 mmol) was added and the reaction mixture was stirred at −78° C. for 30 minutes, warmed to r.t. and stirred for a further 1 h. The reaction mixture was then concentrated in vacuo and the residue partitioned between water (200 mL) and EtOAc (200 mL). The aqueous fraction was extracted with EtOAc (2×200 mL) and the combined organic fractions were washed with brine (300 mL), dried (MgSO$_4$), filtered and the solvents removed in vacuo to give the title compound (4.80 g, 84%) as a pale yellow solid that was used crude. $\delta_H$ (CDCl$_3$) 9.58 (1H, s), 4.31 (2H, m), 3.62 (2H, br. m), 3.41 (1H, br. m), 3.11 (1H, br. s), 2.93 (1H, br. m), 1.40 (9H, s).

Intermediate 92

Method Q tert-Butyl 3-[1-benzothien-2-yl(hydroxy)methyl]morpholine-4-carboxylate A stirred solution of benzothiophene (0.50 g, 2.32 mmol) in THF (15 mL) was cooled to −78° C. and "BuLi (1.6M in hexanes, 0.97 mL, 2.22 mmol) was added dropwise. After stirring at this temperature for 40 minutes, Intermediate 94 was added and the reaction mixture was allowed to warm to r.t. After stirring for 1.5 h, the reaction was quenched with ice and partitioned between EtOAc (30 mL) and aqueous NH$_4$Cl (20 mL). The organic layer was washed with brine (15 mL), dried over MgSO$_4$, filtered and concentrated in vacuo into a yellow oil. The crude material was purified by column chromatography (SiO$_2$, 1.5:1 EtOAc/hexanes) to give the title compound (0.53 g, 65%) as a white solid. LCMS (ES+) 276.2 (M-tert-butoxide)$^+$.

Intermediate 93

Method R tert-Butyl 3-(1-benzothien-2-yl {[(methylthio)carbonothioyl]oxy}methyl)morpholine-4-carboxylate To a stirred solution of Intermediate 92 (0.40 g, 1.20 mmol) in THF (25 mL) at 0° C. was added CS$_2$ (6.30 g, 5.00 mL, 83.00 mmol) followed by MeI (11.00 g, 5.00 mL, 81.00 mmol). After stirring for 15 minutes, NaH (0.10 g, 2.50 mmol, 60% dispersion in mineral oil) was added slowly and the reaction mixture was stirred at 0° C. for 20 minutes. The reaction mixture was then quenched with ice and partitioned between EtOAc (30 mL) and water (25 mL). The organic layer was washed with brine (20 mL), dried over MgSO$_4$, filtered and concentrated in vacuo to give a dark oil. The crude product was purified by column chromatography (SiO$_2$, 6:1 hexanes/EtOAc) to give the title compound (0.31 g, 62%) as a white solid. LCMS (ES+) 350.3 (M-tert-butyl)$^+$.

Intermediate 94

Method S tert-Butyl 3-(1-benzothien-2-ylmethyl)morpholine-4-carboxylate

To a stirred solution of Intermediate 93 (0.16 g, 0.40 mmol) in toluene (12 mL) was added Bu$_3$SnH (0.58 g, 0.54 mL, 2.00 mmol) and 2,2'-azobis(2-methylpropionitrile) (0.01 g, 0.02 mmol). The reaction mixture was heated to reflux for 1 h and on completion was cooled and concentrated in vacuo to a yellow oil. The tin by-products were removed by column chromatography (SiO$_2$, hexanes) followed by purification of the crude material (SiO$_2$, 4:1 hexanes/EtOAc) to give the title compound (0.07 g, 51%) as a white solid-6H (CDCl$_3$) 7.68 (1H, dd, J 8.0 and 1.1 Hz), 7.58 (1H, dd, J 6.8 and 1.4 Hz), 7.22 (2H, m), 7.01 (1H, s), 4.13 (1H, br. s), 3.82 (2H, m), 3.73 (1H, d, J 11.6 Hz), 3.42 (2H, dd, J 11.9 and 2.9 Hz), 3.27 (1H, dd, J 14.2 and 8.7 Hz), 3.18 (1H, dd, J 13.1 and 3.7 Hz), 3.07 (1H, dd, J 14.2 and 6.4 Hz), 1.29 (9H, s).

Intermediate 95

Method T 3-(1-Benzothien-2-ylmethyl)morpholine hydrochloride

To Intermediate 94 (0.07 g, 0.20 mmol) was added a solution of 4M HCl in 1,4-dioxane (5.00 mL, 0.60 mmol) and the reaction mixture was stirred at room temperature for 1 h. The reaction mixture was then concentrated in vacuo to give the title compound (0.05 g, 97%) as a white solid. LCMS (ES+) 234.2 (M+H)$^+$.

Intermediate 96 tert-Butyl 3-[hydroxy(isoquinolin-4-yl)methyl]morpholine-4-carboxylate

The title compound was prepared from Intermediate 91 and 4-bromoisoquinoline according to Method Q and was isolated as a white solid (54%) after purification by column chromatography (SiO$_2$, 1:1 DCM/EtOAc). LCMS (ES+) 345.5 (M+H)$^+$.

Intermediate 97 tert-Butyl 3-(isoquinolin-4-yl {[(methylthio)carbonothioyl]oxy}methyl)morpholine-4-carboxylate The title compound was prepared from Intermediate 96 according to Method R and was isolated as a white solid (51%) after purification by column chromatography (SiO$_2$, 1:1 DCM/EtOAc). LCMS (ES+) 435.5 (M+H)$^+$.

Intermediate 98 tert-Butyl 3-(isoquinolin-4-ylmethyl)morpholine-4-carboxylate

The title compound was prepared from Intermediate 97 according to Method S and was isolated as a white solid (76%) after purification by column chromatography (SiO$_2$, hexanes followed by 2:1 DCM/EtOAc). LCMS (ES+) 329.5 (M+H)$^+$.

Intermediate 99

4-(Morpholin-3-ylmethyl)isoquinoline dihydrochloride

The title compound was prepared from Intermediate 98 according to Method T and was isolated as a white solid (96%) that required no further purification. LCMS (ES+) 229.0 (M+H)$^+$.

Intermediate 100 tert-Butyl 3-[hydroxy(quinolin-5-yl methyl]morpholine-4-carboxylate

The title compound was prepared from Intermediate 91 and 5-bromoquinoline according to Method Q and was isolated as a white solid (34%) after purification by column chromatography (SiO$_2$, 1:2 hexanes/EtOAc). LCMS (ES+) 345.2 (M+H)$^+$.

Intermediate 101 tert-Butyl 3-[{[(methylthio)carbonothioyl]oxy} (quinolin-5-yl)methyl]morpholine-4-carboxylate The title compound was prepared from Intermediate 100 according to Method R and was isolated as a white solid (70%) after purification by column chromatography (SiO$_2$, DCM). LCMS (ES+) 435.4 (M+H)$^+$.

Intermediate 102 tert-Butyl 3-(quinolin-5-ylmethyl)morpholine-4-carboxylate

The title compound was prepared from Intermediate 101 according to Method S and was isolated as a white solid (98%) after purification by column chromatography (SiO$_2$, hexanes followed by DCM). LCMS (ES+) 329.2 (M+H)$^+$.

Intermediate 103

5-(Morpholin-3-ylmethyl)quinoline dihydrochloride

The title compound was prepared from Intermediate 102 according to Method T and was isolated as a white solid (98%) that required no further purification. LCMS (ES+) 229.2 (M+H)$^+$.

Intermediate 104 tert-Butyl 3-[hydroxy(quinolin-8-yl)methyl]morpholine-4-carboxylate

The title compound was prepared from Intermediate 91 and 8-bromoquinoline according to Method Q and was isolated as a white solid (41%) after purification by column chromatography (SiO$_2$, 1:1 DCM/EtOAc). LCMS (ES+) 345.4 (M+H)$^+$.

Intermediate 105 tert-Butyl 3-[{[(methylthio)carbonothioyl]oxy} (quinolin-8-yl)methyl]morpholine-4-carboxylate The title compound was prepared from Intermediate 104 according to Method R and was isolated as a white solid (86%) after purification by column chromatography (SiO$_2$, 4:1 DCM/EtOAc). LCMS (ES+) 435.4 (M+H)$^+$.

Intermediate 106 tert-Butyl 3-(quinolin-8-ylmethyl)morpholine-4-carboxylate

The title compound was prepared from Intermediate 105 according to Method S and was isolated as a white solid (76%) after purification by column chromatography (SiO$_2$, hexanes followed by 2:1 DCM/EtOAc). LCMS (ES+) 329.2 (M+H)$^+$.

Intermediate 107

8-(Morpholin-3-ylmethyl)quinoline dihydrochloride

The title compound was prepared from Intermediate 106 according to Method T and was isolated as a white solid (96%) that required no further purification. LCMS (ES+) 229.2 (+H)$^+$.

Intermediate 108

Tetrahydro-3H-[1,2,3]oxathiazolo[4,3-c][1,4]oxazine 1,1-dioxide

To a stirred solution of Intermediate 60 (0.50 g, 4.27 mmol) in DCM (5 mL) was added pyridine (0.68 g, 0.98 mL, 8.54 mmol) and the solution was cooled to −70° C. At this temperature was added sulphuryl chloride (0.58 g, 0.34 mL, 4.27 mmol) dissolved in DCM (5 mL) dropwise. The reaction mixture was stirred at this temperature for 1 h and at −10° C. for a further hour before being quenched by the addition of water (12 mL) and hexanes (30 mL). After extraction with DCM (2×20 mL), the combined organic fractions were washed with brine (2×15 mL), dried over MgSO$_4$, filtered and concentrated in vacuo to give the title compound as a colourless solid (0.52 g, 69%). $\delta_H$ (CDCl$_3$) 4.51 (1H, dd, J 8.1 and 6.4 Hz), 4.23 (1H, dd, J 9.1 and 8.1 Hz), 3.95 (1H, dd, J 11.6 and 3.4 Hz), 3.84-3.64 (3H, m), 3.54 (1H, dd, J 11.6 and 7.7 Hz), 3.29 (1H, dt, J 12.0 and 3.4 Hz), 3.06 (1H, m).

Intermediate 109

3-[(6-Bromopyridin-2-yl)methyl]morpholine

To a stirred solution of 2,6-dibromopyridine (0.40 g, 1.68 mmol) in THF (3.5 mL) at −78° C. was added $^n$BuLi (1.05 mL, 1.68 mmol, 1.60 M in hexanes) dropwise. After stirring at this temperature for 1 h, a solution of Intermediate 108 (0.25 g, 1.40 mmol) dissolved in THF (3 mL) was added slowly and the reaction mixture was allowed to warm to r.t. After stirring at r.t. for 16 h, the reaction mixture was quenched by the addition of water (a few drops) and the solvent was removed in vacuo. To the resultant dark oil were added aqueous HCl (2M, 3 mL) and EtOH (3 mL) and the reaction mixture was heated to reflux overnight. After cooling, the solvent was removed by evaporation in vacuo and DCM (20 mL) and aqueous sat. NaHCO$_3$ solution (10 mL) were added. After extraction with DCM (3×20 mL), the combined organics were concentrated in vacuo to give a dark oil. The crude material was purified by column chromatography (SiO$_2$, Chromabond® Flash FM 70/20 NH$_2$ column, DCM) to give the title compound as a white solid (0.14 g, 38%). LCMS (ES+) 257.1 and 259.1 (M+H)$^+$.

Intermediate 110

N-(4-Methoxybenzyl)serine

The title compound was prepared from serine (29.6 g, 0.3 mmol) and p-methoxybenzaldehyde (68.0 mL, 0.6 mmol) according to Method W and was obtained as a white solid (36.2 g, 59%) that was used crude. $\delta_H$ (DMSO-d$_6$) 7.37 (2H, dd, J 8.7 and 1.9 Hz), 6.93 (2H, dd, J 8.7 and 1.9 Hz), 3.99 (2H, s), 3.55 (3H, s), 3.73 (3H, m), 3.15 (1H, t, J 4.7 Hz). Not all exchangeable protons were observed.

Intermediate 111

4-(4-Methoxybenzyl)-5-oxomorpholine-3-carboxylic acid

The title compound was prepared from Intermediate 110 (35.0 g, 159.0 mmol) according to Method X and was isolated as a white solid (17.0 g, 42%) that was used crude. $\delta_H$ (DMSO-d$_6$) 7.20 (2H, d, J 8.6 Hz), 6.89 (2H, d, J 8.6 Hz), 5.19 (1H, d, J 15.5 Hz), 4.04-4.14 (3H, m), 3.85 (1H, m), 3.88 (1H, m), 3.73 (3H, s), 3.83 (1H, d, J 15.3 Hz). Exchangeable proton was not observed. LCMS (ES+) 266.2 (M+H)$^+$.

Intermediate 112

[4-(4-Methoxybenzyl)morpholin-3-yl]methanol

The title compound was prepared from Intermediate 111 (17.7 g, 67.0 mmol) according to Method Y and was isolated as a white solid (14.0 g, 88%) that required no further purification. $\delta_H$(CDCl$_3$) 7.25 (2H, d, J 8.6 Hz), 6.88 (2H, d, J 8.6 Hz), 4.12 (1H, d, J 13.1 Hz), 3.98 (1H, dd, J 11.5 and 4.4 Hz), 3.84 (1H, dd, J 11.6 and 3.9 Hz), 3.82 (3H, s), 3.75 (2H, m), 3.58 (2H, m), 3.26 (1H, d, J 13.1 Hz), 2.75 (1H, m), 2.57 (1H, br. m), 2.35 (1H, m). The exchangeable proton was not observed.

Intermediate 113

3-(Iodomethyl-4-(4-methoxybenzyl)morpholine

A solution of Intermediate 112 (0.20 g, 0.97 mmol), PPh$_3$ (0.25 g, 0.97 mmol) and imidazole (0.07 g, 0.97 mmol) in DCM (9 mL) was stirred at 0° C. for 5 minutes. I$_2$ (0.25 g, 0.97 mmol) was added portionwise and stirring was continued at 0° C. for 2.5 h. The reaction mixture was then concentrated in vacuo and purified by column chromatography (SiO$_2$, 3:1 hexanes/EtOAc) to give the title compound as a white solid (0.22 g, 71%). $\delta_H$(CDCl$_3$) 7.29 (2H, d, J 8.3 Hz), 6.89 (2H, d, J 8.3 Hz), 3.85 (1H, d, J 13.1 Hz), 3.82 (3H, s), 3.70 (2H, m), 3.59 (2H, m), 3.35 (1H, m), 3.24 (2H, m), 2.57 (1H, m), 2.35 (1H, m), 2.25 (1H, m).

Intermediate 114

N-Benzyl-D-serine

The title compound was prepared from D-serine and benzaldehyde according to Method W and was obtained as a white solid (88%) that was used crude. $\delta_H$ (DMSO-d$_6$) 7.45-7.30 (5H, m), 4.04-3.91 (2H, m), 3.70-3.61 (3H, m), 3.17 (1H, t, J 5.8 Hz). Not all exchangeable protons were observed.

Intermediate 115

(3R)-4-Benzyl-5-oxomorpholine-3-carboxylic acid

The title compound was prepared from Intermediate 114 according to Method X and was isolated as a white solid (43%) that was used crude. $\delta_H$ (DMSO-d$_6$) 13.51-12.53 (1H, br. s), 7.38-7.25 (5H, m), 5.27 (1H, d, J 15.3 Hz), 4.24-4.10 (3H, m), 3.94-3.88 (2H, m), 3.83 (1H, d, J 15.3 Hz). LCMS (ES+) 236.0 (M+H)$^+$.

Intermediate 116

[(3S)-(4-Benzylmorpholin-3-yl)]methanol

The title compound was prepared from Intermediate 115 according to Method Y and was isolated as a colourless oil (87%) that required no further purification. $\delta_H$ (CDCl$_3$) 7.29-7.16 (5H, m), 4.05 (1H, d, J 12.8 Hz), 3.88 (1H, dd, J 11.5 and 4.5 Hz), 3.78 (1H, m), 3.70-3.53 (2H, m), 3.51-3.40 (2H, m), 3.20 (1H, d, J 13.2 Hz), 2.68 (1H, dt, J 12.1 and 2.8 Hz), 2.48 (1H, m), 2.27 (1H, m), 2.20-2.15 (1H, br. s).

Intermediate 117

(3S)-Morpholin-3-ylmethanol

To a nitrogen flushed solution of Intermediate 116 (10.0 g, 48.3 mmol) in MeOH (300 mL) was added 10 wt % palladium on carbon (2.0 g) and the reaction mixture placed in a Parr® apparatus under 50 psi of hydrogen for 18 h. The resulting mixture was then filtered through Celite® and concentrated in vacuo to give the title compound as a clear oil (5.2 g, 92%). $\delta_H$ (CDCl$_3$) 3.81-3.76 (2H, m), 3.58-3.43 (3H, m), 3.35-3.28 (1H, m), 2.99-2.91 (5H, br. m). LCMS (ES+) 118.0 (M+H)$^+$.

Intermediate 118

Ethyl N-(tert-butoxycarbonyl)-5-hydroxy-L-tryptophanate

To a stirred solution of ethyl 5-hydroxy-L-tryptophanate hydrochloride (23.5 g, 82.6 mmol) in DCM (500 mL) was added NEt$_3$ (25.4 g, 35.0 mL, 247.8 mmol) and di-tert-butyl dicarbonate (18.0 g, 82.6 mmol). The reaction mixture was stirred for 3 h at r.t. and then partitioned with water (250 mL). The organic layer was washed with brine (200 mL), dried (MgSO$_4$), filtered and concentrated in vacuo to give the title compound as a cream solid (28.1 g, 98%) that required no further purification. $\delta_H$ (DMSO-d$_6$) 10.50 (1H, br. s), 8.58 (s, 1H), 7.14-7.05 (3H, m), 6.79 (1H, d, J 2.2 Hz), 6.59 (1H, dd, J 8.6 and 2.3 Hz), 5.75-3.99 (3H, s), 3.03-2.86 (2H, m), 1.35 (9H, s), 1.11 (3H, t, J 6.1 Hz). LCMS (ES+) 349.0 (M+H)$^+$.

Intermediate 119

Ethyl 5-(benzyloxy)-N-(tert-butoxycarbonyl)-L-tryptophanate

To a stirred solution of Intermediate 118 (5.4 g, 15.6 mmol) in MeCN (200 mL) was added Cs$_2$CO$_3$ (5.6 g, 17.1 mmol) and benzyl bromide (2.2 g, 2.0 mL, 17.1 mmol). The reaction mixture was stirred at 90° C. for 2.5 h, cooled and then stirred at r.t. for 48 h. After removal of the solvent in vacuo, the reaction mixture was partitioned between DCM (200 mL) and water (150 mL). The organic fraction was dried (MgSO$_4$), filtered and concentrated in vacuo to give a brown oil. To this crude material was added Et$_2$O (50 mL) and a solid precipitated out to give the title compound as a white solid (4.2 g, 59%). $\delta_H$ (DMSO-d$_6$) 10.68 (1H, br. s), 7.50-7.30 (7H, m), 7.23 (1H, d, J 8.7 Hz), 7.12 (1H, br. s), 6.79 (1H, dd, J 8.7 and 2.4 Hz), 5.09 (2H, s), 4.20-4.11 (1H, m), 4.09-4.00 (2H, m), 3.09-2.92 (2H, m), 1.33 (9H, s), 1.12 (3H, t, J 7.1 Hz). LCMS (ES+) 461.0 (M+H)$^+$.

Intermediate 120

Ethyl 5-(benzyloxy-L-tryptophanate hydrochloride

The title compound was prepared from Intermediate 119 according to Method T and was isolated as a white solid (96%) that required no further purification. $\delta_H$ (DMSO-d$_6$) 10.90 (1H, br. s), 8.47 (3H, br. s), 7.49-7.26 (6H, m), 7.19 (2H, d, J 2.0 Hz), 6.83 (1H, dd, J 8.7 and 2.3 Hz), 5.10 (2H, s), 4.20 (1H, t, J 6.2 Hz), 4.10 (2H, dd, J 14.3 and 7.1 Hz), 3.26-3.22 (2H, m), 1.12 (3H, t, J 7.1 Hz). LCMS (ES+) 339.0 (M+H)$^+$.

Intermediate 121

(2S)-2-Amino-3-[5-(benzyloxy)-1H-indol-3-yl]propan-1-ol

To a stirred solution of Intermediate 120 (3.30 g, 8.90 mmol) in THF (30 mL), at −10° C., was slowly added LiAlH$_4$ (1.00 g, 26.70 mmol). The reaction mixture was allowed to warm to r.t. and stirred for 2 h before being quenched, at 0° C., by the dropwise addition of aqueous sat. NaHCO$_3$. After filtration through Celite®, the filtrate was partitioned between EtOAc (50 mL) and water (35 mL). The organic layer was washed with brine (20 mL), dried (MgSO$_4$), filtered and concentrated in vacuo to give the title compound (2.31 g, 88%) as an orange oil that required no further purification. $\delta_H$ (DMSO-d$_6$) 10.63 (1H, br. s), 7.50-7.29 (7H, m), 7.23 (1H, d, J 8.7 Hz), 7.11 (1H, dd, J 13.3 and 2.2 Hz), 6.79 (1H, dd, J 8.7 and 2.4 Hz), 5.08 (2H, s), 4.50 (1H, br. s), 3.37-3.18 (2H, m), 2.99-2.91 (1H, m), 2.74 (1H, dd, J 14.1 and 5.7 Hz), 2.54 (1H, d, J 7.2 Hz), 1.77 (1H, br. s). LCMS (ES+) 297.0 (M+H)$^+$.

Intermediate 122

N-[(1S)-2-[5-(Benzyloxy)-1H-indol-3-yl]-1-(hydroxymethyl)ethyl]-2-chloroacetamide The title compound was prepared from Intermediate 121 according to Method E and was isolated as an orange oil (99%) that was used crude. LCMS (ES+) 373.0 (M+H)$^+$.

Intermediate 123

(5S)-5-{[5-(Benzyloxy)-1H-indol-3-yl] methyl}morpholin-3-one

The title compound was prepared from Intermediate 122 according to Method F and was isolated as a brown foam (93%) that was used crude. LCMS (ES+) 337.0 (M+H)$^+$.

Intermediate 124

5-(Benzyloxy)-3-[(3S)-morpholin-3-ylmethyl]-1H-indole

The title compound was prepared from Intermediate 123 according to Method G and was isolated as a brown foam (84%) that was used crude. LCMS (ES+) 323.0 (M+H)$^+$.

Intermediate 125

3-[(3S)-Morpholin-3-ylmethyl]-1H-indol-5-ol

To a nitrogen purged stirred solution of Intermediate 124 (2.00 g, 6.20 mmol) in AcOH (120 mL) was added a slurry of 10 wt % palladium on carbon (0.50 g suspended in IPA). The reaction mixture was stirred at 100° C. under 100 bar of hydrogen for 16 h. The reaction mixture was then filtered through Celite® and the solvents removed in vacuo to give the title compound (0.70 g, 50%) as a white solid. LCMS (ES+) 233.0 (M+H)$^+$.

Intermediate 126

(3aR)-Tetrahydro-3H-[1,2,3]oxathiazolo[4,3-c][1,4] oxazine 1,1-dioxide

To a stirred solution of Intermediate 117 (0.50 g, 4.27 mmol) in DCM (5 mL) was added pyridine (0.68 g, 0.98 mL, 8.54 mmol) and the solution was cooled to −70° C. At this temperature was added a solution of sulphuryl chloride (0.58 g, 0.34 mL, 4.27 mmol) in DCM (5 mL) dropwise. The reaction mixture was stirred at this temperature for 1 h, and then at −10° C. for a further hour, before it was quenched by the addition of water (12 mL) and hexanes (30 mL). After extraction with DCM (2×20 mL), the combined organic fractions were washed with brine (2×15 mL), dried (MgSO$_4$), filtered and concentrated in vacuo to give the title compound as a colourless solid (0.52 g, 69%). $\delta_H$ (CDCl$_3$) 4.51 (1H, dd, J 8.1 and 6.4 Hz), 4.23 (1H, dd, J 9.1 and 8.1 Hz), 3.95 (1H, dd, J 11.6 and 3.4 Hz), 3.84-3.64 (3H, m), 3.54 (1H, dd, J 11.6 and 7.7 Hz), 3.29 (1H, dt, J 12.0 and 3.4 Hz), 3.06 (1H, m).

Intermediate 127

(3S)-3-(3-Phenylprop-2-yn-1-yl)morpholine

To a stirred solution of Intermediate 126 (0.11 g, 0.60 mmol) and TMEDA (0.30 mL) in THF (3 mL) was added, at −78° C., lithium phenylacetylide (0.72 mL, 0.72 mmol) dropwise. After stirring for 3 h at r.t. the reaction mixture was quenched by the dropwise addition of water (a few drops) and then concentrated in vacuo. The resultant crude material was dissolved in MeOH (3 mL) and aqueous 10% HCl (1 mL) and the reaction mixture was stirred for 16 h at r.t. and for 2 h at 80° C. The solvent was then removed by evaporation in vacuo. To the resultant crude material was added DCM (20 mL) and the solution was basified by addition of aqueous sat. NaHCO$_3$ solution (10 mL). After extraction with DCM (3×20 mL), the combined organic fractions were dried (MgSO$_4$), filtered and concentrated in vacuo to give the title compound as a dark oil (0.05 g, 42%) which was used crude. LCMS (ES+) 202.0 (M+H)$^+$.

Intermediate 128

Method AA

1-[(3S)-Morpholin-3-ylmethyl]-1H-benzotriazole

To a stirred solution of Intermediate 126 (0.25 g, 1.40 mmol) in MeCN (5 mL) was added benzotriazole (0.36 g, 3.00 mmol). The reaction mixture was stirred at 60° C. for 6 h, cooled and then concentrated in vacuo. The resulting residue was dissolved in a mixture of EtOH (3 mL) and 10% aqueous HCl (3 mL). The reaction mixture was then stirred at 80° C. for 2 h and after cooling the solvent was removed by evaporation in vacuo. To the resultant crude material was added DCM (20 mL) and the solution was basified by addition of aqueous sat. NaHCO$_3$ solution (10 mL). After extraction with DCM (3×20 mL), the combined organics were dried (MgSO$_4$), filtered and concentrated in vacuo. Purification by column chromatography (SiO$_2$, Chromabond® Flash FM 70/20 NH$_2$ column, 0-5% MeOH/DCM) yielded the title compound (0.12 g, 37%) as a pale yellow solid. LCMS (ES+) 219.1 (M+H)$^+$.

Intermediate 129

1-[(3S)-Morpholin-3-ylmethyl]-1H-benzimidazole

The title compound was prepared from Intermediate 126 and benzimidazole according to Method AA, to give a pale yellow gum (0.06 g, 19%) that was used crude. LCMS (ES+) 218.1 (M+H)$^+$.

Intermediate 130

Method AC

[4-(5,5-Dimethyl-7-oxo-4,5,6,7-tetrahydro-1,3-benzothiazol-2-yl)morpholin-2-yl]acetic acid To a stirred solution of 2-morpholineacetic acid (0.10 g, 0.69 mmol) and Intermediate 15 (0.18 g, 0.69 mmol) in THF (4 mL) was added DIPEA (0.18 g, 1.38 mmol) and the mixture was heated under microwave irradiation in a sealed tube to 120° C. for 1 h. The reaction mixture was then concentrated in vacuo. Purification by preparative HPLC gave the title compound (0.07 g, 33%) as a white solid. $\delta_H$ (CDCl$_3$) 4.10 (3H, m), 3.80 (2H, m), 3.30 (1H, m), 3.10 (1H, m), 2.70-2.60 (4H, m), 2.40 (2H, s), 1.10 (6H, s). Exchangeable proton was not observed. LCMS (ES+) 325.0 (M+H)$^+$.

Intermediate 131

2-{[4-(5,5-Dimethyl-7-oxo-4,5,6,7-tetrahydro-1,3-benzothiazol-2-yl)morpholin-2-yl]methyl}-1H-isoindole-1,3(2H)-dione The title compound was prepared from 2-(1,4-oxazinan-2-ylmethyl)-1H-isoindole-1,3-(2H)-dione and Intermediate 15 according to Method AC and was isolated as a white solid (81%) after purification by preparative HPLC. $\delta_H$ (CDCl$_3$) 7.90 (2H, m), 7.71 (2H, m), 4.15-3.90 (4H, m), 3.80-3.60 (3H, m), 3.35 (1H, m), 3.10 (1H, m), 2.70 (2H, s), 2.40 (2H, s), 1.10 (6H, s). LCMS (ES+) 426.0 (M+H)$^+$.

Example 1

2-(Morpholin-4-yl)-4H-spiro[1,3-benzothiazole-5,1'-cyclopentan]-7(6M)-one

To a stirred solution of spiro[4,5]decane-7,9-dione (1.03 g, 6.2 mmol) in AcOH (10 mL) was added bromine (0.99 g, 0.32 mL, 6.2 mmol) dropwise. The reaction mixture was stirred for 2 h and then the product was isolated by filtration. The precipitate was washed twice with Et$_2$O (100 mL) and then dried in vacuo. The crude product (0.44 g) was dissolved in THF (50 mL). Intermediate 13 (0.262 g, 1.8 mmol) and N,N-diisopropylethylamine (0.23 g, 0.31 mL, 1.8 mmol) were added. The reaction mixture was heated to 85° C. for 2 h and then poured into NaHCO$_3$ solution (150 mL) and extracted with EtOAc (150 mL). The organic fraction was dried over MgSO$_4$ and concentrated in vacuo. The crude product was subjected to column chromatography (SiO$_2$, EtOAc) to yield the title compound (0.03 g, 2%, 2 steps) as a white solid. $\delta_H$ (DMSO-d$_6$) 3.73-3.68 (4H, m), 3.59-3.48 (4H, m), 2.74 (2H, s), 2.42 (2H, s), 1.68-1.57 (4H, m), 1.57-1.38 (4H, m). LCMS (ES+) 293.0 (M+H)$^+$.

Example 2

Method B

5-Isopropyl-2-(morpholin-4-yl)-5,6-dihydro-1,3-benzothiazol-7(4H)-one

To a stirred solution of Intermediate 3 (1 g, 4.2 mmol) in THF (50 mL) was added Intermediate 13 (0.62 g, 4.2 mmol) and N,N-diisopropylethylamine (0.54 g, 0.73 mL, 4.2 mmol). The reaction mixture was heated to 85° C. overnight and then poured onto NaHCO$_3$ solution (150 mL) and extracted with EtOAc (150 mL) twice. The organic fraction was dried over MgSO$_4$ and concentrated in vacuo. The solid was chromatographed (SiO$_2$, hexane-DCM) and then triturated with MeCN to yield the title compound (0.22 g, 19%) as a white solid. $\delta_H$ (DMSO-d$_6$) 3.69 (4H, d, J 5.2 Hz), 3.55 (4H, d, J 5.2 Hz), 2.80 (1H, dd, J 16.0 and 3.8 Hz), 2.55-2.23 (3H, m), 2.08-1.90 (1H, m), 1.69-1.58 (1H, m), 0.91 (6H, d, J 6.7 Hz). LCMS (ES+) 281.0 (M+H)$^+$.

Example 3

5-(4-Chlorophenyl)-2-(morpholin-4-yl)-5,6-dihydro-1,3-benzothiazol-7(4H)-one To a stirred solution of Intermediate 6 (1 g, 3.3 mmol) in THF (50 mL) was added Intermediate 13 (0.48 g, 3.3 mmol) and N,N-diisopropylethylamine (0.54 g, 0.73 mL, 4.2 mmol). The reaction was carried out according to Method B to yield the title compound (1.1 g, 96%) as a white solid. $\delta_H$ (DMSO-d$_6$) 7.46-7.45 (4H, m), 3.75 (4H, d, J 5.3 Hz), 3.63 (4H, d, J 5.3 Hz), 3.06-3.04 (2H, m), 2.87 (1H, dd, J 6.2 and 1.9 Hz), 2.64-2.62 (1H, m), 2.56 (1H, bs). LCMS (ES+) 349.0 (M+H)$^+$.

Example 4

2-(Morpholin-4-yl)-5-phenyl-5,6-dihydro-1,3-benzothiazol-7(4H)-one

To a stirred solution of Intermediate 5 (0.27 g, 1 mmol) in THF (10 mL) was added Intermediate 13 (0.15 g, 1 mmol) and N,N-diisopropylethylamine (0.13 g, 0.17 mL, 1 mmol).

The reaction was carried out according to Method B to yield the title compound (0.189 g, 60%) as a white solid. $\delta_H$ (DMSO-d$_6$) 7.40-7.16 (5H, m), 3.78-3.63 (4H, m), 3.62-3.43 (5H, m), 3.01 (2H, d, J 7.8 Hz), 2.82 (1H, dd, J 12.0 and 12.0 Hz), 2.57 (1H, dd, J 4.0 and 6.0 Hz). LCMS (ES+) 315.0 (M+H)$^+$.

Example 5

2-(Morpholin-4-yl)-4H-spiro[1,3-benzothiazole-5,1'-cyclohexan]-7(6H)-one

To a stirred solution of Intermediate 12 (0.26 g, 1 mmol) in THF (10 mL) was added Intermediate 13 (0.15 g, 1 mmol) and N,N-diisopropylethylamine (0.13 g, 0.17 mL, 1 mmol). The reaction was carried out according to Method B to yield the title compound (0.09 g, 34%) as a white solid. $\delta_H$ (DMSO-d$_6$) 3.76-3.65 (4H, m), 3.60-3.50 (4H, m), 2.72 (2H, s), 2.38 (2H, s), 1.52-1.28 (10H, m). LCMS (ES+) 307.0 (M+H)$^+$.

Preparative Example 6

2-(Morpholin-4-yl)-5,6-dihydro-1,3-benzothiazol-7(4H)-one

To a stirred solution of Intermediate 1 (0.19 g, 1 mmol) in THF (10 mL) was added Intermediate 13 (0.15 g, 1 mmol) and N,N-diisopropylethylamine (0.13 g, 0.17 mL, 1 mmol). The reaction was carried out as for Method B to yield, after recrystallisation from Et$_2$O, the title compound (0.07 g, 28%) as a white solid. $\delta_H$ (DMSO-d$_6$) 3.78-3.68 (4H, m), 3.60-3.50 (4H, m), 2.74 (2H, d, J 6.1 Hz), 2.41 (2H, d, J 5.9 Hz), 2.02 (2H, quin, J 6.4 Hz). LCMS (ES+) 238.9 (M+H)$^+$.

Example 7

5-(4-Methoxyphenyl)-2-(morpholin-4-yl)-5,6-dihydro-1,3-benzothiazol-7(4H)-one

To a stirred solution of Intermediate 9 (1.0 g, 3.5 mmol) in THF (50 mL) was added Intermediate 13 (0.51 g, 3.5 mmol) and N,N-diisopropylethylamine (0.45 g, 0.61 mL, 3.5 mmol). The reaction was carried out according to Method B to yield the title compound (0.13 g, 10%) as a white solid. $\delta_H$ (DMSO-d$_6$) 7.29-7.27 (2H, m), 6.90-6.87 (2H, m), 3.73-3.69 (5H, m), 3.58-3.51 (4H, m), 3.49-3.40 (1H, m), 3.29 (3H, s), 2.98-2.95 (2H, m), 2.77 (1H, dd, J 16.3 and 11.9 Hz). LCMS (ES+) 345.0 (M+H)$^+$.

Example 8

2-(Morpholin-4-yl)-5-propyl-5,6-dihydro-1,3-benzothiazol-7(4H)-one

To a stirred solution of Intermediate 4 (0.23 g, 1 mmol) in THF (10 mL) was added Intermediate 13 (0.15 g, 1 mmol) and N,N-diisopropylethylamine (0.23 g, 0.17 mL, 1 mmol). The reaction was carried out according to Method B to yield, after recrystallisation from Et$_2$O, the title compound (0.06 g, 20%) as a white solid. $\delta_H$ (DMSO-d$_6$) 3.78-3.62 (4H, m), 3.60-3.50 (4H, m), 2.85 (1H, dd, J 1.3 and 5.7 Hz), 2.50-2.30 (2H, m), 2.32-2.10 (2H, m), 1.47-1.26 (4H, m), 0.99-0.80 (3H, m). LCMS (ES+) 281.0 (M+H)$^+$.

Example 9

5-Methyl-2-(morpholin-4-yl)-5,6-dihydro-1,3-benzothiazol-7(4H)-one

To a stirred solution of Intermediate 8 (0.21 g, 1 mmol) in THF (10 mL) was added Intermediate 13 (0.15 g, 1 mmol) and N,N-diisopropylethylamine (0.13 g, 0.17 mL, 1 mmol). The reaction was carried out according to Method B to yield, after recrystallisation from Et$_2$O, the title compound (0.05 g, 19%) as a white solid. $\delta_H$ (DMSO-d$_6$) 3.75-3.65 (4H, m), 3.59-3.50 (4H, m), 2.84 (1H, dd, J 4.3 and 16.8 Hz), 2.56-2.22 (4H, m), 1.06 (3H, d, J 6.0 Hz). LCMS (ES+) 253.0 (M+H)$^+$.

Example 10

6,6-Dimethyl-2-(morpholin-4-yl)-5,6-dihydro-1,3-benzothiazol-7(4H)-one

To a stirred solution of Intermediate 7 (0.22 g, 1 mmol) in THF (10 mL) was added Intermediate 13 (0.15 g, 1 mmol) and N,N-diisopropylethylamine (0.23 g, 0.17 mL, 1 mmol). The reaction was carried out according to Method B to yield, after recrystallisation from Et$_2$O, the title compound (0.08 g, 29%) as a white solid. $\delta_H$ (DMSO-d$_6$) 3.75-3.65 (4H, m), 3.58-3.50 (4H, m), 2.78 (2H, t, J 6.2 Hz), 1.90 (2H, t, J 6.2 Hz), 1.08 (6H, s). LCMS (ES+) 267.0 (M+H)$^+$.

Example 11

5-[4-(Methylthio)phenyl]-2-(morpholin-4-yl)-5,6-dihydro-1,3-benzothiazol-7(4H)-one To a stirred solution of Intermediate 10 (1.0 g, 3.1 mmol) in THF (30 mL) was added Intermediate 13 (0.46 g, 3.1 mmol) and N,N-diisopropylethylamine (0.40 g, 0.54 mL, 3.1 mmol). The reaction was carried out according to Method B to yield the title compound (0.65 g, 52%) as a white solid. $\delta_H$ (CDCl$_3$) 7.18-7.14 (4H, m), 3.76-3.72 (4H, m), 3.57-3.54 (4H, m), 3.47-3.33 (1H, m), 3.07 (1H, dd, J 17.0 and 4.5 Hz), 2.91-2.81 (1H, m), 2.79-2.66 (2H, m), 2.41 (3H, s). LCMS (ES+) 361.0 (M+H)$^+$.

Example 12

5-(2-Furyl)-2-(morpholin-4-yl)-5,6-dihydro-1,3-benzothiazol-7(4H)-one

To a stirred solution of Intermediate 11 (0.71 g, 2.7 mmol) in THF (30 mL) was added Intermediate 13 (0.40 g, 2.7 mmol) and N,N-diisopropylethylamine (0.35 g, 0.47 mL, 2.7 mmol). The reaction was carried out according to Method B to yield the title compound (0.19 g, 22%) as a white solid. $\delta_H$ (CDCl$_3$) 7.61 (1H, m), 6.43 (1H, d, J 4.9 Hz), 6.22 (1H, d, J 4.9 Hz), 3.77-3.70 (4H, m), 3.69-3.60 (5H, m), 3.21 (1H, dd, J 16.9 and 4.9 Hz), 3.06-3.01 (1H, m), 2.98-2.71 (2H, m). LCMS (ES+) 305.0 (M+H)$^+$.

Example 13

6-Methyl-2-(morpholin-4-yl)-5,6-dihydro-1,3-benzothiazol-7(4H)-one

A solution of N,N-diisopropylamine (0.60 g, 0.83 mL, 5.9 mmol) in dry THF (5 mL) was cooled to −78° C. and n-butyllithium (2.36 mL, 2.5M in hexane, 5.9 mmol) was added dropwise. The reaction mixture was allowed to warm to 0° C., stirred for 15 minutes and cooled to −78° C. A suspension of Example 6 (1.4 g, 5.9 mmol) in THF (5 mL) was added slowly. The reaction mixture was warmed to 0° C. and stirred for 10 min at 0° C. before dropwise addition of methyl iodide (0.84 g, 0.37 mL, 5.9 mmol). A solid formed immediately. The reaction mixture was allowed to warm slowly to r.t. The solid was filtered, washed with THF and then purified by column chromatography (SiO$_2$, 1:3 EtOAc/hexane) to give the title compound (0.20 g, 13%) as a white solid. δ$_H$ (DMSO-d$_6$) 3.70 (4H, t, J 4.9 Hz), 3.54 (4H, t, J 4.9 Hz), 2.80-2.72 (2H, m), 2.55-2.45 (1H, m), 2.15-2.09 (1H, m), 1.82-1.72 (1H, m), 1.10 (3H, d, J 6.9 Hz). LCMS (ES+) 253.0 (M+H)$^+$.

Example 14

Method H

2-[(3R)-3-(1H-Indol-3-ylmethyl)morpholin-4-yl]-5,5-dimethyl-5,6-dihydro-1,3-benzothiazol-7(4H)-one To a stirred solution of Intermediate 19 (1.4 g, 6.5 mmol) and Intermediate 15 (1.5 g, 5.9 mmol) in IPA (60 mL) was added N,N-diisopropylethylamine (0.76 g, 1.03 mL, 5.9 mmol) and the mixture was heated to 85° C. for 16 h. The reaction mixture was concentrated in vacuo. Column chromatography (SiO$_2$, EtOAc) gave the title compound (1.1 g, 47%) as a solid. δ$_H$ (CDCl$_3$) 8.22 (1H, s), 7.81 (1H, d, J 6.8 Hz), 7.28 (1H, m), 7.11 (2H, m), 7.02 (1H, d, J 2.3 Hz), 4.05 (2H, m), 3.82 (2H, m), 3.62 (2H, m), 3.44 (2H, m), 2.99 (1H, dd, J 13.7 and 4.0 Hz), 2.65 (2H, s), 2.34 (2H, s), 1.07 (6H, s). LCMS (ES+) 396.0 (M+H)$^+$. Chiral purity: 93.6% ee, RT 5.10 minutes.

Example 15

5,5-Dimethyl-2-[3-(2-naphthylmethyl)morpholin-4-yl]-5,6-dihydro-1,3-benzothiazol-7(4H)-one The title compound was prepared from Intermediate 23 and Intermediate 15 according to Method H and was isolated as a solid in 83% yield after purification by column chromatography (SiO$_2$, 1.5:1 hexane/EtOAc). δ$_H$ (CDCl$_3$) 7.75 (3H, m), 7.66 (1H, s), 7.41 (3H, m), 4.04 (2H, m), 3.82 (1H, bs), 3.75 (1H, d, J 11.9 Hz), 3.60 (2H, m), 3.47 (1H, dd, J 10.8 and 2.0 Hz), 3.30 (1H, m), 3.05 (1H, dd, J 12.9 and 4.5 Hz), 2.61 (2H, d, J 3.1 Hz), 2.31 (2H, s), 1.04 (6H, s). LCMS (ES+) 407.0 (M+H)$^+$.

Example 16

5,5-Dimethyl-2-[3-(1-naphthylmethyl)morpholin-4-yl]-5,6-dihydro-1,3-benzothiazol-7(4H)-one The title compound was prepared from Intermediate 27 and Intermediate 15 according to Method H and was isolated as a solid in 76% yield after purification by column chromatography (SiO$_2$, 1:1 hexane/EtOAc). δ$_H$ (CDCl$_3$) 8.53 (1H, d, J 8.4 Hz), 7.88 (1H, d, J 8.0 Hz), 7.77 (1H, d, J 7.6 Hz), 7.22-7.68 (4H, m), 4.48 (1H, bs), 4.15 (1H, d, J 8.6 Hz), 3.75 (5H, m), 3.48 (2H, m), 2.75 (2H, d, J 3.1 Hz), 2.44 (2H, s), 1.18 (6H, s). LCMS (ES+) 407.0 (M+H)$^+$.

Example 17

5,5-Dimethyl-2-[3-(2-phenethyl)morpholin-4-yl]-5,6-dihydro-1,3-benzothiazol-7(4H)-one The title compound was prepared from Intermediate 31 and Intermediate 15 according to Method H and was isolated as a solid in 74% yield. δ$_H$ (CDCl$_3$) 7.20 (2H, m), 7.09 (3H, m), 3.85 (4H, m), 3.30-3.62 (3H, m), 2.63-2.45 (2H, m), 2.58 (2H, s), 2.30 (2H, s), 2.13 (2H, m), 1.05 (6H, s). LCMS (ES+) 371.0 (M+H)$^+$.

Example 18

2-[(3S)-3-Benzylmorpholin-4-yl]-5,5-dimethyl-5,6-dihydro-1,3-benzothiazol-7(4H)-one The title compound was prepared from Intermediate 34 and Intermediate 15 according to Method H and was isolated as a solid in 84% yield after purification by column chromatography (SiO$_2$, 1:1 hexane/EtOAc). δ$_H$ (CDCl$_3$) 7.29 (5H, m), 4.03 (1H, m), 3.95 (2H, bm), 3.81 (1H, d, J 11.9 Hz), 3.62 (3H, m), 3.21 (1H, dd, J 12.9 and 10.5 Hz), 2.95 (1H, dd, J 12.9 and 4.5 Hz), 2.70 (2H, s), 2.40 (2H, s), 1.13 (6H, s). LCMS (ES+) 357.0 (M+H)$^+$.

Example 19

5,5-Dimethyl-2-[(4aS,9aR)-2,3,9,9a-tetrahydroindeno[2,1-b][1,4]oxazin-4(4H)-yl]-5,6-dihydro-1,3-benzothiazol-7(4H)-one The title compound was prepared from Intermediate 37 and Intermediate 15 according to Method H and was isolated as a solid in 79% yield after purification by column chromatography (SiO$_2$, 1:1 hexane/EtOAc). δ$_H$ (CDCl$_3$) 7.24 (2H, m), 7.14 (1H, t, J 7.6 Hz), 7.02 (1H, d, J 7.5 Hz), 5.33 (1H, bs), 4.41 (1H, t, J 3.9 Hz), 3.77 (1H, dd, J 11.0 and 2.5 Hz), 3.68 (1H, bs), 3.63 (1H, dt, J 11.6 and 2.4 Hz), 3.28 (1H, m), 3.06 (1H, dd, J 16.6 and 4.0 Hz), 2.93 (1H, d, J 16.5 Hz), 2.65 (2H, s), 2.35 (2H, s), 1.09 (6H, s). LCMS (ES+) 355.0 (M+H)$^+$.

Example 20

2-[3-(4-Chlorobenzyl)morpholin-4-yl]-5,5-dimethyl-5,6-dihydro-1,3-benzothiazol-7(4H)-one The title compound was prepared from Intermediate 40 and Intermediate 15 according to Method H and was isolated as a solid in 87% yield after purification by column chromatography (SiO$_2$, 1:1 hexane/EtOAc). δ$_H$ (CDCl$_3$) 7.24 (4H, m), 4.06 (2H, m), 3.77 (2H, m), 3.61 (3H, m), 3.16 (1H, m), 2.93 (1H, dd, J 13.1 and 4.7 Hz), 2.68 (2H, s), 2.38 (2H, s), 1.12 (6H, s). LCMS (ES+) 391.0 (M+H)$^+$.

Example 21

5,5-Dimethyl-2-[3-(5-methyl-1H-indol-3-ylmethyl)morpholin-4-yl]-5,6-dihydro-1,3-benzothiazol-7(4H)-one The title compound was prepared from Intermediate 44 and Intermediate 15 according to Method H and was isolated as a solid in 82% yield after purification by column chromatography (SiO$_2$, 1:1 hexane/EtOAc). δ$_H$ (CDCl$_3$) 10.71 (1H, s), 7.63 (1H, d, J 8.1 Hz), 7.10 (2H, m), 6.86 (1H, d, J 8.1 Hz), 4.16 (1H, bs), 3.98 (1H, d, J 8.0 Hz), 3.73 (2H, m), 3.57 (3H, m), 3.31 (1H, m), 2.90 (1H, m), 2.51 (2H, s), 2.49 (3H, s), 2.38 (2H, s), 1.05 (6H, s). LCMS (ES+) 410.0 (M+H)$^+$.

Example 22

5,5-Dimethyl-2-{3-[4-(morpholin-4-yl)benzyl]morpholin-4-yl}-5,6-dihydro-1,3-benzothiazol-7(4H)-one To a mixture of $Pd_2(dba)_3$ (0.06 g, 0.06 mmol), 2-(di-tert-butylphosphino)biphenyl (0.08 g, 0.26 mmol), Example 20 (0.50 g, 1.28 mmol) and $^tBuONa$ (0.17 g, 1.79 mmol) was added toluene (3 mL) and morpholine (0.17 g, 1.92 mmol). The reaction mixture was stirred at 110° C. for 16 h. EtOAc (50 mL) was added and the organic phase washed with brine (40 mL), dried over $MgSO_4$ and concentrated to give an oil. Purification by column chromatography ($SiO_2$, 1:1 EtOAc/hexanes) gave the title compound (0.18 g, 31%) as a solid. $\delta_H$ ($CDCl_3$) 7.13 (2H, d, J 8.6 Hz), 6.81 (2H, d, J 8.6 Hz), 3.91 (2H, m), 3.78 (5H, m), 3.69 (1H, s), 3.50 (3H, m), 3.08 (5H, m), 2.78 (1H, dd, J 13.2 and 4.1 Hz), 2.63 (2H, s), 2.33 (2H, s), 1.06 (6H, s). LCMS (ES+) 442.2 $(M+H)^+$.

Example 23

2-(2,3-Dihydro-4H-1,4-benzoxazin-4-yl)-5,5-dimethyl-5,6-dihydro-1,3-benzothiazol-7(4H)-one To a solution of 3,4-dihydro-2H-1,4-benzoxazine (0.19 g, 1.27 mmol) in ethoxyethanol (5 mL) with one drop of conc. HCl was added Intermediate 15 (0.30 g, 1.15 mmol) and the reaction mixture was heated under microwave irradiation in a sealed tube to 160° C. for 20 minutes. The reaction mixture was then poured into EtOAc (25 mL) and washed with brine (25 mL). The organic fraction was dried over $MgSO_4$ and concentrated in vacuo to give the title compound (0.26 g, 64%) as a colourless solid. $\delta_H$($CDCl_3$) 7.83 (1H, dd, J 8.8 and 1.8 Hz), 7.01 (1H, m), 6.89 (2H, m), 4.27 (2H, m), 4.13 (2H, m), 2.69 (2H, s), 2.35 (2H, m), 1.07 (6H, s). LCMS (ES+) 315.0 $(M+H)^+$.

Example 24

5,5-Dimethyl-2-[3-(1H-indol-3-ylmethyl)morpholin-4-yl]-5,6-dihydro-1,3-benzothiazol-7(4H)-one The title compound was prepared from Intermediate 48 and Intermediate 15 according to Method H and was isolated as a solid in 85% yield after purification by column chromatography ($SiO_2$, 1:1 hexane/EtOAc). $\delta_H$($CDCl_3$) 8.22 (1H, s), 7.81 (1H, d, J 6.8 Hz), 7.28 (1H, m), 7.11 (2H, m), 7.02 (1H, d, J 2.3 Hz), 4.05 (2H, m), 3.82 (2H, m), 3.62 (2H, m), 3.44 (2H, m), 2.99 (1H, dd, J 13.7 and 4.0 Hz), 2.65 (2H, s), 2.34 (2H, s), 1.07 (6H, s). LCMS (ES+) 396 $(M+H)^+$.

Example 25

5,5-Dimethyl-2-[(3S)-3-(1H-indol-3-ylmethyl)morpholin-4-yl]-5,6-dihydro-1,3-benzothiazol-7(4H)-one The title compound was prepared from Intermediate 52 and Intermediate 15 according to Method H and was isolated as a solid in 88% yield after purification by column chromatography ($SiO_2$, 1:1 hexane/EtOAc). $\delta_H$($CDCl_3$) 8.22 (1H, s), 7.81 (1H, d, J 6.8 Hz), 7.28 (1H, m), 7.11 (2H, m), 7.02 (1H, d, J 2.3 Hz), 4.05 (2H, m), 3.82 (2H, m), 3.62 (2H, m), 3.44 (2H, m), 2.99 (1H, dd, J 13.7 and 4.0 Hz), 2.65 (2H, s), 2.34 (2H, s), 1.07 (6H, s). LCMS (ES+) 396.0 $(M+H)^+$. Chiral purity: 97.6% ee, RT 5.60 minutes.

Example 26

5,5-Dimethyl-2-{3-[(1-methyl-1H-indol-3-yl)methyl]morpholin-4-yl}-5,6-dihydro-1,3-benzothiazol-7(4H)-one To a stirred solution of Example 24 (0.10 g, 0.25 mmol) in DMF (5 mL) at 0° C. was added sodium hydride (0.01 g, 40% dispersion in oil, 0.28 mmol). After stirring at this temperature for 10 minutes, methyl iodide (0.02 mL, 0.28 mmol) was added. The reaction was stirred at r.t. for 1 h and then quenched by the addition of ice. The reaction mixture was then partitioned between EtOAc (15 mL) and water (10 mL) and the organic phase was dried over $MgSO_4$ and concentrated in vacuo. Purification by column chromatography ($SiO_2$, 1:1 EtOAc/hexanes) gave the title compound (0.08 g, 79%) as a white solid. $\delta_H$ ($CDCl_3$) 7.79 (1H, d, J 7.7 Hz), 7.09-7.24 (3H, m), 6.90 (1H, s), 4.05 (2H, m), 3.82 (1H, d, J 12.0 Hz), 3.79 (1H, bs), 3.68 (3H, s), 3.57 (2H, m), 3.41 (2H, m), 2.95 (1H, m), 2.67 (2H, s), 2.34 (2H, s), 1.11 (6H, s). LCMS (ES+) 410.0 $(M+H)^+$.

Example 27

2-{(3S)-3-[(1-Acetyl-1H-indol-3-yl)methyl]morpholin-4-yl}-5,5-dimethyl-5,6-dihydro-1,3-benzothiazol-7(4H)-one To a stirred solution of Example 25 (0.10 g, 0.25 mmol) in DCM (10 mL) was added triethylamine (0.03 g, 0.04 mL, 0.28 mmol), acetic anhydride (0.03 g, 0.03 mL, 0.30 mmol) and a catalytic amount of DMAP. The reaction mixture was stirred at r.t. for 16 h before being diluted with DCM (50 mL) and washed with sat. $NaHCO_3$ solution (2×25 mL) and sat. brine (25 mL). The organic fraction was dried over $MgSO_4$ and concentrated in vacuo. Purification by column chromatography ($SiO_2$, 45:55 EtOAc/hexanes) gave the title compound (0.05 g, 49%) as a white solid. $\delta_H$($CDCl_3$) 8.37 (1H, d, J 7.1 Hz), 7.82 (1H, dd, J 6.7 and 2.5 Hz), 7.32 (3H, m), 4.35 (1H, bs), 4.02 (1H, m), 3.82 (1H, d, J 11.9 Hz), 3.48-3.69 (4H, m), 3.31 (1H, m), 3.00 (1H, m), 2.66 (2H, d, J 3.3 Hz), 2.55 (3H, s), 2.34 (2H, s), 1.08 (6H, s). LCMS (ES+) 438.0 $(M+H)^+$.

Example 28

5,5-Dimethyl-2-(2-phenylmorpholin-4-yl)-5,6-dihydro-1,3-benzothiazol-7(4H)-one

The title compound was prepared from Intermediate 15 and 2-phenylmorpholine according to Method H and was isolated as a solid in 81% yield after purification by column chromatography ($SiO_2$, 1:1 hexane/EtOAc). $\delta_H$($CDCl_3$) 7.41 (5H, m), 4.62 (1H, dd, J 10.7 and 2.8 Hz), 4.16 (1H, dd, J 11.0 and 2.8 Hz), 4.13 (1H, d, J 16.3 Hz), 3.95 (1H, d, J 16.0 Hz), 3.87 (1H, dd, J 12.0 and 2.9 Hz), 3.45 (1H, m), 3.21 (1H, m), 2.72 (2H, s), 2.41 (2H, s), 1.15 (6H, s). LCMS (ES+) 343.0 $(M+H)^+$.

Example 29

2-[3-(4-Bromobenzyl)morpholin-4-yl]-5,5-dimethyl-5,6-dihydro-1,3-benzothiazol-7(4H)-one The title compound was prepared from Intermediate 56 and Intermediate 15 according to Method H and was isolated as a solid in 82% yield after purification by column chromatography (SiO$_2$, 1:1 hexane/EtOAc). δ$_H$ (CDCl$_3$) 7.35 (2H, d, J 8.3 Hz), 7.09 (2H, d, J 8.3 Hz), 3.95 (2H, m), 3.70 (2H, m), 3.61-3.45 (3H, m), 3.09 (1H, dd, J 13.2 and 10.2 Hz), 2.83 (1H, dd, J 13.2 and 4.7 Hz), 2.62 (2H, s), 2.33 (2H, s), 1.06 (6H, s). LCMS (ES+) 436.9 (M+H)$^+$.

Example 30

2-[3-(2,3-Dihydro-1H-indol-1-ylmethyl)morpholin-4-yl]-5,5-dimethyl-5,6-dihydro-1,3-benzothiazol-7(4H)-one To a solution of Intermediate 62 (0.22 g, 0.76 mmol) in MeOH (5 mL) was added indoline (0.11 g, 0.912 mmol) and the mixture was allowed to stir for 15 minutes at r.t. NaBH$_3$CN (0.06 g, 0.91 mmol) was added and the reaction mixture allowed to stir at r.t. for 24 h. The reaction mixture was concentrated in vacuo and the residue partitioned between EtOAc (50 mL) and brine (50 mL). The aqueous fraction was extracted with two further portions of EtOAc (50 mL) and the combined organic fractions washed with brine (100 ml), dried (MgSO$_4$), filtered and concentrated in vacuo. The crude product was purified by column chromatography (SiO$_2$, 1:4 EtOAc/hexanes) and subsequent crystallisation from Et$_2$O and hexanes gave the title compound (0.07 g, 25%) as pale yellow crystals. δ$_H$ (CDCl$_3$) 7.10-7.03 (2H, m), 6.75-6.67 (2H, m), 4.24 (1H, bs), 4.13-4.05 (2H, m), 3.83-3.78 (1H, m), 3.77-3.60 (3H, m), 3.59-3.43 (3H, m), 3.21 (1H, dd, J 13.6 and 4.4 Hz), 3.02-2.94 (2H, m), 2.79-2.67 (2H, m), 2.42 (2H, s), 1.16 (3H, s), 1.15 (3H, s). LCMS (MS+) 398.0 (M+H)$^+$.

Example 31

5,5-Dimethyl-2-[3-(1H-indol-1-ylmethyl morpholin-4-yl]-5,6-dihydro-1,3-benzothiazol-7(4H)-one To a solution of Example 30 (0.08 g, 0.2 mmol) in DCM (10 mL) was added manganese dioxide (0.15 g, 1.7 mmol) and the reaction mixture stirred at r.t. for 24 h. The reaction mixture was filtered through Celite® and the solvents removed in vacuo. Purification by column chromatography (SiO$_2$, 1:19 to 1:4 EtOAc/hexanes) gave the title compound (0.04 g, 44%) as a pale yellow solid. δ$_H$ (CDCl$_3$) 7.60 (1H, d, J 8.2 Hz), 7.53 (1H, d, J 7.9 Hz), 7.23-7.20 (1H, m), 7.09-7.02 (2H, m), 6.43 (1H, m), 4.54-4.47 (2H, m), 4.31-4.24 (1H, m), 4.06-4.01 (1H, m), 3.69-3.49 (5H, m), 2.65 (2H, d, J 5.3 Hz), 2.33 (2H, s), 1.08 (3H, s), 1.07 (3H, s). LCMS (MS+) 396.0 (M+H)$^+$.

Example 32

5-Dimethyl-2-(trans-2,6-dimethylmorpholin-4-yl)-5,6-dihydro-1,3-benzothiazol-7(4)-one The title compound was prepared from Intermediate 15 (0.26 g, 1 mmol) and 2,6-dimethylmorpholine (mixture of cis and trans isomers, 0.17 g, 1.49 mmol) according to Method H and was isolated by column chromatography (SiO$_2$, 15:85 EtOAc/hexanes) to give the title product (0.04 g, 12%) as a white solid. δ$_H$ (CDCl$_3$) 4.11-4.02 (2H, m), 3.65 (2H, d, J 12.8 and 3.4 Hz), 3.20 (2H, dd, J 12.9 and 6.4 Hz), 2.61 (2H, s), 2.31 (2H, s), 1.19 (6H, d, J 6.4 Hz), 1.05 (6H, s). LCMS (MS+) 295.0 (M+H)$^+$.

Example 33

Method I

2-[3-(Anilinomethyl)morpholin-4-yl]-5,5-dimethyl-5,6-dihydro-1,3-benzothiazol-7(4H)-one To a stirred solution of Intermediate 62 (0.10 g, 0.34 mmol) and aniline (0.16 g, 0.15 mL, 1.7 mmol) in MeOH (5 mL) with 4 Å molecular sieves was added NaBH$_3$CN (0.03 g, 0.40 mmol) and a catalytic amount of AcOH. After stirring for 16 h at r.t., the reaction mixture was filtered, concentrated in vacuo and partitioned between EtOAc (20 mL) and sat. NaHCO$_3$ solution (20 mL). The organic fraction was dried over MgSO$_4$ and concentrated in vacuo. Purification by column chromatography (SiO$_2$, EtOAc/hexane) gave the title compound (3 mg, 2%) as a solid. δ$_H$ (CDCl$_3$) 7.13-7.09 (2H, m), 6.67-6.64 (3H, m), 4.34 (1H, bs), 4.03-3.94 (2H, m), 3.63-3.44 (7H, m), 2.64 (2H, s), 2.33 (2H, s), 1.08 (3H, s), 1.07 (3H, s). LCMS (ES+) 372.0 (M+H)$^+$.

Example 34

5,5-Dimethyl-2-{3-[(N-methyl-N-phenylamino)methyl]morpholin-4-yl}-5,6-dihydro-1,3-benzothiazol-7(4H)-one To a stirred solution of Intermediate 62 (0.25 g, 0.85 mmol) and N-methylaniline (0.46 g, 0.46 mL, 4.25 mmol) in MeOH (20 mL) with 4 Å molecular sieves was added NaBH$_3$CN (0.06 g, 1.02 mmol) and a catalytic amount of AcOH. The reaction was then carried out according to Method I to give the title compound (0.108 g, 32%) as a solid. δ$_H$ (CDCl$_3$) 7.20-7.16 (2H, m), 6.83-6.81 (2H, m), 6.66 (1H, t, J 7.3 Hz), 4.22 (1H, bs), 3.98 (1H, dd, J 11.0 and 3.4 Hz), 3.93-3.90 (1H, m), 3.77-3.62 (1H, m), 3.60-3.56 (3H, m), 3.48-3.36 (2H, m), 2.94 (3H, s), 2.62 (2H, s), 2.32 (2H, s), 1.07 (3H, s), 1.06 (3H, s). LCMS (ES+) 386.0 (M+H)$^+$.

Example 35

2-[3-(3,4-Dihydroquinolin-1(2H)-ylmethyl)morpholin-4-yl]-5,5-dimethyl-5,6-dihydro-1,3-benzothiazol-7(4H)-one To a stirred solution of Intermediate 62 (0.25 g, 0.85 mmol) and 1,2,3,4-tetrahydroquinoline (0.57 g, 0.53 mL, 4.25 mmol) in MeOH (20 mL) with 4 Å molecular sieves was added NaBH$_3$CN (0.06 g, 1.02 mmol) and a catalytic amount of AcOH. The reaction was then carried out according to Method I to give the title compound (0.08 g, 22%) as a solid. δ$_H$ (CDCl$_3$) 7.03 (1H, t, J 7.2 Hz), 6.94 (1H, d, J 8.1 Hz), 6.87 (1H, d, J 7.2 Hz), 6.54 (1H, t, J 7.2 Hz), 4.00 (1H, bs), 3.99-3.92 (2H, m), 3.69-3.57 (4H, m), 3.49-3.45 (1H, m), 3.33-3.27 (3H, m), 2.66 (2H, t, J 6.2 Hz), 2.61 (2H, s), 2.32 (2H, s), 1.89-1.79 (2H, m), 1.06 (6H, s). LCMS (ES+) 412.0 (M+H)$^+$.

Example 36

2-[3-(3,4-Dihydroisoquinolin-2(1H)-ylmethyl)morpholin-4-yl]-5,5-dimethyl-5,6-dihydro-1,3-benzothiazol-7(4H)-one To a stirred solution of Intermediate 62 (0.25 g, 0.85 mmol) and 1,2,3,4-tetrahydroisoquinoline (0.57 g, 0.53 mL, 4.25 mmol) in MeOH (20 mL) with 4 Å molecular sieves was added NaBH$_3$CN (0.06 g, 1.02 mmol) and a catalytic amount of AcOH. The reaction was then carried out according to Method I to give the title compound (0.09 g, 25%) as a solid. $\delta_H$ (CDCl$_3$) 7.15-7.03 (4H, m), 4.19 (1H, d, J 11.8 Hz), 4.02 (2H, m), 3.99-3.79 (3H, m), 3.69-3.60 (2H, m), 3.49-3.39 (1H, m), 3.11-3.04 (1H, m), 2.94-2.86 (4H, m), 2.68-2.62 (3H, m), 2.39 (2H, s), 1.14 (3H, s), 1.12 (3H, s). LCMS (ES+) 412.0 (M+H)$^+$.

Example 37

(7E,Z)-5,5-Dimethyl-2-(morpholin-4-yl)-5,6-dihydro-1,3-benzothiazol-7(4H)-one oxime The title compound (mixture of two regioisomers, ratio 1:5.5) was prepared by Method J by reaction of Example 48 (2.5 g, 9.39 mmol), hydroxylamine (6.5 g, 93.98 mmol) and pyridine (50 mL) in quantitative yield. $\delta_H$ (DMSO-d$_6$) 10.81 (1H, s, major regioisomer), 10.57 (1H, s, minor regioisomer), 3.69 (4H, t, J 4.8 Hz), 3.43 (4H, t, J 4.9 Hz), 2.54 (2H, s), 2.26 (2H, s), 0.99 (6H, s). LCMS (ES+) 282 (M+H)$^+$.

Example 38

(7Z)-5,5-Dimethyl-2-(morpholin-4-yl)-5,6-dihydro-1,3-benzothiazol-7(4H)-one oxime To a stirred solution of Intermediate 63 (1:15 ratio of two regioisomers, 0.35 g, 1.27 mmol) in IPA (5 mL) was added morpholine (0.22 g, 0.22 mL, 2.55 mmol) and N,N-diisopropylethylamine (0.33 g, 0.44 mL, 2.55 mmol). The reaction mixture was stirred at 80° C. for 2 days, then cooled to r.t. Water (10 mL) was added. The solid formed was filtered and washed with water (3×10 mL), EtOAc (3×10 mL), MeOH (3×10 mL) then Et$_2$O (10 mL), to give the title compound (0.03 g, 7.5%) (contaminated with 3% of the other regioisomer) as a grey solid. $\delta_H$ (DMSO-d$_6$) 10.81 (1H, s), 3.69 (4H, t, J 4.8 Hz), 3.43 (4H, t, J 4.9 Hz), 2.53 (2H, s), 2.26 (2H, s), 0.99 (6H, s). LCMS (ES+) 282.0 (M+H)$^+$.

Example 39

(7E,Z)-2-(Morpholin-4-yl)-5,6-dihydro-1,3-benzothiazol-7(4H)-one oxime

The title compound (mixture of two regioisomers, ratio 1:7.7) was prepared by Method J by reaction of Example 6 (1.0 g, 4.2 mmol), hydroxylamine (2.9 g, 42 mmol) and pyridine (20 mL). $\delta_H$ (DMSO-d$_6$) 10.80 (1H, s, major regioisomer), 10.56 (1H, s, minor regioisomer), 3.69 (4H, t, J 4.8 Hz), 3.43 (4H, t, J 4.9 Hz), 2.68 (2H, t, J 6.1 Hz), 2.53-2.60 (2H, m, minor regioisomer), 2.44 (2H, t, J 6.2 Hz), 1.81-1.89 (2H, m). LCMS (ES+) 254.0 (M+H)$^+$.

Example 40

(7E,Z)-5,5-Dimethyl-2-[(3S)-3-(1H-indol-3-ylmethyl)morpholin-4-yl]-5,6-dihydro-1,3-benzothiazol-7(4H)-one oxime The title compound (mixture of two regioisomers, ratio 1:5) was prepared by Method J by reaction of Example 25 (1.0 g, 2.53 mmol), hydroxylamine (1.8 g, 25.32 mmol) and pyridine (15 mL). $\delta_H$ (DMSO-d$_6$) 10.89 (1H, s, major regioisomer), 10.57 (1H, s, minor regioisomer), 7.84 (1H, d, J 7.8 Hz), 7.35 (1H, d, J 8.1 Hz), 7.18 (1H, s), 7.09 (1H, t, J 7.1 Hz), 7.00 (1H, d, J 7.4 Hz), 4.13 (1H, d, J 9.7 Hz), 3.96 (1H, d, J 9.8 Hz), 3.71 (1H, d, J 11.5 Hz), 3.64 (1H, d, J 10.8 Hz), 3.46-3.59 (3H, m), 3.28 (1H, d, J 10.9 Hz), 2.86 (1H, dd, J 3.5 and 13.6 Hz), 2.60 (2H, s), 2.28 (2H, s), 1.01 (6H, s). LCMS (ES+) 411.0 (M+H)$^+$.

Example 41

(7E,Z)-6-Methyl-2-(morpholin-4-yl)-5,6-dihydro-1,3-benzothiazol-7(4H)-one oxime

The title compound (mixture of two regioisomers, ratio 1:11) was prepared by Method J by reaction of Example 13 (0.19 g, 0.74 mmol), hydroxylamine (0.51 g, 7.38 mmol) and pyridine (5 mL). The reaction was complete after 4 days. $\delta_H$ (DMSO-d$_6$) 10.92 (1H, s, major regioisomer), 10.54 (1H, s, minor regioisomer), 3.69 (4H, t, J 4.8 Hz), 3.42 (4H, t, J 4.8 Hz), 2.60-2.76 (3H, m), 1.89-1.97 (1H, m), 1.64-1.72 (1H, m), 1.15 (6H, d, J 6.8 Hz, major regioisomer), 1.15 (6H, d, J 7.1 Hz, minor regioisomer). LCMS (ES+) 268.0 (M+H)$^+$.

Example 42

(7E,Z)-6,6-Dimethyl-2-(morpholin-4-yl)-5,6-dihydro-1,3-benzothiazol-7(4H)-one oxime The title compound (mixture of two regioisomers) was prepared by Method J by reaction of Example 10 (0.36 g, 1.36 mmol), hydroxylamine (0.95 g, 13.65 mmol) and pyridine (5 mL). The reaction was complete after 4 days. $\delta_H$ (DMSO-d$_6$) 11.00 (1H, s), 3.69 (4H, t, J 4.8 Hz), 3.42 (4H, t, J 4.9 Hz), 2.68 (2H, t, J 6.2 Hz), 1.72 (2H, t, J 6.2 Hz), 1.16 (6H, s). LCMS (ES+) 282.0 (M+H)$^+$.

Preparative Example 43

Method K 7,7-Dimethyl-2-(morpholin-4-yl)-5,6,7,8-tetrahydro-4H-[1,3]thiazolo[5,4-c]azepin-4-one To a stirred solution of Example 37 (4.10 g, 14.59 mmol) in pyridine (70 mL) was added p-toluenesulphonyl chloride (3.10 g, 16.05 mmol). The reaction mixture was stirred at 65° C. for 16 h. The solvent was evaporated in vacuo and DCM (30 mL) and water (20 mL) were added. The aqueous layer was extracted with DCM (3×15 mL). The combined organic layers were washed with water (3×30 mL), dried (MgSO$_4$), filtered and the solvent evaporated in vacuo. The oily residue was purified by column chromatography (SiO$_2$, loading with CH$_2$Cl$_2$ and eluting with 1:1 EtOAc/hexane, then EtOAc) to give the title compound (0.78 g, 19%) as a white solid. $\delta_H$ (DMSO-d$_6$) 7.69-7.71 (1H, t, J 4.7 Hz), 3.68 (4H, t, J 4.9 Hz), 3.40 (4H, t, J 4.9 Hz), 2.94 (2H, d, J 5.0 Hz), 2.67 (2H, s), 0.97 (6H, s). LCMS (ES+) 282.0 (M+H)$^+$. CHN analysis. Found (% C, 55.19; % H, 6.77; % N 14.79). Calculated for C$_{13}$H$_{19}$N$_3$SO$_2$ (% C. 55.49; % H. 6.81; % N. 14.93).

Preparative Example 44

2-(Morpholin-4-yl)-5,6,7,8-tetrahydro-4H-[1,3]thiazolo[5,4-c]azepin-4-one

The title compound was prepared by Method K by reaction of Example 39 (1.4 g, 5.53 mmol), p-toluenesulphonyl chloride (1.2 g, 6.09 mmol) and pyridine (30 mL). $\delta_H$ (DMSO-d$_6$) 7.77 (1H, s), 3.68 (4H, t, J 4.9 Hz), 3.40 (4H, t, J 4.9 Hz), 3.18-3.21 (2H, m), 2.84 (2H, t, J 6.4 Hz), 1.87-1.92 (2H, m). LCMS (ES+) 254.0 (M+H)$^+$.

Example 45

7,7-Dimethyl-2-[(3S)-3-(1H-indol-3-ylmethyl)morpholin-4-yl]-5,6,7,8-tetrahydro-4H-[1,3]thiazolo[5,4-c]azepin-4-one The title compound was prepared by Method K by reaction of Example 40 (1.0 g, 2.53 mmol), p-toluenesulphonyl chloride (0.53 g, 2.78 mmol) and pyridine (20 mL). $\delta_H$ (DMSO-$d_6$) 10.89 (1H, s), 7.80 (1H, d, J 7.8 Hz), 7.70 (1H, d, J 4.7 Hz), 7.34 (1H, d, J 7.8 Hz), 7.19 (1H, s), 7.08 (1H, t, J 7.4 Hz), 7.01 (1H, d, J 7.2 Hz), 4.07 (1H, s), 3.96 (1H, d, J 7.5 Hz), 3.70 (1H, d, J 11.5 Hz), 3.60 (1H, d, J 8.9 Hz), 3.38-3.56 (3H, m), 3.25-3.31 (1H, m), 2.95 (2H, d, J 4.4 Hz), 2.88 (1H, dd, J 3.7 and 13.7 Hz), 2.73 (2H, s), 0.99 (6H, s). LCMS (ES+) 411.0 (M+H)$^+$.

Example 46

6-Methyl-2-(morpholin-4-yl)-5,6,7,8-tetrahydro-4H-[1,3]thiazolo[5,4-c]azepin-4-one The title compound was prepared by Method K by reaction of Example 41 (0.16 g, 0.61 mmol), p-toluenesulphonyl chloride (0.14 g, 0.73 mmol) and pyridine (5 mL). $\delta_H$ (DMSO-$d_6$) 7.61 (1H, d, J 2.5 Hz), 3.69 (4H, t, J 4.9 Hz), 3.46-3.50 (1H, m), 3.40 (4H, t, J 4.9 Hz), 2.84 (2H, t, J 6.6 Hz), 1.80-1.94 (1H, m), 1.73-1.79 (1H, m), 1.16 (3H, d, J 6.7 Hz). LCMS (ES+) 268.0 (M+H)$^+$.

Example 47

6,6-Dimethyl-2-(morpholin-4-yl)-5,6,7,8-tetrahydro-4H-[1,3]thiazolo[5,4-c]azepin-4-one The title compound was prepared by Method K by reaction of Example 42 (0.36 g, 1.28 mmol), p-toluenesulphonyl chloride (0.29 g, 1.54 mmol) and pyridine (8 mL). $\delta_H$ (DMSO-$d_6$) 7.51 (1H, s), 3.68 (4H, t, J 4.9 Hz), 3.40 (4H, t, J 4.9 Hz), 2.83 (2H, t, J 6.3 Hz), 1.84 (2H, t, J 6.3 Hz), 1.20 (6H, s). LCMS (ES+) 282.0 (M+H)$^+$.

Preparative Example 48

5,5-Dimethyl-2-(morpholin-4-yl)-5,6-dihydro-1,3-benzothiazol-7(4H)-one

The title compound was prepared from morpholine and Intermediate 15 according to Method H and was isolated as white crystals in 60% yield after purification by recrystallisation from EtOAc. $\delta_H$ (DMSO-$d_6$) 3.77-3.60 (4H, m), 3.59-3.50 (4H, m), 2.65 (2H, s), 2.31 (2H, s), 1.04 (6H, s). LCMS (ES+) 267.1 (M+H)$^+$.

Example 49

5,5-Dimethyl-2-(morpholin-4-yl)-4,5,6,7-tetrahydro-1,3-benzothiazol-7-ol

To a stirred solution of Example 48 (0.13 g, 0.5 mmol) in THF (10 mL) at r.t. was added LiAlH$_4$ (0.5 mL, 1M solution in THF, 0.5 mmol) dropwise. The reaction mixture was stirred at r.t. for 2 h and then poured into 10% NaOH solution (20 mL) and extracted with DCM (2×20 mL). The combined organic fractions were dried over MgSO$_4$, filtered and the solvent removed by evaporation in vacuo. Purification by column chromatography gave the title compound (0.07 g, 52%) as a solid. $\delta_H$ (DMSO-$d_6$) 5.23 (1H, d, J 6.5 Hz), 4.65 (1H, dt, J 8.1 and 6.7 Hz), 3.77-3.70 (4H, m), 3.39 (4H, m), 2.40-2.24 (2H, m), 1.84 (1H, dd, J 5.9 and 11.3 Hz), 1.48 (1H, dd, J 8.8 and 12.6 Hz), 1.09 (3H, s), 0.94 (3H, s). LCMS (ES+) 269.0 (M+H)$^+$.

Example 50

5,5-Dimethyl-2-(morpholin-4-yl)-5,6-dihydro-1,3-benzothiazole-7(4H)-thione

To a stirred solution of Example 48 (0.266 g, 1 mmol) in THF (10 mL) at r.t. was added 2,4-bis(4-methoxyphenyl)-1,3-dithia-2,4-diphosphetane-2,4-disulphide (0.808 g, 2 mmol). The reaction mixture was stirred for 2 h and then poured into saturated NaHCO$_3$ solution (50 ml) and extracted with DCM (2×50 mL). The combined organic fractions were dried over MgSO$_4$, filtered and the solvent removed by evaporation in vacuo to give the title compound (0.14 g, 50%) as a solid. $\delta_H$ (DMSO-$d_6$) 3.72-3.60 (8H, m), 2.74 (2H, s), 2.61 (2H, s), 1.02 (6H, s). LCMS (ES+) 283.0 (M+H)$^+$.

Example 51

2-[(3S)-3-(3-Bromobenzyl)morpholin-4-yl]-5,5-dimethyl-5,6-dihydro-1,3-benzothiazol-7(4H)-one The title compound was prepared from Intermediate 69 and Intermediate 15 according to Method H and was isolated as a pale yellow solid (22%) after purification by column chromatography (SiO$_2$, 1:1 hexanes/EtOAc). $\delta_H$ (DMSO-$d_6$) 7.46 (1H, s), 7.39-7.36 (1H, m), 7.26-7.16 (2H, m), 4.15-4.04 (2H, m), 3.81-3.77 (2H, m), 3.71-3.53 (2H, m), 3.16 (1H, dd, J 13.0 and 10.0 Hz), 2.97 (1H, dd, J 13.0 and 4.9 Hz), 2.72 (2H, s), 2.41 (2H, s), 1.15 (6H, s). LCMS (ES+) 437.2 (M+H)$^+$.

Example 52

Method L

2-[(3S)-3-(Biphenyl-3-ylmethyl)morpholin-4-yl]-5,5-dimethyl-5,6-dihydro-1,3-benzothiazol-7(4H)-one Pd(PPh$_3$)$_4$ (0.03 g, 0.02 mmol) was added to a mixture of Example 51 (0.10 g, 0.22 mmol), phenylboronic acid (0.40 g, 0.34 mmol) and 2M Na$_2$CO$_3$ solution (0.22 mL, 0.45 mmol) in DME (5 mL), and the mixture was heated at 80° C. for 16 h. On completion, the reaction mixture was concentrated in vacuo and partitioned between EtOAc (100 mL) and brine (100 mL). The organic phase was dried over MgSO$_4$, filtered and concentrated in vacuo. Purification by column chromatography (SiO$_2$, 1:1 hexanes/EtOAc) gave the title compound as a white solid (0.07 g, 68%). $\delta_H$ (DMSO-$d_6$) 7.52-7.49 (2H, m), 7.48-7.22 (7H, m), 4.06-4.00 (2H, m), 3.98 (2H, d, J 7.8 Hz), 3.59-3.47 (4H, m), 3.19 (1H, dd, J 13.1 and 10.2 Hz), 2.60 (2H, br. s), 2.31 (2H, br. s), 1.04 (6H, s). LCMS (ES+) 432.0 (M+H)$^+$.

Example 53

5,5-Dimethyl-2-[(3S)-3-(3-(pyridin-3-yl)benzyl)morpholin-4-yl]-5,6-dihydro-1,3-benzothiazol-7(4H)-one The title compound was prepared from Example 51 and 3-pyridineboronic acid according to Method L and was isolated as a white solid (55%). δ$_H$ (DMSO-d$_6$) 8.83-8.82 (1H, m), 8.56 (1H, dd, J 4.7 and 1.5 Hz), 7.99 (1H, dd, J 6.7 and 2.2 Hz), 7.65-7.31 (5H, m), 4.26 (1H, br. s), 3.99-3.96 (1H, m), 3.80-3.51 (5H, m), 3.15 (2H, t, J 6.8 Hz), 2.50 (2H, s), 2.22 (2H, s), 0.95 (3H, s), 0.93 (3H, s). LCMS (ES+) 434.2 (M+H)$^+$.

Example 54

Method M

5,5-Dimethyl-2-{(3S)-3-[3-(3-thienyl)benzyl]morpholin-4-yl}-5,6-dihydro-1,3-benzothiazol-7(4H)-one Pd(OAc)$_2$ (0.002 g, 0.006 mmol) and 2-dicyclohexylphosphino-2',6'-dimethoxybiphenyl (0.006 g, 0.010 mmol) were added to Example 51 (0.150 g, 0.330 mmol), 3-thiopheneboronic acid (0.065 g, 0.510 mmol) and K$_3$PO$_4$ (0.140 g, 0.660 mmol) in BuOH/water (2.5 mL/1.0 mL), and the mixture heated at 80° C. for 16 h. On completion, the reaction mixture was concentrated in vacuo and partitioned between EtOAc (100 mL) and brine (100 mL). The organic phase was dried over MgSO$_4$, filtered and concentrated in vacuo. Purification by column chromatography (SiO$_2$, 1:1 hexanes/EtOAc) gave the title compound as a white solid (0.047 g, 31%). δ$_H$ (DMSO-d$_6$) 7.79-7.77 (1H, m), 7.64-7.61 (1H, m), 7.57 (1H, s), 7.51-7.48 (2H, m), 7.30 (1H, t, J 7.6 Hz), 7.20-7.18 (1H, m), 4.23 (1H, br. s), 3.99-3.96 (1H, m), 3.77-3.51 (5H, m), 3.11-3.09 (2H, m), 2.54-2.50 (2H, m), 2.24 (2H, s), 0.96 (6H, s). LCMS (ES+) 439.2 (M+H)$^+$.

Example 55

5-Dimethyl-2-[(3S)-3-(3-(pyridin-4-yl)benzyl)morpholin-4-yl]-5,6-dihydro-1,3-benzothiazol-7(4H)-one The title compound was prepared from Example 51 and 4-pyridineboronic acid according to Method M and was isolated as a white solid (22%). δ$_H$ (DMSO-d$_6$) 8.62 (2H, dd, J 4.5 and 1.6 Hz), 7.82-7.57 (4H, m), 7.44-7.36 (2H, m), 4.27 (1H, br. s), 3.99-3.96 (1H, m), 3.80-3.51 (5H, m), 3.27-3.09 (2H, m), 2.51-2.49 (2H, m), 2.22 (2H, s), 0.94 (3H, s), 0.93 (3H, s). LCMS (ES+) 434.5 (M+H)$^+$.

Example 56

5,5-Dimethyl-2-[(3S)-3-(3-(pyrimidin-5-yl)benzyl) morpholin-4-yl]-5,6-dihydro-1,3-benzothiazol-7 (4H)-one The title compound was prepared from Example 51 and 3,5-pyrimidineboronic acid according to Method M and was isolated as a yellow solid (27%). δ$_H$ (DMSO-d$_6$) 9.18 (1H, s), 9.06 (2H, s), 7.65-7.61 (2H, m), 7.46-7.40 (2H, m), 4.28 (1H, br. s), 3.99-3.96 (1H, m), 3.81-3.55 (6H, m), 3.27-3.13 (3H, m), 2.22 (2H, s), 0.95 (3H, s), 0.92 (3H, s). LCMS (ES+) 435.3 (M+H)$^+$.

Example 57

Method U

2-[(3S)-3-(3-Bromobenzyl morpholin-4-yl]-7,7-dimethyl-5,6,7,8-tetrahydro-4H-[1,3]thiazolo[5,4-c]azepin-4-one To a stirred solution of Intermediate 69 (0.70 g, 2.75 mmol) and Intermediate 71 (0.65 g, 2.50 mmol) in THF (3 mL) was added DIPEA (0.90 mL, 5.20 mmol) and the reaction mixture was heated under microwave irradiation in a sealed tube to 180° C. for 3 h. On completion, the reaction mixture was concentrated in vacuo and partitioned between EtOAc (100 mL) and brine (100 mL). The organic phase was dried over MgSO$_4$, filtered and concentrated in vacuo. Purification by column chromatography (SiO$_2$, 1:1 hexanes/EtOAc) gave the title compound as a white solid (0.35 g, 33%). δ$_H$ (DMSO-d$_6$) 7.64 (1H, t, J 4.8 Hz), 7.45 (1H, s), 7.39-7.35 (1H, m), 7.25-7.21 (2H, m), 4.08 (1H, br. s), 3.94-3.88 (1H, m), 3.66-3.44 (5H, m), 3.07-3.00 (2H, m), 2.98-2.90 (2H, m), 2.63 (2H, s), 0.96 (6H, s). LCMS (ES+) 452.2 (M+H)$^+$.

Example 58

2-[(3S)-3-(Biphenyl-3-ylmethyl)morpholin-4-yl]-7,7-dimethyl-5,6,7,8-tetrahydro-4H-[1,3]thiazolo[5,4-c]azepin-4-one The title compound was prepared from Example 57 and phenylboronic acid according to Method M and was isolated as a yellow solid (15%). δ$_H$ (DMSO-d$_6$) 7.64-7.63 (3H, m), 7.61-7.39 (6H, m), 7.26-7.24 (1H, m), 4.09 (1H, br. s), 3.96-3.90 (1H, m), 3.72-3.62 (2H, m), 3.56-3.51 (2H, m), 3.16-2.98 (3H, m), 2.90-2.88 (2H, m), 2.62 (2H, s), 0.93 (6H, s). LCMS (ES+) 448.2 (M+H)$^+$.

Example 59

7,7-Dimethyl-2-[(3S)-3-(3-(pyridin-3-yl)benzyl) morpholin-4-yl]-5,6,7,8-tetrahydro-4H-[1,3]thiazolo [5,4-c]azepin-4-one The title compound was prepared from Example 57 and 3-pyridineboronic acid according to Method M and was isolated as a yellow solid (14%). δ$_H$ (DMSO-d$_6$) 8.84 (1H, d, J 2.3 Hz), 8.56 (1H, dd, J 4.7 and 1.6 Hz), 8.04-8.01 (1H, m), 7.63-7.40 (5H, m), 7.33-7.30 (1H, m), 4.12 (1H, t, J 6.8 Hz), 3.96-3.90 (1H, m), 3.74-3.51 (5H, m), 3.12-3.09 (2H, m), 2.88-2.87 (2H, m), 2.60-2.59 (2H, m), 0.92 (6H, s). LCMS (ES+) 449.5 (M+H)$^+$.

Example 60

5,5-Dimethyl-2-[3-(1H-pyrrolo[2,3-b]pyridin-3-ylmethyl)morpholin-4-yl]-5,6-dihydro-1,3-benzothiazol-7(4H)-one The title compound was prepared from Intermediate 15 and Intermediate 79 according to Method H and was isolated as a white solid (71%) after purification by column chromatography (SiO$_2$, 7:3 hexanes/EtOAc). δ$_H$ (CDCl$_3$) 9.88 (1H, br. s), 8.39 (1H, d, J 5.8 Hz), 8.33 (1H, d, J 3.4 Hz), 7.32 (1H, s), 7.24 (1H, dd, J 5.8 and 3.8 Hz), 4.25 (1H, br. s), 4.09 (1H, d, J 6.7 Hz), 3.85 (1H, d, J 8.9 Hz), 3.71 (2H, m), 3.56 (1H, d, J 7.8 Hz), 3.44 (1H, dd, J 10.1 and 8.5 Hz), 3.07 (1H, br. dd, J 10.3 and 2.5 Hz), 2.75 (2H, d, J 2.0 Hz), 2.44 (2H, s), 1.17 (6H, s). Exchangeable proton not observed. LCMS (ES+) 397.3 (M+H)$^+$.

Example 61

7,7-Dimethyl-2-[(3R)-3-(1H-indol-3-ylmethyl)morpholin-4-yl]-5,6,7,8-tetrahydro-4H-[1,3]thiazolo[5,4-c]azepin-4-one The title compound was prepared from Intermediate 71 and Intermediate 19 according to Method U and was isolated as a white solid (37%) after purification by column chromatography (SiO$_2$, 1:1 hexanes/EtOAc). $\delta_H$ (DMSO-d$_6$) 10.89 (1H, s), 7.80 (1H, d, J 7.8 Hz), 7.70 (1H, d, J 4.7 Hz), 7.34 (1H, d, J 7.8 Hz), 7.19 (1H, s), 7.08 (1H, t, J 7.4 Hz), 7.01 (1H, d, J 7.2 Hz), 4.07 (1H, s), 3.96 (1H, d, J 7.5 Hz), 3.70 (1H, d, J 11.5 Hz), 3.60 (1H, d, J 8.9 Hz), 3.58-3.36 (3H, m), 3.35-3.21 (1H, m), 2.95 (2H, d, J 4.4 Hz), 2.88 (1H, dd, J 13.7 and 3.7 Hz), 2.73 (2H, s), 0.99 (6H, s). LCMS (ES+) 411.0 (M+H)$^+$.

Example 62

7,7-Dimethyl-2-[3-(1H-pyrrolo[2,3-b]pyridin-3-ylmethyl)morpholin-4-yl]-5,6,7,8-tetrahydro-4H-[1,3]thiazolo[5,4-c]azepin-4-one The title compound was prepared from Intermediate 71 and Intermediate 79 according to Method U and was isolated as a white solid (51%) after purification by column chromatography (SiO$_2$, 4:6 hexanes/EtOAc). $\delta_H$ (CDCl$_3$) 11.39 (1H, br. s), 8.18 (2H, m), 7.68 (1H, br. t, J 4.9 Hz), 7.30 (1H, d, J 2.3 Hz), 7.06 (1H, dd, J 7.8 and 4.7 Hz), 4.13 (1H, m), 3.97 (1H, m), 3.70 (1H, d, J 11.6 Hz), 3.53 (3H, m), 3.22 (2H, m), 2.97 (1H, m), 2.93 (2H, d, J 5.1 Hz), 2.66 (2H, d, J 5.5 Hz), 0.98 (6H, s). LCMS (ES+) 412.0 (1+H)$^+$.

Example 63

5,5-Dimethyl-2-{(3R)-3-[(phenylthio)methyl]morpholin-4-yl}-5,6-dihydro-1,3-benzothiazol-7(4H)-one The title compound was prepared from Intermediate 15 and Intermediate 82 according to Method H and was isolated after purification by column chromatography (SiO$_2$, 1:1 hexanes/EtOAc) as a yellow solid (34%). $\delta_H$ (CDCl$_3$) 7.40 (2H, d, J 1.5 Hz), 7.24 (3H, m), 4.23 (1H, d, J 11.9 Hz), 4.04 (1H, m), 3.91 (1H, m), 3.54 (3H, m), 3.40 (1H, m), 3.29 (1H, dd, J 13.6 and 10.3 Hz), 3.14 (1H, dd, J 13.6 and 4.6 Hz), 2.59 (2H, s), 2.31 (2H, s), 1.35 (3H, s), 1.05 (3H, s). LCMS (ES+) 389.5 (M+H)$^+$.

Example 64

5,5-Dimethyl-2-[3-(phenoxymethyl)morpholin-4-yl]-5,6-dihydro-1,3-benzothiazol-7(4H)-one A mixture of Intermediate 83 (0.47 g, 1.66 mmol), and HCOONH$_4$ (1.00 g, 16.60 mmol) was stirred in EtOH (30 mL). Palladium on carbon (10 wt %) (0.06 g) was added carefully and the reaction mixture was heated to 60° C. for 16 h. The reaction mixture was then filtered through Celite® and concentrated in vacuo. The title compound was prepared from the reaction product and Intermediate 15 according to Method H and was isolated by column chromatography (SiO$_2$, 1:1 EtOAc/hexanes) as a white solid (0.03 g, 5%). $\delta_H$ (DMSO-d$_6$ @ 80° C.) 7.37-7.25 (2H, m), 6.97-6.92 (3H, m), 4.36-4.32 (2H, m), 4.26-4.18 (1H, m), 4.03-4.01 (1H, m), 3.94-3.92 (1H, m), 3.88-3.58 (2H, m), 3.57-3.48 (2H, m), 2.64 (2H, br. s), 2.32 (2H, s), 1.04 (6H, s). LCMS (ES+) 373.0 (M+H)$^+$.

Example 65

Method N 7,7-Dimethyl-2-(morpholin-4-yl)-5,6,7,8-tetrahydro-4H-[1,3]thiazolo[5,4-c]azepine-4-thione To a stirred solution of Example 43 (0.10 g, 0.36 mmol) in THF (10 mL) was added 2,4-bis(4-methoxyphenyl)-1,3-dithia-2,4-diphosphetane 2,4-disulphide (1.40 g, 0.36 mmol). The suspension was stirred for 7 days and then DCM (10 mL) and water (10 mL) were added, and the aqueous layer was extracted with DCM (3×15 mL). The combined organic layers were washed with water (3×20 mL), dried (MgSO$_4$), filtered and the solvent evaporated in vacuo. The oily residue was purified by column chromatography (SiO$_2$, 1:1 EtOAc/hexanes) and the resulting solid washed with Et$_2$O to give the title compound as a yellow solid (0.03 g, 31%). $\delta_H$ (DMSO-d$_6$) 9.38 (1H, br. s), 3.69 (4H, t, J 4.8 Hz), 3.51 (4H, t, J 4.8 Hz), 3.07 (2H, d, J 5.3 Hz), 2.67 (2H, s), 0.96 (6H, s). LCMS (ES+) 256.0 (M+H)$^+$.

Example 66

7,7-Dimethyl-2-[(3S)-3-(1H-indol-3-ylmethyl)morpholin-4-yl]-5,6,7,8-tetrahydro-4H-[1,3]thiazolo[5,4-c]azepine-4-thione The title compound was prepared as a yellow solid (17%) from Example 45 according to Method N. $\delta_H$ (DMSO-d$_6$) 10.88 (1H, s), 9.71 (1H, br. s), 7.81 (1H, d, J 7.8 Hz), 7.34 (1H, d, J 8.0 Hz), 7.18 (1H, d, J 2.0 Hz), 7.10-7.06 (1H, m), 7.02-6.97 (1H, m), 4.17 (1H, br. s), 3.96 (1H, d, J 7.0 Hz), 3.71 (1H, d, J 11.6 Hz), 3.68-3.40 (4H, m), 3.30-3.25 (1H, m), 3.08 (2H, d, J 5.0 Hz), 2.91 (1H, dd, J 10.1 and 3.9 Hz), 2.70 (2H, d, J 2.7 Hz), 0.98 (6H, s). LCMS (ES+) 427.0 (M+H)$^+$.

Example 67

5,5-Dimethyl-2-{3-[(pyridin-3-ylamino)methyl]morpholin-4-yl}-5,6-dihydro-1,3-benzothiazol-7(4H)-one To a stirred solution of Intermediate 62 (0.50 g, 1.60 mmol) and 3-aminopyridine (0.80 g, 8.50 mmol) in MeOH (30 mL) with 4 Å molecular sieves was added NaBH$_3$CN (0.13 g, 2.04 mmol) and a catalytic amount of AcOH. The reaction was then carried out according to Method I to give the title compound (0.05 g, 8%) as a white solid. $\delta_H$ (DMSO-d$_6$) 8.04 (1H, t, J 1.5 Hz), 7.77 (1H, t, J 2.9 Hz), 7.08 (2H, m), 6.16 (1H, t, J 6.3 Hz), 4.18 (1H, br. s), 3.89 (2H, m), 3.53 (5H, m), 3.29 (1H, m), 2.61 (2H, d, J 2.9 Hz), 2.30 (2H, s), 1.04 (6H, s). LCMS (ES+) 373.0 (M+H)$^+$.

Example 68

Method O 5,5-Dimethyl-2-[3-(piperidin-1-ylcarbonyl)morpholin-4-yl]-5,6-dihydro-1,3-benzothiazol-7(4H)-one To a stirred solution of Intermediate 64 (0.10 g, 0.32 mmol) in DCM (5 mL) was added 1-(3-dimethylaminopropyl)-3-ethylcarbodiimide (0.07 g, 0.38 mmol) and the reaction mixture was stirred at r.t. for 15 minutes. To this was added piperidine (0.03 g, 0.38 mmol) and the reaction mixture was stirred for 72 h at r.t. The solution was then concentrated in vacuo and purified by column chromatography (SiO$_2$, 1:1 EtOAc/hexanes) to give the title compound (0.04 g, 24%) as a white solid. δ$_H$ (DMSO-d$_6$) 5.08 (1H, br. s), 4.00 (1H, d, J 11.3 Hz), 3.95 (1H, dd, J 11.3 and 4.2 Hz), 3.82 (2H, m), 3.73-3.52 (4H, m), 3.39 (1H, br. m), 3.13 (1H, br. m), 2.69 (2H, s), 2.34 (2H, d, J 8.4 Hz), 1.75-1.32 (6H, br. m), 1.05 (3H, s), 1.03 (3H, s). LCMS (ES+) 378.1 (M+H)$^+$.

Example 69

2-[3-(3,4-Dihydroquinolin-1(2H)-ylcarbonyl)morpholin-4-yl]-5,5-dimethyl-5,6-dihydro-1,3-benzothiazol-7(4H)-one The title compound was prepared from Intermediate 64 and 3,4-dihydroquinoline according to Method O and was isolated as a white solid (50%) after purification by column chromatography (SiO$_2$, 2:3 EtOAc/hexanes). δ$_H$ (CDCl$_3$) 7.58 (1H, d, J 7.7 Hz), 7.15 (3H, m), 5.57 (1H, br. s), 4.26 (1H, m), 4.11-3.96 (2H, m), 3.69 (1H, br. m), 3.61-3.45 (2H, m), 3.39-3.18 (2H, m), 2.83 (1H, m), 2.68 (3H, m), 2.32 (2H, q, J 16.0 Hz), 2.13 (1H, m), 1.75 (1H, m), 1.09 (3H, s), 1.06 (3H, s). LCMS (ES+) 426.1 (M+H)$^+$.

Example 70

2-[3-(1-Benzothien-3-ylmethyl)morpholin-4-yl]-5,5-dimethyl-5,6-dihydro-1,3-benzothiazol-7(4H)-one The title compound was prepared from Intermediate 87 and Intermediate 15 according to Method H and was isolated as a white solid (81%) after purification by column chromatography (SiO$_2$, 2:3 EtOAc/hexanes). δ$_H$ (CDCl$_3$) 8.18 (1H, d, J 7.9 Hz), 7.87 (1H, d, J 7.8 Hz), 7.47 (2H, m), 7.29 (1H, s), 4.42 (2H, br. m), 4.09 (1H, br. d, J 5.5 Hz), 3.84 (1H, d, J 11.9 Hz), 3.69 (2H, m), 3.55 (2H, m), 3.18 (1H, dd, J 13.6 and 4.5 Hz), 2.72 (2H, d, J 4.1 Hz), 2.42 (2H, s), 1.16 (6H, s). LCMS (ES+) 412.8 (M+H)$^+$.

Example 71

2-[3-(Biphenyl-4-ylmethyl)morpholin-4-yl]-5,5-dimethyl-5,6-dihydro-1,3-benzothiazol-7(4H)-one The title compound was prepared from Example 29 and benzeneboronic acid according to Method L and was isolated as a white solid (68%) after purification by column chromatography (SiO$_2$, 4:1 EtOAc/hexanes). δ$_H$ (CDCl$_3$) 7.51 (3H, m), 7.38-7.21 (6H, m), 4.00-3.71 (4H, m), 3.64-3.51 (3H, m), 3.19 (1H, dd, J 12.6 and 10.5 Hz), 2.90 (1H, dd, J 12.6 and 4.5 Hz), 2.63 (2H, s), 2.32 (2H, s), 1.05 (6H, s). LCMS (ES+) 433.0 (M+H)$^+$.

Example 72

5,5-Dimethyl-2-[3-(4-(pyridin-3-yl)benzyl)moroholin-4-yl]-5,6-dihydro-1,3-benzothiazol-7(4H)-one The title compound was prepared from Example 29 and 3-pyridineboronic acid according to Method L and was isolated as a white solid (75%) after purification by column chromatography (SiO$_2$, 3:1 EtOAc/hexanes). δ$_H$ (CDCl$_3$) 8.79 (1H, br. s), 8.55 (1H, br. s), 7.87 (1H, d, J 7.9 Hz), 7.48 (2H, d, J 8.2 Hz), 7.36 (3H, d, J 8.1 Hz), 4.09-3.97 (2H, m), 3.84-3.74 (2H, m), 3.64-3.48 (3H, m), 3.20 (1H, dd, J 13.0 and 10.4 Hz), 2.93 (1H, dd, J 13.0 and 4.5 Hz), 2.63 (2H, s), 2.32 (2H, s), 1.05 (6H, s). LCMS (ES+) 434.0 (M+H)$^+$.

Example 73

Method P 5,5-Dimethyl-2-{3-[(5-methyl-1H-indol-3-yl)methyl]morpholin-4-yl}-5,6-dihydro-1,3-benzothiazole-7(4H)-thione To a stirred solution of Example 21 (0.06 g, 0.15 mmol) in THF (10 mL) at r.t. was added 2,4-bis(4-methoxyphenyl)-1,3-dithia-2,4-diphosphetane 2,4-disulphide (0.06 g, 0.15 mmol). The reaction mixture was stirred for 2 h and then poured into aqueous sat. NaHCO$_3$ solution (50 mL) and extracted with DCM (2×50 mL). The combined organic fractions were dried over MgSO$_4$, filtered and the solvent removed in vacuo to give the title compound (0.02 g, 35%) as an orange solid. δ$_H$ (DMSO-d$_6$) 10.33 (1H, br. s), 7.63 (1H, d, J 8.0 Hz), 7.10 (2H, m), 6.86 (1H, d, J 8.0 Hz), 4.16 (1H, br. s), 3.98 (1H, d, J 8.0 Hz), 3.73 (2H, m), 3.57 (3H, m), 3.31 (1H, m), 3.01 (1H, m), 2.74 (2H, s), 2.57 (2H, d, J 5.6 Hz), 2.40 (3H, s), 1.04 (6H, s). LCMS (ES+) 426.9 (M+H)$^+$.

Example 74

5,5-Dimethyl-2-[3-(1-naphthylmethyl)morpholin-4-yl]-5,6-dihydro-1,3-benzothiazole-7(4H)-thione The title compound was prepared from Example 16 according to Method P and was isolated as an orange solid (77%) that required no further purification. δ$_H$(CDCl$_3$) 8.41 (1H, d, J 8.3 Hz), 7.78 (1H, d, J 8.7 Hz), 7.70 (1H, dd, J 7.0 and 2.3 Hz), 7.57-7.42 (2H, m), 7.36 (2H, m), 4.46 (1H, br. m), 4.05 (1H, d, J 10.8 Hz), 3.73-3.55 (5H, m), 3.42-3.31 (2H, m), 2.77 (2H, s), 2.55 (2H, d, J 5.4 Hz), 1.05 (6H, s). LCMS (ES+) 423.8 (M+H)$^+$.

Example 75

2-[3-(1-Benzothien-3-ylmethyl morpholin-4-yl]-5,5-dimethyl-5,6-dihydro-1,3-benzothiazole-7(4H)-thione The title compound was prepared from Example 70 according to Method P and was isolated as an orange solid (72%) that required no further purification. δ$_H$ (CDCl$_3$) 8.11 (1H, br. d, J 7.6 Hz), 7.93 (1H, d, J 7.6 Hz), 7.51-7.32 (3H, m), 4.07 (1H, m), 3.81 (2H, m), 3.64 (2H, m), 3.47-3.25 (4H, m), 2.66 (2H, s), 2.51 (2H, m), 0.96 (3H, s), 0.94 (3H, s). LCMS (ES+) 428.8 (M+H)$^+$.

Example 76

N-{[4-(5,5-Dimethyl-7-oxo-4,5,6,7-tetrahydro-1,3-benzothiazol-2-yl)morpholin-3-yl]methyl}benzenesulfonamide The title compound was prepared from Intermediate 89 and Intermediate 15 according to Method H and was isolated as a white solid (52%) after purification by column chromatography (SiO$_2$, 2:3 EtOAc/hexanes). δ$_H$ (CDCl$_3$) 7.83 (2H, m), 7.74-7.48 (3H, m), 5.41 (1H, br. s), 4.39 (1H, br. m), 3.95

(2H, d, J 12.1 Hz), 3.70-3.31 (6H, m), 2.71 (2H, d, J 4.9 Hz), 2.43 (2H, s), 1.19 (3H, s), 1.11 (3H, s). LCMS (ES+) 435.8 (M+H)$^+$.

Example 77

2-[3-(1-Benzothien-2-ylmethyl)morpholin-4-yl]-5,6-dihydro-1,3-benzothiazol-7(4H)-one The title compound was prepared from Intermediate 95 and Intermediate 15 according to Method H and was isolated as a white solid (71%) after purification by column chromatography (SiO$_2$, 2:3 EtOAc/hexanes). δ$_H$ (CDCl$_3$) 7.69 (1H, d, J 7.1 Hz), 7.61 (1H, dd, J 7.1 and 1.9 Hz), 7.25 (2H, m), 7.07 (1H, s), 4.14 (1H, br. m), 3.96 (1H, m), 3.87 (1H, d, J 11.9 Hz), 3.76 (1H, d, J 11.4 Hz), 3.65-3.42 (4H, m), 3.13 (1H, dd, J 14.1 and 4.7 Hz), 2.59 (2H, d, J 3.3 Hz), 2.30 (2H, s), 1.04 (3H, s), 1.01 (3H, s). LCMS (ES+) 413.2 (M+H)$^+$.

Example 78

7,7-Dimethyl-2-[3-(isoquinolin-4-ylmethyl)morpholin-4-yl]-7,7-dimethyl 5,6,7,8-tetrahydro-4H-[1,3]thiazolo[5,4-e]azepin-4-one The title compound was prepared from Intermediate 99 and Intermediate 71 according to Method U and was isolated as a white solid (23%) after purification by column chromatography (SiO$_2$, 1:4 hexanes/EtOAc). δ$_H$ (CDCl$_3$) 9.16 (1H, s), 8.64 (1H, d, J=8.6 Hz), 8.50 (1H, s), 8.00 (1H, d, J=8.0 Hz), 7.78 (1H, dt, J 6.9 and 1.3 Hz), 7.63 (1H, dt, J 8.0 and 0.9 Hz), 5.79 (1H, br. s), 4.44 (1H, br. d, J=11.0 Hz), 4.10 (1H, m), 3.75-3.43 (6H, m), 3.35 (1H, dd, J 13.1 and 3.9 Hz), 3.12 (2H, d, J=5.2 Hz), 2.88 (2H, d, J=2.0 Hz), 1.14 (6H, s). LCMS (ES+) 423.3 (M+H)$^+$.

Example 79

7,7-Dimethyl-2-[3-(quinolin-5-ylmethyl)morpholin-4-yl]-5,6,7,8-tetrahydro-4H-[1,3]thiazolo[5,4-c]azepin-4-one The title compound was prepared from Intermediate 103 and Intermediate 71 according to Method U and was isolated as a white solid (42%) after purification by column chromatography (SiO$_2$, EtOAc). δ$_H$ (CDCl$_3$) 8.96 (1H, d, J 8.4 Hz), 8.86 (1H, dd, J 4.1 and 1.5 Hz), 7.95 (1H, d, J 8.4 Hz), 7.59 (1H, t, J 8.4 Hz), 7.45-7.35 (2H, m), 5.91 (1H, br. t, J 4.9 Hz), 4.26 (1H, br. d, J 10.9 Hz), 4.06 (1H, m), 3.65-3.30 (7H, m), 3.06 (2H, d, J 5.0 Hz), 2.78 (2H, d, J 5.4 Hz), 1.07 (3H, s), 1.06 (3H, s). LCMS (ES+) 423.3 (M+H)$^+$.

Example 80

7,7-Dimethyl-2-[3-(quinolin-8-ylmethyl)morpholin-4-yl]-5,6,7,8-tetrahydro-4H-[1,3]thiazolo[5,4-c]azepin-4-one The title compound was prepared from Intermediate 107 and Intermediate 71 according to Method U and was isolated as a white solid (39%) after purification by column chromatography (SiO$_2$, 4:1 EtOAc/DCM). δ$_H$(CDCl$_3$) 9.01 (1H, dd, J 4.1 and 1.8 Hz), 8.12 (1H, dd, J 8.2 and 1.8 Hz), 7.65 (2H, m), 7.41 (2H, m), 5.83 (1H, br. m), 4.44 (1H, br. m), 4.08 (1H, m), 3.95-3.54 (7H, m), 3.03 (2H, m), 2.60 (2H, ABq, J 17.7 Hz), 1.04 (6H, s). LCMS (ES+) 423.3 (M+H)$^+$.

Example 81

5,5-Dimethyl-2-[3-(quinolin-8-ylmethyl)morpholin-4-yl]-5,6-dihydro-1,3-benzothiazol-7(4H)-one The title compound was prepared from Intermediate 107 and Intermediate 15 according to Method H and was isolated as a white solid (71%) after purification by column chromatography (SiO$_2$, 1:1 EtOAc/DCM). δ$_H$ (CDCl$_3$) 9.00 (1H, dd, J 4.2 and 1.8 Hz), 8.09 (1H, dd, J 8.3 and 1.7 Hz), 7.64 (2H, m), 7.42 (2H, m), 4.49 (1H, br. m), 4.05 (2H, m), 3.94-3.79 (4H, m), 3.64 (2H, dt, J 11.5 and 3.3 Hz), 2.43 (2H, ABq, J 16.9 Hz), 2.29 (2H, s), 1.06 (3H, s), 1.04 (3H, s). LCMS (ES+) 408.0 (M+H)$^+$.

Example 82

5,5-Dimethyl-2-[(3S)-3-(3-(pyrrol din-1-yl)benzyl)morpholin-4-yl]-5,6-dihydro-1,3-benzothiazol-7(4H)-one To a schlenk tube was added Example 51 (0.08 g, 0.18 mmol), K$_2$CO$_3$ (0.06 g, 0.45 mmol), Pd$_2$(dba)$_3$ (0.01 g, 0.01 mmol) and 2-dicyclohexylphosphino-2',4',6'-tri-isopropyl-1,1'-biphenyl (0.02 g, 0.05 mmol). To this was added $^t$BuOH (1.5 mL) and pyrrolidine (0.02 g, 0.02 mL, 0.27 mmol). The schlenk tube was sealed and the reaction mixture was heated to 110° C. for 16 h. The dark solution was then dissolved in EtOAc (15 mL) and washed with water (10 mL) and brine (10 mL), dried over MgSO$_4$, filtered and concentrated in vacuo into a dark oil. The crude material was purified by column chromatography (SiO$_2$, 1:1 hexanes/EtOAc) to give the title compound as a white solid (0.07 g, 92%). δ$_H$ (CDCl$_3$) 7.18 (1H, t, J 7.7 Hz), 6.62 (1H, d, J 7.4 Hz), 6.49 (2H, br. m), 4.04 (1H, m), 3.95 (2H, br. m), 3.89 (1H, d, J 11.9 Hz), 3.71-3.52 (3H, m), 3.31 (3H, m), 3.18 (1H, m), 2.88 (1H, dd, J 12.8 and 3.8 Hz), 2.72 (2H, s), 2.42 (2H, s), 2.02 (3H, br. m), 1.68 (2H, br. s), 1.16 (6H, s). LCMS (ES+) 426.3 (M+H)$^+$.

Example 83

2-{3-[(6-Bromopyridin-2-yl)methyl]morpholin-4-yl}-5,5-dimethyl-5,6-dihydro-1,3-benzothiazol-7(4H)-one The title compound was prepared from Intermediate 109 and Intermediate 15 according to Method H and was isolated as a white solid (85%) after purification by column chromatography (SiO$_2$, 1:1 EtOAc/DCM). δ$_H$ (CDCl$_3$) 7.34 (1H, t, J 7.5 Hz), 7.22 (1H, d, J 7.5 Hz), 7.07 (1H, d, J 7.4 Hz), 4.40 (1H, br. m), 3.97 (1H, d, J 7.1 Hz), 3.82 (1H, d, J 11.8 Hz), 3.61 (4H, m), 3.20 (2H, d, J 7.4 Hz), 2.54 (2H, d, J 3.2 Hz), 2.28 (2H, s), 1.03 (3H, s), 1.02 (3H, s). LCMS (ES+) 436.2 and 438.2 (M+H)$^+$.

Example 84

5,5-Dimethyl-2-{3-[(6-phenylpyridin-2-yl)methyl]morpholin-4-yl}-5,6-dihydro-1,3-benzothiazol-7(4H)-one Pd(OAc)$_2$ (0.002 g, 0.006 mmol) and 2-dicyclohexylphosphino-2',6'-dimethoxybiphenyl (0.007 g, 0.016 mmol) were added to a stirred solution of Example 83 (0.140 g, 0.320 mmol), phenylboronic acid (0.059 g, 0.480 mmol) and K$_3$PO$_4$ (0.136 g, 0.640 mmol) in toluene (1.5 mL), and the reaction mixture was heated at 100° C. for 2 h. On completion, the reaction mixture was concentrated in vacuo and partitioned between EtOAc (100 mL) and brine (100 mL). The organic phase was dried over MgSO$_4$, filtered and concentrated in vacuo. Purification by column chromatography (SiO$_2$, 1:1 DCM/EtOAc) gave the title compound as a white solid (0.058 g, 42%). δ$_H$(CDCl$_3$) 8.03 (2H, m), 7.66 (1H, t, J 7.4 Hz), 7.57 (1H, m), 7.44 (3H, m), 7.18 (1H, d, J 7.4 Hz), 4.47 (1H, br. m), 4.10-3.99 (3H, m), 3.78-3.65 (3H, m), 3.45 (1H, dd, J 13.5 and 8.9 Hz), 3.29 (1H, dd, J 13.5 and 5.9 Hz), 2.62 (2H, s), 2.35 (2H, s), 1.09 (3H, s), 1.08 (3H, s). LCMS (ES+) 434.0 (M+H)$^+$.

Example 85

Method V 5,5-Dimethyl-2-{(3S)-3-[(2'-methylbiphenyl-3-yl)methyl]morpholin-4-yl}-5,6-dihydro-1,3-benzothiazol-7(4H)-one To a mixture of polystyrene Pd(PPh$_3$)$_4$ (0.008 g, 0.001 mmol) and (2-methylphenyl)boronic acid (0.003 g, 0.023 mmol) was added a solution of Example 51 (0.007 g, 0.015 mmol) in 1,4-dioxane (0.400 mL) and aqueous K$_2$CO$_3$ (2M, 0.100 mL). The reaction mixture was heated under microwave irradiation in a sealed tube to 125° C. for 10 minutes and was then filtered and washed with 1,4-dioxane. The filtrate was concentrated in vacuo and the title compound was obtained in 95% purity after purification by preparative LC. LCMS (ES+) 447.0 (M+H)$^+$, RT 4.60 minutes.

Example 86

5,5-Dimethyl-2-{(3S)-3-[(3'-methoxybiphenyl-3-yl)methyl]morpholin-4-yl}-5,6-dihydro-1,3-benzothiazol-7(4H)-one The title compound was prepared from Example 51 and (3-methoxyphenyl)-boronic acid according to Method V and was isolated in 98% purity after purification by preparative LC. LCMS (ES+) 463.0 (M+H)$^+$, RT 4.34 minutes.

Example 87

5,5-Dimethyl-2-[(3S)-3-{[2'-(trifluoromethyl)biphenyl-3-yl]methyl}morpholin-4-yl]-5,6-dihydro-1,3-benzothiazol-7(4H)-one The title compound was prepared from Example 51 and (2-trifluoromethyl-phenyl)boronic acid according to Method V and was isolated in 98% purity after purification by preparative LC. LCMS (ES+) 501.0 (M+H)$^+$, RT 4.59 minutes.

Example 88

2{(3S)-3-[(2'-Chlorobiphenyl-3-yl)methyl]morpholin-4-yl}-5,5-dimethyl-5,6-dihydro-1,3-benzothiazol-7(4H)-one The title compound was prepared from Example 51 and (2-chlorophenyl)boronic acid according to Method V and was isolated in 96% purity after purification by preparative LC. LCMS (ES+) 467.0 (M+H)$^+$, RT 4.54 minutes.

Example 89

5,5-Dimethyl-2-{(3S)-3-[3-(1-naphthyl)benzyl]morpholin-4-yl}-5,6-dihydro-1,3-benzothiazol-7(4H)-one The title compound was prepared from Example 51 and 1-naphthylboronic acid according to Method V and was isolated in 98% purity after purification by preparative LC. LCMS (ES+) 483.0 (M+H)$^+$, RT 4.77 minutes.

Example 90

5,5-Dimethyl-2-{(3S)-3-[3-(2-naphthyl)benzyl]morpholin-4-yl}-5,6-dihydro-1,3-benzothiazol-7(4H)-one The title compound was prepared from Example 51 and 2-naphthylboronic acid according to Method V and was isolated in 96% purity after purification by preparative LC. LCMS (ES+) 483.0 (M+H)$^+$, RT 4.78 minutes.

Example 91

2-{(3S)-3-[(3'-Chlorobiphenyl-3-yl)methyl]morpholin-4-yl}-5,5-dimethyl-5,6-dihydro-1,3-benzothiazol-7(4H)-one The title compound was prepared from Example 51 and (3-chlorophenyl)boronic acid according to Method V and was isolated in 100% purity after purification by preparative LC. LCMS (ES+) 467.0 (M+H)$^+$, RT 4.68 minutes.

Example 92

5,5-Dimethyl-2-{(3S)-3-[(3'-fluorobiphenyl-3-yl)methyl]morpholin-4-yl}-5,6-dihydro-1,3-benzothiazol-7(4H)-one The title compound was prepared from Example 51 and (3-fluorophenyl)boronic acid according to Method V and was isolated in 95% purity after purification by preparative LC. LCMS (ES+) 451.0 (M+H)$^+$, RT 4.43 minutes.

Example 93

5,5-Dimethyl-2-{(3S)-3-[(2'-fluorobiphenyl-3-yl)methyl]morpholin-4-yl}-5,6-dihydro-1,3-benzothiazol-7(4H)-one The title compound was prepared from Example 51 and (2-fluorophenyl)boronic acid according to Method V and was isolated in 98% purity after purification by preparative LC. LCMS (ES+) 451.0 (M+H)$^+$, RT 4.39 minutes.

Example 94

2-{(3S)-3-[(2',6'-Difluorobiphenyl-3-yl)methyl]morpholin-4-yl}-5,5-dimethyl-5,6-dihydro-1,3-benzothiazol-7(4H)-one The title compound was prepared from Example 51 and (2,6-difluorophenyl)-boronic acid according to Method V and was isolated in 97% purity after purification by preparative LC. LCMS (ES+) 469.0 (M+H)$^+$, RT 4.34 minutes.

Example 95

2-{(3S)-3-[(3',4'-Dichlorobiphenyl-3-yl)methyl]morpholin-4-yl}-5,5-dimethyl-5,6-dihydro-1,3-benzothiazol-7(4H)-one The title compound was prepared from example 51 and (3,4-dichlorophenyl)-boronic acid according to Method V and was isolated in 98% purity after purification by preparative LC. LCMS (ES+) 501.0 and 503.0 (M+H)$^+$, RT 4.92 minutes.

Example 96

5,5-Dimethyl-2-[(3S)-3-{[4'-(methylthio)biphenyl-3-yl]methyl}morpholin-4-yl]-5,6-dihydro-1,3-benzothiazol-7(4H)-one The title compound was prepared from Example 51 and [4-(methylthio)-phenyl]boronic acid according to Method V and was isolated in 97% purity after purification by preparative LC. LCMS (ES+) 479.0 (M+H)$^+$, RT 4.58 minutes.

Example 97

2-{(3S)-3-[3-(1-Benzofuran-2-yl)benzyl]morpholin-4-yl}-5,5-dimethyl-5,6-dihydro-1,3-benzothiazol-7(4H)-one The title compound was prepared from Example 51 and 1-benzofuran-2-ylboronic acid according to Method V and was isolated in 93% purity after purification by preparative LC. LCMS (ES+) 473.0 (M+H)$^+$, RT 4.66 minutes.

Example 98

2-{(3S)-3-[3-(1-Benzothien-2-yl)benzyl]morpholin-4-yl}-5,5-dimethyl-5,6-dihydro-1,3-benzothiazol-7(4H)-one The title compound was prepared from Example 51 and 1-benzothien-2-ylboronic acid according to Method V and was isolated in 96% purity after purification by preparative LC. LCMS (ES+) 489.0 (M+H)$^+$, RT 4.77 minutes.

Example 99

5,5-Dimethyl-2-{(3S)-3-[(3'-methylbiphenyl-3-yl)methyl]morpholin-4-yl}-5,6-dihydro-1,3-benzothiazol-7(4H)-one The title compound was prepared from Example 51 and (3-methylphenyl)boronic acid according to Method V and was isolated in 99% purity after purification by preparative LC. LCMS (ES+) 447.0 (M+H)$^+$, RT 4.63 minutes.

Example 100

5,5-Dimethyl-2-{(3S)-3-[(2'-methoxybiphenyl-3-yl)methyl]morpholin-4-yl}-5,6-dihydro-1,3-benzothiazol-7(4H)-one The title compound was prepared from Example 51 and (2-methoxyphenyl)-boronic acid according to Method V and was isolated in 100% purity after purification by preparative LC. LCMS (ES+) 463.0 (M+H)$^+$, RT 4.38 minutes.

Example 101

5,5-Dimethyl-2-{(3S)-3-[3-(thien-2-yl)benzyl]morpholin-4-yl}-5,6-dihydro-1,3-benzothiazol-7(4H)-one The title compound was prepared from Example 51 and 2-thienylboronic acid according to Method V and was isolated in 99% purity after purification by preparative LC. LCMS (ES+) 439.0 (M+H)$^+$, RT 4.31 minutes.

Example 102

5,5-Dimethyl-2-{(3S)-3-[(3'-ethoxybiphenyl-3-yl)methyl]morpholin-4-yl}-5,6-dihydro-1,3-benzothiazol-7(4H)-one The title compound was prepared from Example 51 and (3-ethoxyphenyl)boronic acid according to Method V and was isolated in 97% purity after purification by preparative LC. LCMS (ES+) 477.0 (M+H)$^+$, RT 4.56 minutes.

Example 103

5,5-Dimethyl-2-{(3S)-3-[3-(4-methylthien-2-yl)benzyl]morpholin-4-yl}-5,6-dihydro-1,3-benzothiazol-7(4H)-one The title compound was prepared from Example 51 and (4-methyl-2-thienyl)-boronic acid according to Method V and was isolated in 95% purity after purification by preparative LC. LCMS (ES+) 453.2 (M+H)$^+$, RT 4.56 minutes.

Example 104

2-{(3S)-3-[3-(5-Acetylthien-2-yl)benzyl]morpholin-4-yl}-5,5-dimethyl-5,6-dihydro-1,3-benzothiazol-7(4H)-one The title compound was prepared from Example 51 and (5-acetyl-2-thienyl)-boronic acid according to Method V and was isolated in 75% purity after purification by preparative LC. LCMS (ES+) 481.0 (M+H)$^+$, RT 3.32 minutes.

Example 105

2-{(3)-3-[3-(1-Benzothien-3-yl)benzyl]morpholin-4-yl}-5,5-dimethyl-5,6-dihydro-1,3-benzothiazol-7(4H)-one The title compound was prepared from Example 51 and 1-benzothien-3-ylboronic acid according to Method V and was isolated in 97% purity after purification by preparative LC. LCMS (ES+) 489.0 (M+H)$^+$, RT 4.73 minutes.

Example 106

5,5-Dimethyl-2-{(3S)-3-[(4'-methylbiphenyl-3-yl)methyl]morpholin-4-yl}-5,6-dihydro-1,3-benzothiazol-7(4H)-one The title compound was prepared from Example 51 and (4-methylphenyl)boronic acid according to Method V and was isolated in 99% purity after purification by preparative LC. LCMS (ES+) 447.0 (M+H)$^+$, RT 4.64 minutes.

Example 107

2-{(3S)-3-[(3'-Acetylbiphenyl-3-yl)methyl]morpholin-4-yl}-5,5-dimethyl-5,6-dihydro-1,3-benzothiazol-7(4H)-one The title compound was prepared from Example 51 and (3-acetylphenyl)boronic acid according to Method V and was isolated in 92% purity after purification by preparative LC. LCMS (ES+) 475.0 (M+H)$^+$, RT 4.05 minutes.

Example 108

2-{(3S)-3-[(4'-Acetylbiphenyl-3-yl)methyl]morpholin-4-yl}-5,5-dimethyl-5,6-dihydro-1,3-benzothiazol-7(4H)-one The title compound was prepared from Example 51 and (4-acetylphenyl)boronic acid according to Method V and was isolated in 91% purity after purification by preparative LC. LCMS (ES+) 475.0 (M+H)$^+$, RT 4.01 minutes.

Example 109

2-{(3S)-3-[(2'-Bromobiphenyl-3-yl)methyl)morpholin-4-yl}-5,5-dimethyl-5,6-dihydro-1,3-benzothiazol-7(4H)-one The title compound was prepared from Example 51 and (2-bromophenyl)boronic acid according to Method V and was isolated in 83% purity after purification by preparative LC. LCMS (ES+) 511.0 and 513.0 (M+H)$^+$, RT 4.60 minutes.

Example 110

2-{(3S)-3-[(3'-Bromobiphenyl-3-yl)methyl]morpholin-4-yl}-5,5-dimethyl-5,6-dihydro-1,3-benzothiazol-7(4H)-one The title compound was prepared from Example 51 and (3-bromophenyl)boronic acid according to Method V and was isolated in 79% purity after purification by preparative LC. LCMS (ES+) 511.0 and 513.0 (M+H)$^+$, RT 4.74 minutes.

Example 111

2-{(3S)-3-[(4'-Bromobiphenyl-3-yl)methyl]morpholin-4-yl}-5,5-dimethyl-5,6-dihydro-1,3-benzothiazol-7(4H)-one The title compound was prepared from Example 51 and (4-bromophenyl)boronic acid according to Method V and was isolated in 88% purity after purification by preparative LC. LCMS (ES+) 511.0 and 513.0 (M+H)$^+$, RT 4.74 minutes.

Example 112

2-[(3S)-3-{[3',5'-Bis(trifluoromethyl)biphenyl-3-yl]methyl}morpholin-4-yl]-5,5-dimethyl-5,6-dihydro-1,3-benzothiazol-7(4H)-one The title compound was prepared from Example 51 and [3,5-bis(trifluoromethyl)-phenyl]boronic acid according to Method V and was isolated in 100% purity after purification by preparative LC. LCMS (ES+) 569.0 (M+H)$^+$, RT 4.95 minutes.

Example 113

2-{(3S)-3-[(4'-Chlorobiphenyl-3-yl)methyl]morpholin-4-yl}-5,5-dimethyl-5,6-dihydro-1,3-benzothiazol-7(4H)-one The title compound was prepared from Example 51 and (4-chlorophenyl)boronic acid according to Method V and was isolated in 100% purity after purification by preparative LC. LCMS (ES+) 467.0 (M+H)$^+$, RT 4.68 minutes.

Example 114

2-{(3S)-3-[(2',5'-Dichlorobiphenyl-3-yl)methyl]morpholin-4-yl}-5,5-dimethyl-5,6-dihydro-1,3-benzothiazol-7(4H)-one The title compound was prepared from Example 51 and (2,5-dichlorophenyl)-boronic acid according to Method V and was isolated in 94% purity after purification by preparative LC. LCMS (ES+) 501.0 and 503.0 (M+H)$^+$, RT 4.84 minutes.

Example 115

2-{(3S)-3-[(3',5'-Difluorobiphenyl-3-yl)methyl]morpholin-4-yl}-5,5-dimethyl-5,6-dihydro-1,3-benzothiazol-7(4H)-one The title compound was prepared from Example 51 and (3,5-difluorophenyl)-boronic acid according to Method V and was isolated in 92% purity after purification by preparative LC. LCMS (ES+) 469.0 (M+H)$^+$, RT 4.52 minutes.

Example 116

2-{(3S)-3-[(3',4'-Dimethoxybiphenyl-3-yl)methyl]morpholin-4-yl}-5,5-dimethyl-5,6-dihydro-1,3-benzothiazol-7(4H)-one The title compound was prepared from Example 51 and (3,4-dimethoxyphenyl)-boronic acid according to Method V and was isolated in 99% purity after purification by preparative LC. LCMS (ES+) 493.0 (M+H)$^+$, RT 4.02 minutes.

Example 117

2-{(3S)-3-[(2',3'-Dimethylbiphenyl-3-yl)methyl]morpholin-4-yl}-5,5-dimethyl-5,6-dihydro-1,3-benzothiazol-7(4H)-one The title compound was prepared from Example 51 and (2,3-dimethylphenyl)-boronic acid according to Method V and was isolated in 100% purity after purification by preparative LC. LCMS (ES+) 461.0 (M+H)$^+$, RT 4.77 minutes.

Example 118

2-{(3S)-3-[(3',5'-Dimethylbiphenyl-3-yl)methyl]morpholin-4-yl}-5,5-dimethyl-5,6-dihydro-1,3-benzothiazol-7(4H)-one The title compound was prepared from Example 51 and (3,5-dimethylphenyl)-boronic acid according to Method V and was isolated in 99% purity after purification by preparative LC. LCMS (ES+) 461.0 (M+H)$^+$, RT 4.85 minutes.

Example 119

2-{(3S)-3-[(2',5'-Dimethylbiphenyl-3-yl)methyl]morpholin-4-yl}-5,5-dimethyl-5,6-dihydro-1,3-benzothiazol-7(4H)-one The title compound was prepared from Example 51 and (2,5-dimethylphenyl)-boronic acid according to Method V and was isolated in 98% purity after purification by preparative LC. LCMS (ES+) 461.0 (M+H)⁺, RT 4.81 minutes.

Example 120

5,5-Dimethyl-2-{(3S)-3-[(4'-fluoro-3'-methylbiphenyl-3-yl)methyl]morpholin-4-yl}-5,6-dihydro-1,3-benzothiazol-7(4H)-one The title compound was prepared from Example 51 and (4-fluoro-3-methyl-phenyl)boronic acid according to Method V and was isolated in 100% purity after purification by preparative LC. LCMS (ES+) 465.0 (+H)⁺, RT 4.65 minutes.

Example 121

5,5-Dimethyl-2-{(3S)-3-[(4'-fluorobiphenyl-3-yl)methyl]morpholin-4-yl}-5,6-dihydro-1,3-benzothiazol-7(4H)-one The title compound was prepared from Example 51 and (4-fluorophenyl)boronic acid according to Method V and was isolated in 100% purity after purification by preparative LC. LCMS (ES+) 451.0 (M+H)⁺, RT 4.41 minutes.

Example 122

5,5-Dimethyl-2-{(3S)-3-[(4'-methoxybiphenyl-3-yl)methyl]morpholin-4-yl}-5,6-dihydro-1,3-benzothiazol-7(4H)-one The title compound was prepared from Example 51 and (4-methoxyphenyl)-boronic acid according to Method V and was isolated in 99% purity after purification by preparative LC. LCMS (ES+) 463.0 (+H)⁺, RT 4.32 minutes.

Example 123

2-{(3S)-3-[3-(1,3-benzodioxol-5-yl)benzyl]morpholin-4-yl}-5,5-dimethyl-5,6-dihydro-1,3-benzothiazol-7(4H)-one The title compound was prepared from Example 51 and 1,3-benzodioxol-5-ylboronic acid according to Method V and was isolated in 98% purity after purification by preparative LC. LCMS (ES+) 477.0 (M+H)⁺, RT 4.24 minutes.

Example 124

5,5-Dimethyl-2-{(3S)-3-[(4'-phenoxybiphenyl-3-yl)methyl]morpholin-4-yl}-5,6-dihydro-1,3-benzothiazol-7(4H)-one The title compound was prepared from Example 51 and (4-phenoxyphenyl)-boronic acid according to Method V and was isolated in 97% purity after purification by preparative LC. LCMS (ES+) 525.0 (M+H)⁺, RT 4.30 minutes.

Example 125

5,5-Dimethyl-2-[(3S)-3-{[3'-(trifluoromethyl)biphenyl-3-yl]methyl}morpholin-4-yl]-5,6-dihydro-1,3-benzothiazol-7(4H)-one The title compound was prepared from Example 51 and (3-trifluoromethyl-phenyl)boronic acid according to Method V and was isolated in 99% purity after purification by preparative LC. LCMS (ES+) 501.0 (M+H)⁺, RT 4.68 minutes.

Example 126

2-{(3S)-3-[(3',4'-Difluorobiphenyl-3-yl)methyl]morpholin-4-yl}-5,5-dimethyl-5,6-dihydro-1,3-benzothiazol-7(4H)-one The title compound was prepared from Example 51 and (3,4-difluorophenyl)-boronic acid according to Method V and was isolated in 94% purity after purification by preparative LC. LCMS (ES+) 469.0 (M+H)⁺, RT 4.45 minutes.

Example 127

N-(3'-{[(3S)-4-(5,5-Dimethyl-7-oxo-4,5,6,7-tetrahydro-1,3-benzothiazol-2-yl)morpholin-3-yl]methyl}biphenyl-3-yl)acetamide The title compound was prepared from Example 51 and (3-acetamidophenyl)-boronic acid according to Method V and was isolated in 94% purity after purification by preparative LC. LCMS (ES+) 490.0 (M+H)⁺, RT 3.52 minutes.

Example 128

2-{(3S)-3-[(3'-Aminobiphenyl-3-yl)methyl]morpholin-4-yl}-5,5-dimethyl-5,6-dihydro-1,3-benzothiazol-7(4H)-one The title compound was prepared from Example 51 and (3-aminophenyl)boronic acid according to Method V and was isolated in 86% purity after purification by preparative LC. LCMS (ES+) 448.0 (M+H)⁺, RT 3.20 minutes.

Example 129

3'-{[(3S)-4-(5,5-Dimethyl-7-oxo-4,5,6,7-tetrahydro-1,3-benzothiazol-2-yl)morpholin-3-yl]methyl}biphenyl-4-carbonitrile The title compound was prepared from Example 51 and (4-cyanophenyl)boronic acid according to Method V and was isolated in 98% purity after purification by preparative LC. LCMS (ES+) 458.0 (M+H)⁺, RT 4.08 minutes.

Example 130

5,5-Dimethyl-2-[(3S)-3-{[3'-(hydroxymethyl)biphenyl-3-yl]methyl}morpholin-4-yl]-5,6-dihydro-1,3-benzothiazol-7(4H)-one The title compound was prepared from Example 51 and [3-(hydroxymethyl)-phenyl]boronic acid according to Method V and was isolated in 80% purity after purification by preparative LC. LCMS (ES+) 463.0 (M+H)⁺, RT 3.59 minutes.

Example 131

5,5-Dimethyl-2-[(3S)-3-{[2'-(hydroxymethyl)biphenyl-3-yl]methyl}morpholin-4-yl]-5,6-dihydro-1,3-benzothiazol-7(4H)-one The title compound was prepared from Example 51 and [2-(hydroxymethyl)-phenyl]boronic acid according to Method V and was isolated in 74% purity after purification by preparative LC. LCMS (ES+) 463.0 (M+H)$^+$, RT 3.68 minutes.

Example 132

5,5-Dimethyl-2-[(3S)-3-{[3'-(trifluoromethoxy)biphenyl-3-yl]methyl}morpholin-4-yl]-5,6-dihydro-1,3-benzothiazol-7(4H)-one The title compound was prepared from Example 51 and [3-(trifluoromethoxy)-phenyl]boronic acid according to Method V and was isolated in 99% purity after purification by preparative LC. LCMS (ES+) 517.0 (M+H)$^+$, RT 4.77 minutes.

Example 133

5,5-Dimethyl-2-{(3S)-3-[3-(6-methoxypyridin-3-yl)benzyl]morpholin-4-yl}-5,6-dihydro-1,3-benzothiazol-7(4H)-one The title compound was prepared from Example 51 and (6-methoxypyridin-3-yl)boronic acid according to Method V and was isolated in 93% purity after purification by preparative LC. LCMS (ES+) 464.0 (M+H)$^+$, RT 4.04 minutes.

Example 134

N-(3'-{[(3S)-4-(5,5-Dimethyl-7-oxo-4,5,6,7-tetrahydro-1,3-benzothiazol-2-yl)morpholin-3-yl]methyl}biphenyl-3-yl)methanesulfonamide The title compound was prepared from Example 51 and {3-[(methylsulfonyl)-amino]phenyl}boronic acid according to Method V and was isolated in 99% purity after purification by preparative LC. LCMS (ES+) 526.0 (M+H)$^+$, RT 3.64 minutes.

Example 135

2-{(3S)-3-[3-(3,5-Dimethylisoxazol-4-yl)benzyl]morpholin-4-yl}-5,5-dimethyl-5,6-dihydro-1,3-benzothiazol-7(4H)-one The title compound was prepared from Example 51 and (3,5-dimethylisoxazol-4-yl)boronic acid according to Method V and was isolated in 93% purity after purification by preparative LC. LCMS (ES+) 452.0 (M+H)$^+$, RT 3.82 minutes.

Example 136

5,5-Dimethyl-2-[(3S)-3-{3-[1-(phenylsulfonyl)-1H-indol-3-yl]benzyl}morpholin-4-yl]-5,6-dihydro-1,3-benzothiazol-7(4H)-one The title compound was prepared from Example 51 and [1-(phenylsulfonyl)-1H-indol-3-yl]boronic acid according to Method V and was isolated in 94% purity after purification by preparative LC. LCMS (ES+) 612.0 (M+H)$^+$, RT 4.71 minutes.

Example 137

2-{(3S)-3-[3-(6-Chloropyridin-3-yl)benzyl]morpholin-4-yl}-5,5-dimethyl-5,6-dihydro-1,3-benzothiazol-7(4H)-one The title compound was prepared from Example 51 and (6-chloropyridin-3-yl)boronic acid according to Method V and was isolated in 94% purity after purification by preparative LC. LCMS (ES+) 468.0 (M+H)$^+$, RT 4.03 minutes.

Example 138

3'-{[(3S)-4-(5,5-Dimethyl-7-oxo-4,5,6,7-tetrahydro-1,3-benzothiazol-2-yl)morpholin-3-yl]methyl}biphenyl-4-carboxamide The title compound was prepared from Example 51 and (4-carbamoylphenyl)-boronic acid according to Method V and was isolated in 98% purity after purification by preparative LC. LCMS (ES+) 476.0 (M+H)$^+$, RT 3.14 minutes.

Example 139

5,5-dimethyl-2-{(3S)-3-[3-(3-fluoropyridin-4-yl)benzyl]morpholin-4-yl}-5,6-dihydro-1,3-benzothiazol-7(4H)-one The title compound was prepared from Example 51 and (3-fluoropyridin-4-yl)boronic acid according to Method V and was isolated in 90% purity after purification by preparative LC. LCMS (ES+) 452.0 (M+H)$^+$, RT 3.57 minutes.

Example 140

2-{(3S)-3-[3-(1-Benzyl-1H-pyrazol-4-yl)benzyl]morpholin-4-yl}-5,5-dimethyl-5,6-dihydro-1,3-benzothiazol-7(4H)-one The title compound was prepared from Example 51 and (1-benzyl-1H-pyrazol-4-yl)boronic acid according to Method V and was isolated in 92% purity after purification by preparative LC. LCMS (ES+) 513.0 (+H)$^+$, RT 4.02 minutes.

Example 141

5,5-Dimethyl-2-{(3S)-3-[3-(1-methyl-1H-pyrazol-4-yl)benzyl]morpholin-4-yl}-5,6-dihydro-1,3-benzothiazol-7(4H)-one The title compound was prepared from Example 51 and (1-methyl-1H-pyrazol-4-yl)boronic acid according to Method V and was isolated in 94% purity after purification by preparative LC. LCMS (ES+) 437.0 (+H)$^+$, RT 3.32 minutes.

Example 142

7,7-Dimethyl-2-(morpholin-4-yl)-4,6,7,8-tetrahydro-5H-[1,3]thiazolo[5,4-b]azepin-5-one To a stirred solution of Example 48 (1.00 g, 3.77 mmol) in formic acid (40 mL) was added, dropwise, hydroxylamine-O-sulfonic acid (0.64 g, 5.66 mmol). After refluxing overnight the reaction mixture was quenched with ice/water and neutralised with aqueous 5% NaOH and then extracted with DCM (2×40 μL). The organics were combined, dried (MgSO$_4$), filtered and concentrated in vacuo. Purification by column chromatography (SiO$_2$, 3:1 DCM/EtOAc) gave the title compound (0.24 g, 22%) as an off-white solid. δ$_H$ (DMSO-d$_6$) 10.77 (1H, s), 3.69 (4H, m), 3.42 (4H, m), 2.52 (2H, s), 2.25 (2H, s), 0.98 (6H, s). LCMS (ES+) 282.0 (M+H)$^+$.

Example 143

2-[(3S)-3-{[5-(Benzyloxy)-1H-indol-3-yl]methyl}morpholin-4-yl]-5,5-dimethyl-5,6-dihydro-1,3-benzothiazol-7(4H)-one The title compound was prepared from Intermediate 124 and Intermediate 15 according to Method H and was isolated as a white solid (52%) after purification by trituration (Et$_2$O). δ$_H$(CDCl$_3$) 7.98 (1H, br. s), 7.62-7.21 (7H, m), 7.14 (1H, d, J 2.2 Hz), 6.98 (1H, dd, J 8.8 and 2.4 Hz), 5.20 (2H, s), 4.35 (1H, s), 4.09 (1H, d, J 7.3 Hz), 3.92 (1H, d, J 11.8 Hz), 3.78-3.63 (3H, m), 3.55 (1H, dd, J 11.8 and 1.9 Hz), 3.41 (1H, dd, J 13.7 and 10.9 Hz), 3.06 (1H, dd, J 13.9 and 4.1 Hz), 2.75 (2H, s), 2.40 (2H, s), 1.09 (3H, s), 1.08 (3H, s). LCMS (ES+) 502.0 (M+H)$^+$.

Example 144

5,5-Dimethyl-2-[(3S)-3-{[5-(hydroxy)-1H-indol-3-yl]methyl}morpholin-4-yl]-5,6-dihydro-1,3-benzothiazol-7(4H)-one The title compound was prepared from Intermediate 125 and Intermediate 15 according to Method H and was isolated as a white solid (62%) after purification by trituration (Et$_2$O). δ$_H$(CDCl$_3$) 10.57 (1H, br. s), 8.58 (1H, s), 7.12-7.08 (2H, m), 7.03 (1H, d, J 2.0 Hz), 6.61 (1H, dd, J 8.6 and 2.2 Hz), 4.20-4.00 (1H, br. m), 3.98 (1H, d, J 7.2 Hz), 3.74-3.70 (2H, m), 3.64-3.48 (3H, m), 3.27-3.19 (1H, m), 2.84 (1H, dd, J 13.9 and 4.9 Hz), 2.69 (2H, s), 2.32 (2H, s), 1.05 (6H, s). LCMS (ES+) 412.0 (M+H)$^+$.

Example 145

7,7-Dimethyl-2-{(3S)-3-[(5-hydroxy-1H-indol-3-yl)methyl]morpholin-4-yl}-5,6,7,8-tetrahydro-4H-[1,3]thiazolo[5,4-c]azepin-4-one The title compound was prepared from Intermediate 125 and Intermediate 71 according to Method U and was isolated as a white solid (13%) after purification by preparative LC. δ$_H$ (CDCl$_3$) 10.52 (1H, br. s), 8.51 (1H, br. s), 7.63 (1H, t, J 4.9 Hz), 7.09 (1H, d, J 8.6 Hz), 7.03 (2H, s), 6.58 (1H, dd, J 8.6 and 2.3 Hz), 3.94-3.91 (2H, m), 3.66 (1H, d, J 11.4 Hz), 3.60-3.40 (4H, m), 3.26-3.12 (1H, m), 2.91 (1H, d, J 4.9 Hz), 2.78-2.76 (1H, m), 2.71 (2H, d, J 3.1 Hz), 0.96 (6H, s). LCMS (ES+) 427.0 (M+H)$^+$.

Example 146

3-{[(3S)-4-(5,5-Dimethyl-7-oxo-4,5,6,7-tetrahydro-1,3-benzothiazol-2-yl)morpholin-3-yl]methyl}-1H-indol-5-yl methanesulfonate To a stirred solution of Example 144 (0.11 g, 0.25 mmol) in THF (5 mL) was added, at 0° C., methanesulphonyl chloride (0.20 mL, 2.68 mmol). After stirring for 96 h at r.t., the reaction mixture was evaporated in vacuo and DCM (10 mL) and water (5 mL) were added. The aqueous layer was extracted with DCM (2×10 mL) and the combined organic layers were washed with water (3×10 mL), dried (MgSO$_4$), filtered and concentrated in vacuo. The resulting oil was purified by column chromatography (SiO$_2$, DCM, followed by 1:1 DCM/EtOAc, followed by EtOAc) to give the title compound (0.06 g, 47%) as a pale yellow solid. δ$_H$ (DMSO-d$_6$) 11.12 (1H, s), 7.83 (1H, s), 7.39 (1H, d, J 8.7 Hz), 7.33 (1H, d, J 2.2 Hz), 7.07 (1H, dd, J 8.8 and 2.3 Hz), 4.40-4.20 (1H, m), 3.98 (1H, d, J 9.6 Hz), 3.75 (1H, d, J 11.7 Hz), 3.59-3.49 (4H, m), 3.33 (3H, s), 3.31-3.09 (1H, m), 2.95 (1H, dd, J 13.7 and 4.7 Hz), 2.69 (2H, s), 2.30 (2H, s), 1.04 (3H, s), 1.03 (3H, s). LCMS (ES+) 490.3 (M+H)$^+$.

Example 147

Method Z

2-[3-(3,4-Dihydroisoquinolin-2(1H)-ylcarbonyl)morpholin-4-yl]-5,5-dimethyl-5,6-dihydro-1,3-benzothiazol-7(4H)-one To a stirred solution of 1,2,3,4-tetrahydroisoquinoline (0.08 mL, 0.64 mmol) in DMF (2 mL) was added Intermediate 64 (0.20 g, 0.64 mmol), HBTU (0.25 g, 0.64 mmol) and DIPEA (0.33 mL, 1.92 mmol) dropwise. The reaction mixture was stirred for 2 h at ambient temperature and then concentrated in vacuo. Purification by column chromatography (SiO$_2$, 0-10% MeOH in DCM) followed by trituration with MeOH/Et$_2$O gave the title compound (0.19 g, 69%) as a pink solid. δ$_H$ (DMSO-d$_6$, 130° C.) 7.20 (4H, br. s), 5.18-5.15 (1H, m), 4.78 (1H, d, J 6.5 Hz), 4.61 (1H, d, J 6.5 Hz), 4.10 (1H, d, J 12.0 Hz), 4.02-3.91 (3H, m), 3.80-3.76 (2H, m), 3.72-3.64 (1H, m), 3.60-2.54 (1H, m), 3.00-2.79 (4H, m), 2.30 (2H, s), 1.05 (3H, s), 1.02 (3H, s). LCMS (ES+) 426.0 (M+H)$^+$.

Example 148

2-[3-(3,4-Dihydroquinoxalin-1(2H)-ylcarbonyl)morpholin-4-yl]-5,5-dimethyl-5,6-dihydro-1,3-benzothiazol-7(4H)-one The title compound was prepared from Intermediate 64 and 1,2,3,4-tetrahydroquinoxaline according to Method Z and was isolated as an off-white solid (45%) after purification by preparative LC. δ$_H$ (DMSO-d$_6$) 7.30-7.23 (1H, br. m), 6.99-6.88 (1H, br. m), 6.69-6.62 (1H, br. m), 6.56-6.46 (1H, br. m), 6.34-6.22 (1H, br. m), 5.48-5.35 (1H, br. m), 4.20-4.11 (1H, br. m), 4.04-3.95 (1H, br. m), 3.90-3.36 (6H, br. m), 3.28-3.08 (2H, br. m), 2.76-2.62 (2H, br. m), 2.39-2.26 (2H, br. m), 1.08-1.00 (6H, br. m). LCMS (ES+) 426.5 (M+H)$^+$.

Example 149

5,5-Dimethyl-2-{3-[(6-methyl-3,4-dihydroquinolin-1(2H)-yl)carbonyl]morpholin-4-yl}-5,6-dihydro-1,3-benzothiazol-7(4H)-one The title compound was prepared from Intermediate 64 and 6-methyltetrahydro-quinoline according to Method O and was isolated as an off-white solid (7%) after purification by column chromatography (SiO$_2$, from 100% heptane to 60% EtOAc). δ$_H$(DMSO-d$_6$) 7.42 (1H, d, J 8.0 Hz), 7.10-7.00 (2H, m), 5.40 (1H, br. s), 4.10-3.95 (2H, m), 3.90-3.40 (6H, m), 2.80-2.60 (4H, m), 2.35 (2H, m), 2.25 (3H, s), 2.00-1.75 (2H, m), 1.05 (3H, s), 1.04 (3H, s). LCMS (ES+) 440.0 (M+H)$^+$.

Example 150

5-Dimethyl-2-{3-[(6-methoxy-3,4-dihydroquinolin-1 (2H)-yl carbonyl]moroholin-4-yl}-5,6-dihydro-1,3-benzothiazol-7(4H)-one The title compound was prepared from Intermediate 64 and 6-methoxytetrahydro-quinoline according to Method O and was isolated as a white solid (3%) after purification by column chromatography (SiO$_2$, from 100% heptane to 100% EtOAc). $\delta_H$ (CDCl$_3$) 7.55 (1H, d, J 9.5 Hz), 6.82-6.75 (2H, m), 5.50 (1H, br. s), 4.35-4.22 (1H, m), 4.20-4.00 (2H, m), 3.80 (3H, s), 3.70-3.20 (5H, m), 2.80-2.60 (4H, m), 2.45-2.33 (2H, m), 2.20-2.10 (1H, m), 1.85-1.70 (1H, m), 1.15 (3H, s), 1.14 (3H, s). LCMS (ES+) 456.0 (+H)$^+$.

Example 151

Method AB

5-Dimethyl-2-[(3S)-3-(3-phenylprop-2-yn-1-yl)morpholin-4-yl]-5,6-dihydro-1,3-benzothiazol-7(4H)-one To a stirred solution of Intermediate 127 (0.05 g, 0.25 mmol) in IPA (2 mL) was added Intermediate 15 (0.07 g, 0.28 mmol) and DIPEA (0.05 mL, 0.31 mmol). The reaction mixture was then heated under microwave irradiation in a sealed tube to 160° C. for 1.5 h. After cooling to r.t. the solvent was removed in vacuo and the crude material was purified by column chromatography (SiO$_2$, 1.5:1 EtOAc/hexanes) to give the title compound (0.02 g, 20%) as a yellow oil. $\delta_H$ (DMSO-d$_6$) 7.32-7.22 (5H, m), 4.33 (1H, m), 3.96-3.92 (2H, m), 3.71-3.66 (2H, m), 3.60-3.48 (2H, m), 2.95 (2H, d, J 7.7 Hz), 2.63 (2H, s), 2.29-2.27 (2H, m), 1.01 (6H, s). LCMS (ES+) 381.0 (M+H)$^+$.

Example 152

2-[(3S)-3-(1H-Benzotriazol-1-ylmethyl)morpholin-4-yl]-5,5-dimethyl-5,6-dihydro-1,3-benzothiazol-7(4H)-one The title compound was prepared from Intermediate 128 and Intermediate 15 according to Method AB and was isolated as a pale yellow solid (47%) after purification by column chromatography (SiO$_2$, 1:1 EtOAc/hexanes). $\delta_H$ (DMSO-d$_6$) 7.95 (2H, dd, J 17.6 and 8.4 Hz), 7.57 (1H, m), 7.36 (1H, m), 5.15 (2H, m), 4.77 (1H, m), 4.06-3.84 (3H, m), 3.83-3.57 (3H, m), 2.33-1.91 (4H, m), 0.92 (3H, s), 0.87 (3H, s). LCMS (ES+) 398.3 (M+H)$^+$.

Example 153

2-[(3S)-3-(1H-Benzimidazol-1-ylmethyl morpholin-4-yl]-5,5-dimethyl-5,6-dihydro-1,3-benzothiazol-7 (4H)-one The title compound was prepared from Intermediate 129 and Intermediate 15 according to Method AB and was isolated as a white solid (13%) after purification by column chromatography (SiO$_2$, 1:1 EtOAc/hexanes). $\delta_H$ (DMSO-d$_6$) 8.11 (1H, s), 7.76 (1H, d, J 7.9 Hz), 7.54 (1H, d, J 7.9 Hz), 7.27 (1H, m), 7.17 (1H, m), 4.65 (3H, m), 4.03-3.83 (3H, m), 3.70-3.55 (3H, m), 2.36 (1H, d, J 17.0 Hz), 2.15 (3H, m), 0.94 (3H, s), 0.91 (3H, s). LCMS (ES+) 397.3 (M+H)$^+$.

Example 154

2-[2-(Aminomethyl)morpholin-4-yl]-5,5-dimethyl-5, 6-dihydro-1,3-benzothiazol-7(4H)-one To a stirred solution of Intermediate 131 (0.46 g, 1.07 mmol) in EtOH (20 mL) was added hydrazine hydrate (1.00 mL, 19.00 mmol) and the reaction mixture was heated to 80° C. for 2 h. After cooling, the reaction mixture was concentrated in vacuo and purification by preparative HPLC gave the title compound (0.30 g, 94%) as a white solid. $\delta_H$ (CDCl$_3$) 4.10-3.90 (2H, m), 3.80-3.60 (5H, m), 3.30 (1H, m), 3.00 (1H, m), 2.85 (2H, m), 2.70 (2H, s), 2.40 (2H, s), 1.10 (6H, s). LCMS (ES+) 296.0 (M+H)$^+$.

Example 155

Method AD

N-(1-Benzothien-3-ylmethyl)-2-[4-(5,5-dimethyl-7-oxo-4,5,6,7-tetrahydro-1,3-benzothiazol-2-yl)morpholin-2-yl]acetamide To a stirred solution of 1-(1-benzothien-3-yl)methanamine (0.03 g, 0.15 mmol) and Intermediate 130 (0.18 g, 0.15 mmol) in DMF (2 mL) was added HBTU (0.07 g, 0.18 mmol) and the reaction mixture was stirred at room temperature for 4 h. The solvent was then removed in vacuo and purification by preparative HPLC gave the title compound (0.05 g, 57%) as a white solid. $\delta_H$ (CDCl$_3$) 7.90 (1H, m), 7.80 (1H, m), 7.40 (3H, m), 6.30 (1H, m), 4.70 (2H, d, J 5.6 Hz), 4.00 (3H, m), 3.70 (2H, m), 3.18 (1H, dt, J 12.6 and 4.0 Hz), 2.99 (1H, dd, J 11.0 and 2.2 Hz), 2.70 (2H, s), 2.46 (2H, m), 2.40 (2H, s) 1.10 (6H, s). LCMS (ES+) 470.0 (M+H)$^+$.

Example 156

N-{[4-(5,5-Dimethyl-7-oxo-4,5,6,7-tetrahydro-1,3-benzothiazol-2-yl)morpholin-2-yl]methyl}-1-benzofuran-2-carboxamide The title compound was prepared from 2-benzofuran carboxylic acid and Example 154 according to Method AD and was isolated as a white solid (39%) after purification by preparative HPLC. $\delta_H$ (CDCl$_3$) 7.68 (1H, d, J 7.8 Hz), 7.60-7.40 (3H, m), 7.30 (1H, t, J 7.8 Hz), 7.00 (1H, m), 4.10 (2H, m), 3.90-3.70 (3H, m), 3.50 (1H, m), 3.35 (1H, m), 3.30 (1H, m), 3.10 (1H, m), 2.70 (2H, s), 2.40 (2H, s), 1.10 (6H, s). LCMS (ES+) 440.0 (M+H)$^+$.

Example 157

N-{[4-(5,5-Dimethyl-7-oxo-4,5,6,7-tetrahydro-1,3-benzothiazol-2-yl)morpholin-2-yl] methyl}benzenesulfonamide To a stirred solution of Example 154 (0.10 g, 0.34 mmol) and pyridine (0.04 g, 0.51 mmol) in DCM (10 mL) was added benzenesulphonyl chloride (0.06 g, 0.34 mmol) and the reaction mixture was stirred at room temperature for 4 h. The solvent was then removed in vacuo and purification by preparative HPLC gave the title compound (0.03 g, 20%) as a white solid. $\delta_H$ (CDCl$_3$) 7.90 (2H, dd, J 6.9 and 1.5 Hz), 7.60

(3H, m), 4.87 (1H, t, J 6.0 Hz), 4.00 (2H, m), 3.75 (1H, m), 3.60 (2H, m), 3.20 (2H, m), 3.00 (2H, m), 2.70 (2H, s), 2.40 (2H, s), 1.10 (6H, s). LCMS (ES+) 436.0 (M+H)+.

Example 158

(7E)-5,5-Dimethyl-2-(morpholin-4-yl)-5,6-dihydro-1,3-benzothiazol-7(4H)-one hydrazone To a stirred solution of Example 48 (0.27 g, 1.00 mmol) in EtOH (10 mL) was added hydrazine monohydrate (0.05 g, 0.05 mL, 1.00 mmol) and a catalytic amount of AcOH. The reaction mixture was then heated to reflux for 8 h. Upon cooling, the reaction mixture was poured into aqueous sat. NaHCO₃ (50 mL) and extracted with DCM (2×50 mL). The combined organic fractions were dried over MgSO₄, filtered and concentrated in vacuo to give the title compound as a white solid (0.10 g, 35%). δ$_H$ (DMSO-d₆) 5.93 (2H, br. s), 3.68 (4H, t, J 4.9 Hz), 3.36 (4H, t, J 4.9 Hz), 2.42 (2H, s), 2.22 (2H, s), 1.00 (6H, s). LCMS (ES+) 281.2 (M+H)+.

The invention claimed is:

1. A pharmaceutical composition comprising a compound of formula (I), or a pharmaceutically acceptable salt thereof:

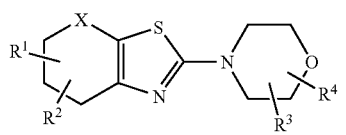
(I)

wherein
—X— represents a group of formula (a), (b), (c), (d), (e), (f), (g) or (h):

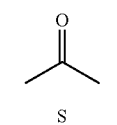
(a)

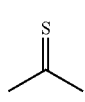
(b)

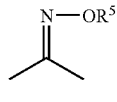
(c)

(d)

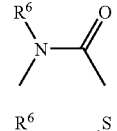
(e)

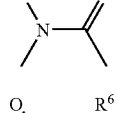
(f)

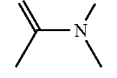
(g)

-continued

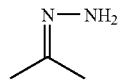
(h)

$R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzofused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzofused and/or substituted by one or more substituents; and $R^5$ and $R^6$ independently represent hydrogen or $C_{1-6}$ alkyl, together with a pharmaceutically acceptable carrier.

2. A compound of formula (I) or a pharmaceutically acceptable salt thereof:

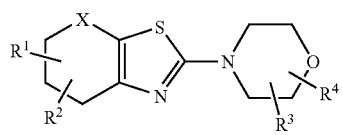
(I)

wherein,
—X— represents a group of formula (a), (b), (c), (d), (e), (f), (g) or (h):

(a)

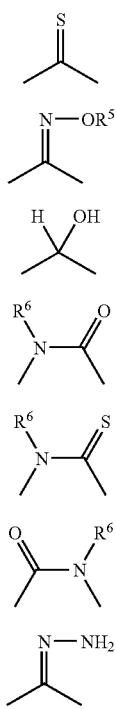

(b)

(c)

(d)

(e)

(f)

(g)

(h)

$R^1$ and $R^2$ independently represent hydrogen; or $C_{1-6}$ alkyl, $C_{3-7}$ cycloalkyl, $C_{3-7}$ cycloalkyl($C_{1-4}$alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$) alkyl, any of which groups may be optionally, substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzofused and/or substituted by one or more substituents;

$R^3$ and $R^4$ independently represent hydrogen; or $C_{1-6}$ alkyl, $C_{3-7}$ cycloalkyl, $C_{1-7}$ cycloalkyl($C_{1-6}$)alkyl, aryl, aryl ($C_{1-6}$)alkyl, aryl($C_{2-6}$)alkenyl, aryl($C_{2-6}$)alkynyl, biaryl ($C_{1-6}$)alkyl, $C_{3-7}$ heterocycloalkyl, $C_{3-7}$ heterocycloalkyl($C_{1-6}$)allyl, $C_{3-7}$ heterocycloalkylcarbonyl, heteroaryl, heteroaryl($C_{1-6}$)alkyl, heteroaryl-aryl($C_{1-6}$) alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$, and $R^4$, when attached to adjacent carbon atoms, represent, when taken together with the carbon atoms to which they are attached, $C_{5-7}$ cycloalkyl, phenyl or heteroaryl, any of which groups may be optionally benzofused and/or substituted by one or more substituents; and $R^5$ and $R^6$ independently represent hydrogen or $C_{1-6}$ alkyl; provided the compound is not:

2-(morpholin-4-yl)-5,6-dihydro-1,3-benzothiazol-7(4H)-one;

5,5-dimethyl-2-(morpholin-4-yl)-5,6-dihydro-1,3-benzothiazol-7(4H)-one;

2-(morpholin-4-yl)-5,6,7,8-tetrahydro-4H-[1,3]thiazolo[5,4-c]azepin-4-one; and 7,7-dimethyl-2-(morpholin-4-yl)-5,6,7,8-tetrahydro-4H-[1,3]thiazolo[5,4-c]azepin-4-one.

3. A compound of formula (IIA), or a pharmaceutically acceptable salt thereof:

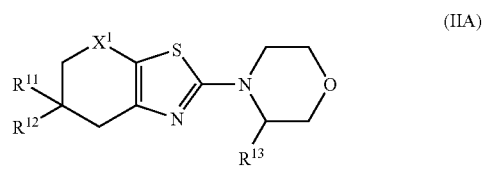

(IIA)

wherein

—$X^1$— represents a group of formula (a) or (e):

(a)

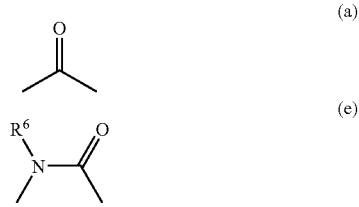

(e)

$R^6$ represents hydrogen or $C_{1-6}$ alkyl;

$R^{11}$ represents hydrogen or optionally substituted $C_{2-6}$ alkyl; and $R^{12}$ represents $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl ($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$) alkyl, heteroaryl-aryl($C_{1-6}$)alkyl or aryl-heteroaryl ($C_{1-6}$)alkyl, any of which groups may be optionally substituted by one or more substituents.

4. The compound of formula (IIB), or a pharmaceutically acceptable salt thereof:

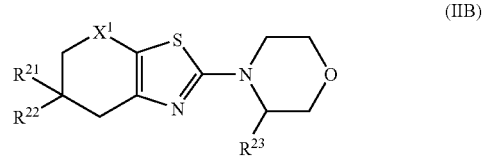

(IIB)

wherein

—X¹— represents a group of formula (a) or (e):

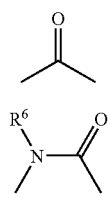

R⁶ represents hydrogen or C₁₋₆ alkyl;
R²¹ represents hydrogen or optionally substituted C₁₋₆ alkyl; and
R²² represents hydrogen; or C₁₋₆ alkyl, C₃₋₇ cycloalkyl, C₃₋₇ cycloalkyl(C₁₋₆)alkyl, aryl, aryl(C₁₋₆)alkyl, C₃₋₇ heterocycloalkyl, C₃₋₇ heterocycloalkyl(C₁₋₆)alkyl, heteroaryl or heteroaryl(C₁₋₆)alkyl, any of which groups may be optionally substituted by one or more substituents; or
R²¹ and R²², when taken together with the carbon atom to which they are both attached, represent C₃₋₇ cycloalkyl or C₃₋₇ heterocycloalkyl, either of which groups may be optionally substituted by one or more substituents; and
R²³ represents C₁₋₆ alkyl, C₃₋₇ cycloalkyl, C₃₋₇ cycloalkyl(C₁₋₆)alkyl, aryl, aryl(C₁₋₆)alkyl, aryl(C₂₋₆)alkenyl, aryl(C₂₋₆)alkynyl, biaryl(C₁₋₆)alkyl, C₃₋₇ heterocycloalkyl, C₃₋₇ heterocycloalkyl(C₁₋₆)alkyl, C₃₋₇ heterocycloalkylcarbonyl, heteroaryl, heteroaryl(C₁₋₆)alkyl, heteroaryl-aryl(C₁₋₆)alkyl or aryl-heteroaryl(C₁₋₆)alkyl, any of which groups may be optionally substituted by one or more substituents.

5. The compound as claimed in claim 4 wherein R²³ represents C₁₋₆ alkyl, aryl(C₁₋₆)alkyl, biaryl-(C₁₋₆)alkyl, heteroaryl(C₁₋₆)alkyl or heteroaryl-aryl(C₁₋₆)alkyl, any of which groups may be optionally substituted by one or more substituents.

6. The compound as claimed in claim 5 wherein R²³ represents substituted or unsubstituted indolylmethyl.

7. A compound of formula (IIC), or a pharmaceutically acceptable salt thereof:

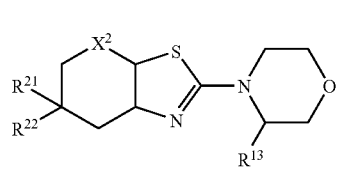

wherein
—X²— represents a group of formula (b), (c), (d), (f), (g) or (h):

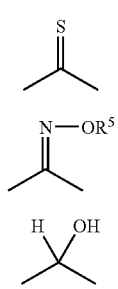

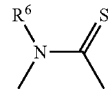
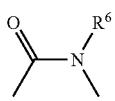
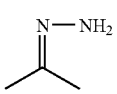

R⁵ and R⁶ independently represent hydrogen or C₁₋₆ alkyl;
R¹³ represents hydrogen; or C₁₋₆ alkyl, C₃₋₇ cycloalkyl, C₃₋₇ cycloalkyl(C₁₋₆)alkyl, aryl, aryl(C₁₋₆)alkyl, aryl(C₂₋₆)alkenyl, aryl(C₂₋₆)alkynyl, biaryl(C₁₋₆)alkyl, C₃₋₇ heterocycloalkyl, C₃₋₇ heterocycloalkyl(C₁₋₆)alkyl, C₃₋₇ heterocycloalkylcarbonyl, heteroaryl, heteroaryl(C₁₋₆)alkyl, heteroaryl-aryl(C₁₋₆)alkyl or aryl-heteroaryl(C₁₋₆)alkyl, any of which groups may be optionally substituted by one or more substituents;
R²¹ represents hydrogen or optionally substituted C₁₋₆ alkyl; and
R²² represents hydrogen; or C₁₋₆ alkyl, C₃₋₇ cycloalkyl, C₃₋₇ cycloalkyl(C₁₋₆)alkyl, aryl, aryl(C₁₋₄)alkyl, C₃₋₇ heterocycloalkyl, C₃₋₇ heterocycloalkyl(C₁₋₆)alkyl, heteroaryl or heteroaryl(C₁₋₆)alkyl, any of which groups may be optionally substituted by one or more substituents; or
R²¹ and R²², when taken together with the carbon atom to which they are both attached, represent C₃₋₇ cycloalkyl or C₃₋₇ heterocycloalkyl, either of which groups may be optionally substituted by one or more substituents.

8. The compound as claimed in claim 4, or a pharmaceutically acceptable salt thereof,
wherein
R²³ represents

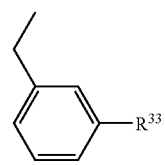

and R³³ represents aryl or heteroaryl, either of which groups may be optionally substituted by one or more substituents.

9. The compound as claimed in claim 4, or a pharmaceutically acceptable salt thereof:
wherein
R²³ represents

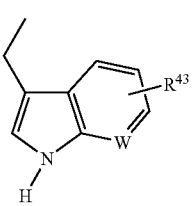

W represents CH or N; and

R$^{43}$ represents hydrogen, halogen, cyano, C$_{1-6}$ alkyl, hydroxy(C$_{1-6}$)alkyl, trifluoromethyl, aryl(C$_{1-6}$)alkyl, hydroxy, C$_{1-6}$ alkoxy, trifluoromethoxy, aryloxy, aryl (C$_{1-6}$)alkoxy, C$_{1-6}$ alkylthio, arylsulphonyl, C$_{1-6}$ alkylsulphonyloxy, amino, C$_{2-6}$ alkylcarbonylamino, C$_{1-6}$ alkylsulphonylamino, C$_{2-6}$ alkylcarbonyl or aminocarbonyl.

10. The compound as claimed in claim 9 wherein W represents CH.

11. The compound as claimed in claim 9 wherein R$^{43}$ represents hydrogen.

12. The compound as claimed in claim 2 that is 2-(Morpholin-4-yl)-4H-spiro[1,3-benzothiazole-5,1'-cyclopentan]-7(6H)-one;

5-Isopropyl-2-(morpholin-4-yl)-5,6-dihydro-1,3-benzothiazol-7(4H)-one;

5-(4-Chlorophenyl)-2-(morpholin-4-yl)-5,6-dihydro-1,3-benzothiazol-7(4H)-one;

2-(Morpholin-4-yl)-5-phenyl-5,6-dihydro-1,3-benzothiazol-7(4H)-one;

2-(Morpholin-4-yl)-4H-spiro[1,3-benzothiazole-5,1'-cyclohexan]-7(6H)-one;

5-(4-Methoxyphenyl)-2-(morpholin-4-yl)-5,6-dihydro-1,3-benzothiazol-7(4H)-one;

2-(Morpholin-4-yl)-5-propyl-5,6-dihydro-1,3-benzothiazol-7(4H)-one;

5-Methyl-2-(morpholin-4-yl)-5,6-dihydro-1,3-benzothiazol-7(4H)-one;

6,6-Dimethyl-2-(morpholin-4-yl)-5,6-dihydro-1,3-benzothiazol-7(4H)-one;

5-[4-(Methylthio)phenyl]-2-(morpholin-4-yl)-5,6-dihydro-1,3-benzothiazol-7-(4H)-one;

5-(2-Furyl)-2-(morpholin-4-yl)-5,6-dihydro-1,3-benzothiazol-7(4H)-one;

6-Methyl-2-(morpholin-4-yl)-5,6-dihydro-1,3-benzothiazol-7(4H)-one;

2-[(3R)-3-(1H-Indol-3-ylmethyl)morpholin-4-yl]-5,5-dimethyl-5,6-dihydro-1,3-benzothiazol-7(4H)-one;

5,5-Dimethyl-2-[3-(2-naphthylmethyl)morpholin-4-yl]-5,6-dihydro-1,3-benzothiazol-7(4H)-one;

5,5-Dimethyl-2-[3-(1-naphthylmethyl)morpholin-4-yl]-5,6-dihydro-1,3-benzothiazol-7(4H)-one;

5,5-Dimethyl-2,3-(2-phenethyl-morpholin-4-yl)-5,6-dihydro-1,3-benzothiazol-7(4H)-one;

2-[(3S)-3-Benzylmorpholin-4-yl]-5,5-dimethyl-5,6-dihydro-1,3-benzothiazol-7(4H)-one;

5,5-Dimethyl-2-[(4aS,9aR)-2,3,9,9a-tetrahydroindeno[2,1-b][1,4]oxazin-4(4aH)-yl]-5,6-dihydro-1,3-benzothiazol-7(4H)-one;

2-[3-(4-Chlorobenzyl)morpholin-4-yl]-5,5-dimethyl-5,6-dihydro-1,3-benzothiazol-7(4H)-one;

5,5-Dimethyl-2-[3-(5-methyl-1H-indol-3-ylmethyl)morpholin-4-yl]-5,6-dihydro-1,3-benzothiazol-7(4H)-one;

5,5-Dimethyl-2-{3-[4-(morpholin-4-yl)benzyl]morpholin-4-yl}-5,6-dihydro-1,3-benzothiazol-7(4H)-one;

2-(2,3-Dihydro-4H-1,4-benzoxazin-4-yl)-5,5-dimethyl-5,6-dihydro-1,3-benzothiazol-7(4H)-one;

5,5-Dimethyl-2-[3-(1H-indol-3-ylmethyl)morpholin-4-yl]-5,6-dihydro-1,3-benzothiazol-7(4H)-one;

5,5-Dimethyl-2-[(3S)-3-(1H-indol-3-ylmethyl)morpholin-4-yl]-5,6-dihydro-1,3-benzothiazol-7(4H)-one;

5,5-Dimethyl-2-{3-[(1-methyl-1H-indol-3-yl)methyl]morpholin-4-yl}-5,6-dihydro-1,3-benzothiazol-7(4H)-one;

2-{(3S)-3-[(1-Acetyl-1H-indol-3-yl)methyl]morpholin-4-yl}-5,5-dimethyl-5,6-dihydro-1,3-benzothiazol-7(4H)-one;

5,5-Dimethyl-2-(2-phenylmorpholin-4-yl)-5,6-dihydro-1,3-benzothiazol-7(4H)-one;

2-[3-(4-Bromobenzyl)morpholin-4-yl]-5,5-dimethyl-5,6-dihydro-1,3-benzothiazol-7(4H)-one;

2-[3-(2,3-Dihydro-1H-indol-1-ylmethyl)morpholin-4-yl]-5,5-dimethyl-5,6-dihydro-1,3-benzothiazol-7(4H)-one;

5,5-Dimethyl-2-[3-(1H-indol-1-ylmethyl)morpholin-4-yl]-5,6-dihydro-1,3-benzothiazol-7(4H)-one;

5,5-Dimethyl-2-(trans-2,6-dimethylmorpholin-4-yl)-5,6-dihydro-1,3-benzothiazol-7(4H)-one;

2-[3-(Anilinomethyl)morpholin-4-yl]-5,5-dimethyl-5,6-dihydro-1,3-benzothiazol-7(4H)-one;

5,5-Dimethyl-2-{3-[(N-methyl-N-phenylamino)methyl]morpholin-4-yl}-5,6-dihydro-1,3-benzothiazol-7(4H)-one;

2-[3-(3,4-Dihydroquinolin-1(2H)-ylmethyl)morpholin-4-yl]-5,5-dimethyl-5,6-dihydro-1,3-benzothiazol-7(4H)-one;

2-[3-(3,4-Dihydroisoquinolin-2(1H)-ylmethyl)morpholin-4-yl]-5,5-dimethyl-5,6-dihydro-1,3-benzothiazol-7(4H)-one;

(7E,Z)-5,5-Dimethyl-2-(morpholin-4-yl)-5,6-dihydro-1,3-benzothiazol-7(4H)-one oxime;

7Z)-5,5-Dimethyl-2-(morpholin-4-O-5,6-dihydro-1,3-benzothiazol-7(4H)-one oxime;

(7E,Z)-2-(Morpholin-4-yl)-5,6-dihydro-1,3-benzothiazol-7(4H)-one oxime;

(7E,Z)-5,5-Dimethyl-2-[(3S)-3-(1H-indol-3-ylmethyl)morpholin-4-yl]-5,6-dihydro-1,3-benzothiazol-7(4H)-one oxime;

(7E,Z)-6-Methyl-2-(morpholin-4-yl)-5,6-dihydro-1,3-benzothiazol-7(4H)-one oxime;

(7E,Z)-6,6-Dimethyl-2-(morpholin-4-yl)-5,6-dihydro-1,3-benzothiazol-7(4H)-one oxime;

7,7-Dimethyl-2-[(3S)-3-(1H-indol-3-ylmethyl)morpholin-4-yl]-5,6,7,8-tetrahydro-4H-[1,3]thiazolo[5,4-c]azepin-4-one;

6-Methyl-2-(morpholin-4-yl)-5,6,7,8-tetrahydro-4H-[1,3]thiazolo[5,4-c]azepin-4-one;

6,6-Dimethyl-2-(morpholin-4-yl)-5,6,7,8-tetrahydro-4H-[1,3]thiazolo[5,4-c]azepin-4-one;

5,5-Dimethyl-2-(morpholin-4-yl)-4,5,6,7-tetrahydro-1,3-benzothiazol-7-ol;

5,5-Dimethyl-2-(morpholin-4-yl)-5,6-dihydro-1,3-benzothiazole-7(4H)-thione;

2-[(3S)-3-(3-Bromobenzyl)morpholin-4-yl]-5,5-dimethyl-5,6-dihydro-1,3-benzothiazol-7(4H)-one;

2-[(3S)-3-(Biphenyl-3-ylmethyl)morpholin-4-yl]-5,5-dimethyl-5,6-dihydro-1,3-benzothiazol-7(4H)-one:

5,5-Dimethyl-2-[(3S)-3-(3-(pyridin-3-yl)benzyl)morpholin-4-yl]-5,6-dihydro-1,3-benzothiazol-7(4H)-one;

5,5-Dimethyl-2-[(3S)-3-(3-thienyl)benzyl morpholin-4-yl]-5,6-dihydro-1,3-benzothiazol-7(4H)-one;

5,5-Dimethyl-2-[(3S)-3-(3-(pyridin-4-yl)benzyl)morpholin-4-yl]-5,6-dihydro-1,3-benzothiazol-7(4H)-one;

5,5-Dimethyl-2-[(3S)-3-(3-(pyrimidin-5-yl)benzyl)morpholin-4-yl]-5,6-dihydro-1,3-benzothiazol-7(4H)-one;

2-[(3S)-3-(3-Bromobenzyl)morpholin-4-yl]-7,7-dimethyl-5,6,7,8-tetrahydro-4H-[1,3]thiazolo[5,4-c]azepin-4-one;

2-[(3S)-3-(Biphenyl-3-ylmethyl)morpholin-4-yl]-7,7-dimethyl-5,6,7,8-tetrahydro-4H-[1,3]thiazolo[5,4-c]azepin-4-one;

7,7-Dimethyl-2-[(3S)-3-(3-(pyridin-3-yl)benzyl)morpholin-4-yl]-5,6,7,8-tetrahydro-4H-[1,3]thiazolo[5,4-c]azepin-4-one;
5,5-Dimethyl-2-[3-(1H-pyrrolo[2,3-b]pyridin-3-ylmethyl)morpholin-4-yl]-5,6-dihydro-1,3-benzothiazol-7(4H)-one;
7,7-Dimethyl-2-[(3R)-3-(1H-indol-3-ylmethyl)morpholin-4-yl]-5,6,7,8-tetrahydro-4H-[1,3]thiazolo[5,4-c]azepin-4-one;
7,7-Dimethyl-2-[3-(1H-pyrrolo[2,3-b]pyridin-3-ylmethyl)morpholin-4-yl]-5,6,7,8-tetrahydro-4H-[1,3]thiazolo[5,4-c]azepin-4-one;
5,5-Dimethyl-2-{(3R)-3-[(phenylthio)methyl]morpholin-4-yl}-5,6-dihydro-1,3-benzothiazol-7(4H)-one;
5,5-Dimethyl-2-[3-(phenoxymethyl)morpholin-4-yl]-5,6-dihydro-1,3-benzothiazol-7(4H)-one;
7,7-Dimethyl-2-(morpholin-4-yl)-5,6,7,8-tetrahydro-4H-[1,3]thiazolo[5,4-c]azepine-4-thione;
7,7-Dimethyl-2-[(3S)-3-(1H-indol-3-ylmethyl)morpholin-4-yl]-5,6,7,8-tetrahydro-4H-[1,3]thiazolo[5,4-c]azepine-4-thione;
5,5-Dimethyl-2-[3-[(pyridin-3-ylamino)methyl]morpholin-4-yl]-5,6-dihydro-1,3-benzothiazol-7(4H)-one;
5,5-Dimethyl-2-[3-(piperidin-1-ylcarbonyl)morpholin-4-yl]-5,6-dihydro-1,3-benzothiazol-7(4H)-one;
2-[3-(3,4-Dihydroquinolin-1(2H)-ylcarbonyl)morpholin-4-yl]-5,5-dimethyl-5,6-dihydro-1,3-benzothiazol-7(4H)-one;
2-[3-(1-Benzothien-3-ylmethyl)morpholin-4-yl]-5,5-dimethyl-5,6-dihydro-1,3-benzothiazol-7(4H)-one;
2-[3-(Biphenyl-4-ylmethyl)morpholin-4-yl]-5,5-dimethyl-5,6-dihydro-1,3-benzothiazol-7(4H)-one;
5,5-Dimethyl-2-[3-(4-(pyridin-3-yl)benzyl)morpholin-4-yl]-5,6-dihydro-1,3-benzothiazol-7(4H)-one;
5,5-Dimethyl-2-[3-(5-methyl-1H-indol-3-yl)methyl)morpholin-4-yl]-5,6-dihydro-1,3-benzothiazole-7(4H)-thione;
5,5-Dimethyl-2-[3-(1-naphthylmethyl)morpholin-4-yl]-5,6-dihydro-1,3-benzothiazole-7(4H)-thione;
2-[3-(1-Benzothien-3-ylmethyl)morpholin-4-yl]-5,5-dimethyl-5,6-dihydro-1,3-benzothiazole-7(4H)-thione;
N-{[4-(5,5-Dimethyl-7-oxo-4,5,6,7-tetrahydro-1,3-benzothiazol-2-yl)morpholin-3-yl]methyl}benzenesulfonamide;
2-[3-(1-Benzothien-2-ylmethyl)morpholin-4-yl]-5,6-dihydro-1,3-benzothiazol-7(4H)-one;
7,7-Dimethyl-2-[3-(isoquinolin-4-ylmethyl)morpholin-4-yl]-5,6,7,8-tetrahydro-4H-[1,3]thiazolo[5,4-c]azepin-4-one;
7,7-Dimethyl-2-[3-(quinolin-5-ylmethyl)morpholin-4-yl]-5,6,7,8-tetrahydro-4H-[1,3]thiazolo[5,4-c]azepin-4-one;
7,7-Dimethyl-2-[3-(quinolin-8-ylmethyl)morpholin-4-yl]-5,6,7,8-tetrahydro-4H-[1,3]thiazolo[5,4-c]azepin-4-one;
5,5-Dimethyl-2-[3-(quinolin-8-ylmethyl)morpholin-4-yl]-5,6-dihydro-1,3-benzothiazol-7(4H)-one;
5,5-Dimethyl-2-[(3S)-3-(3-(pyrroldin-1-yl)benzyl)morpholin-4-yl]-5,6-dihydro-1,3-benzothiazol-7(4H)-one;
2-{3-[(6-Bromopyridin-2-yl)methyl]morpholin-4-yl}-5,5-dimethyl-5,6-dihydro-1,3-benzothiazol-7(4H)-one:
5,5-Dimethyl-2-{3-[(6-phenylpyridin-2-yl)methyl]morpholin-4-yl}-5,6-dihydro-1,3-benzothiazol-7(4H)-one:
5,5-Dimethyl-2-{(3S)-3-[2(2'-methylbiphenyl-3-yl)methyl]morpholin-4-yl}-5,6-dihydro-1,3-benzothiazol-7(4H)-one;
5,5-Dimethyl-2-{(3S)-3-[3'-methoxybiphenyl-3-yl)methyl]morpholin-4-yl}-5,6-dihydro-1,3-benzothiazol-7(4H)-one;
5,5-Dimethyl-2-{(3S)-3-[2'-(trifluoromethyl)biphenyl-3-yl]methyl morpholin-4-yl}-5,6-dihydro-1,3-benzothiazol-7(4H)-one;
2{(3S)-3-[(2'-Chlorobiphenyl-3-yl)methyl]morpholin-4-yl}-5,5-dimethyl-5,6-dihydro-1,3-benzothiazol-7(4H)-one;
5,5-Dimethyl-2-{(3S)-3-[3-(1-naphthyl)benzyl]morpholin-4-yl}-5,6-dihydro-1,3-benzothiazol-7(4H)-one;
5,5-Dimethyl-2-{(3S)-3-[3-(2-naphthyl)benzyl]morpholin-4-yl}-5,6-dihydro-1,3-benzothiazol-7(4H)-one;
2-{(3S)-3-[(3'-Chlorobiphenyl-3-yl)methyl]morpholin-4-yl}-5,5-dimethyl-5,6-dihydro-1,3-benzothiazol-7(4H)-one;
5,5-Dimethyl-2-{(3S)-3-[(3'-fluorobiphenyl-3-yl)methyl]morpholin-4-yl}-5,6-dihydro-1,3-benzothiazol-7(4H)-one;
5,5-Dimethyl-2-{(3S)-3-[(2'-fluorobiphenyl-3-yl)methyl]morpholin-4-yl}-5,6-dihydro-1,3-benzothiazol-7(4H)-one;
2-{(3S)-3-[(2',6'-Difluorobiphenyl-3-yl)methyl]morpholin-4-yl}-5,5-dimethyl-5,6-dihydro-1,3-benzothiazol-7(4H)-one;
2-{(3S)-3-[(3',4'-Dichlorobiphenyl-3-yl)methyl]morpholin-4-yl}-5,5-dimethyl-5,6-dihydro-1,3-benzothiazol-7(4H)-one;
5,5-Dimethyl-2-[(3S)-3-{[4'-(methylthio)biphenyl-3-yl]methyl}morpholin-4-yl]-5,6-dihydro-1,3-benzothiazol-7(4H)-one;
2-[(3S)-3-[3-(1-Benzofuran-2-yl)benzyl]morpholin-4-yl]-5,5-dimethyl-5,6-dihydro-1,3-benzothiazol-7(4H)-one;
2-{(3S)-3-[3-(1-Benzothien-2-yl)benzyl]morpholin-4-yl}-5,5-dimethyl-5,6-dihydro-1,3-benzothiazol-7(4H)-one;
5,5-Dimethyl-2-{(3S)-3-[(3'-methylbiphenyl-3-yl)methyl]morpholin-4-yl}-5,6-dihydro-1,3-benzothiazol-7(4H)-one;
5,5-Dimethyl-2-{(3S)-3-[(2'-methoxybiphenyl-3-yl)methyl]morpholin-4-yl}-5,6-dihydro-1,3-benzothiazol-7(4H)-one;
5,5-Dimethyl-2-{(3S)-3-[3-(thien-2-yl)benzyl]morpholin-4-yl}-5,6-dihydro-1,3-benzothiazol-7(4H)-one;
5,5-Dimethyl-2-[(3S)-3-[(3'-ethoxybiphenyl-3-yl)methyl]morpholin-4-yl}-5,6-dihydro-1,3-benzothiazol-7(4H)-one;
5,5-Dimethyl-2-{(3S)-3-[3-(4-methylthien-2-yl)benzyl]morpholin-4-yl}-5,6-dihydro-1,3-benzothiazol-7(4H)-one;
2-{(3S)-3-[3-(5-Acetylthien-2-yl)benzyl]morpholin-4-yl}-5,5-dimethyl-5,6-dihydro-1,3-benzothiazol-7(4H)-one;
2-{(3S)-3-[3-(1-Benzothien-3-yl)benzyl]morpholin-4-yl}-5,5-dimethyl-5,6-dihydro-1,3-benzothiazol-7(4H)-one;
5,5-Dimethyl-2-{(3S)-3-[3(4'-methylbiphenyl-3-yl)methyl]morpholin-4-yl}-5,6-dihydro-1,3-benzothiazol-7(4H)-one;
2-{(3S)-3-[(3'-Acetylbiphenyl-3-yl)methyl]morpholin-4-yl}-5,5-dimethyl-5,6-dihydro-1,3-benzothiazol-7(4H)-one;
2-{(3S)-3-[(4'-Acetylbiphenyl-3-yl)methyl]morpholin-4-yl}-5,5-dimethyl-5,6-dihydro-1,3-benzothiazol-7(4H)-one;

2-{(3S)-3-[3(2'-Bromobiphenyl-3-yl]methyl)morpholin-4-yl}-5,5-dimethyl-5,6-dihydro-1,3-benzothiazol-7(4H)-one;
2-{(3S)-3-[(3'-Bromobiphenyl-3-yl)methyl]morpholin-4-yl}-5,5-dimethyl-5,6-dihydro-1,3-benzothiazol-7(4H)-one;
2-{(3S)-3-[(4'-Bromobiphenyl-3-yl)methyl]morpholin-4-yl}-5,5-dimethyl-5,6-dihydro-1,3-benzothiazol-7(4H)-one;
2-[(3S)-3-{[3',5'-Bis(trifluoromethyl)biphenyl-3-yl]methyl}morpholin-4-yl]-5,5-dimethyl-5,6-dihydro-1,3-benzothiazol-7(4H)-one;
2-{(3S)-3-[(4'-Chlorobiphenyl-3-yl)methyl]morpholin-4-yl}-5,5-dimethyl-5,6-dihydro-1,3-benzothiazol-7(4H)-one;
2-{(3S)-3-[(2',5'-Dichlorobiphenyl-3-yl)methyl]morpholin-4-yl}-5,5-dimethyl-5,6-dihydro-1,3-benzothiazol-7(4H)-one;
2-{(3S)-3-[(3',5'-Difluorobiphenyl-3-yl)methyl]morpholin-4-yl}-5,5-dimethyl-5,6-dihydro-1,3-benzothiazol-7(4H)-one;
2-{(3S)-3-[(3',4'-Dimethoxybiphenyl-3-yl)methyl]morpholin-4-yl}-5,5-dimethyl-5,6-dihydro-1,3-benzothiazol-7(4H)-one;
2-{(3S)-3-[(2',3'-Dimethylbiphenyl-3-yl)methyl]morpholin-4-yl}-5,5-dimethyl-5,6-dihydro-1,3-benzothiazol-7(4H)-one;
2-{(3S)-3-[(3',5'-Dimethylbiphenyl-3-yl)methyl]morpholin-4-yl}-5,5-dimethyl-5,6-dihydro-1,3-benzothiazol-7(4H)-one;
2-{(3S)-3-[(2',5'-Dimethylbiphenyl-3-yl)methyl]morpholin-4-yl}-5,5-dimethyl-5,6-dihydro-1,3-benzothiazol-7(4H)-one;
5,5-Dimethyl-2-{(3S)-3-[(4'-fluoro-3'-methylbiphenyl-3-yl)methyl]morpholin-4-yl}-5,6-dihydro-1,3-benzothiazol-7(4H)-one;
5,5-Dimethyl-2-{(3S)-3-[(4'-fluorobiphenyl-3-yl)methyl]morpholin-4-yl}-5,6-dihydro-1,3-benzothiazol-7(4H)-one;
5,5-Dimethyl-2-{(3S)-3-[(4'-methoxybiphenyl-3-yl)methyl]morpholin-4-yl}-5,6-dihydro-1,3-benzothiazol-7(4H)-one;
2-{(3S)-3-[3-(1,3-benzodioxol-5-yl)benzyl]morpholin-4-yl}-5,5-dimethyl-5,6-dihydro-1,3-benzothiazol-7(4H)-one;
5,5-Dimethyl-2-{(3S)-3-[4'-phenoxybiphenyl-3-yl)methyl]morpholin-4-yl}-5,6-dihydro-1,3-benzothiazol-7(4H)-one;
5,5-Dimethyl-2-[(3S)-3-{[3'-(trifluoromethyl)biphenyl-3-yl]methyl}morpholin-4-yl]-5,6-dihydro-1,3-benzothiazol-7(4H)-one;
2-{(3S)-3-[3',4'-Difluorobiphenyl-3-yl)methyl]morpholin-4-yl}-5,5-dimethyl-5,6-dihydro-1,3-benzothiazol-7(4H)-one;
N-(3'-{[(3S)-4-(5,5-Dimethyl-7-oxo-4,5,6,7-tetrahydro-1,3-benzothiazol-2-yl)morpholin-3-yl]methyl}biphenyl-3-yl)acetamide;
2-{(3S)-3-[(3'-Aminobiphenyl-3-yl)methyl]morpholin-4-yl}-5,5-dimethyl-5,6-dihydro-1,3-benzothiazol-7(4H)-one;
3'-{[(3S)-4-(5,5-Dimethyl-7-oxo-4,5,6,7-tetrahydro-1,3-benzothiazol-2-yl)morpholin-3-yl]methyl}biphenyl-4-carbonitrile;
5,5-Dimethyl-2-[(3S)-3-{[3'-(hydroxymethyl)biphenyl-3-yl]methyl}morpholin-4-yl]-5,6-dihydro-1,3-benzothiazol-7(4H)-one;
5,5-Dimethyl-2-[(3S)-3-{[2'-(hydroxymethyl)biphenyl-3-yl]methyl}morpholin-4-yl]-5,6-dihydro-1,3-benzothiazol-7(4H)-one;
5,5-Dimethyl-2-[(3S)-3-{[3'-(trifluoromethoxy)biphenyl-3-yl]methyl}morpholin-4-yl]-5,6-dihydro-1,3-benzothiazol-7(4H)-one;
5,5-Dimethyl-2-{(3S)-3-[3-(6-methoxypyridin-3-yl)benzyl]morpholin-4-yl}-5,6-dihydro-1,3-benzothiazol-7(4H)-one;
N-(3'-{[(3S)-4-(5,5-Dimethyl-7-oxo-4,5,6,7-tetrahydro-1,3-benzothiazol-2-yl)morpholin-3-yl]methyl}biphenyl-3-yl)methanesulfonamide;
2-{(3S)-3-[3-(3,5-Dimethylisoxazol-4-yl)benzyl]morpholin-4-yl}-5,5-dimethyl-5,6-dihydro-1,3-benzothiazol-7(4H)-one;
5,5-Dimethyl-2-[(3S)-3-{3-[1-(phenylsulfonyl)-1H-indol-3-yl]benzyl}morpholin-4-yl]-5,6-dihydro-1,3-benzothiazol-7(4H)-one;
2-{(3S)-3-[3-(6-Chloropyridin-3-yl)benzyl]morpholin-4-yl}-5,5-dimethyl-5,6-dihydro-1,3-benzothiazol-7(4H)-one;
3'-{[(3S)-4-(5,5-Dimethyl-7-oxo-4,5,6,7-tetrahydro-1,3-benzothiazol-2-yl)morpholin-3-yl]methyl}biphenyl-4-carboxamide;
5,5-dimethyl-2-{(3S)-3-[3-(3-fluoropyridin-4-yl)benzyl]morpholin-4-yl}-5,6-dihydro-1,3-benzothiazol-7(4H)-one;
2-{(3S)-3-[3-(1-Benzyl-1H-pyrazol-4-yl)benzyl]morpholin-4-yl}-5,5-dimethyl-5,6-dihydro-1,3-benzothiazol-7(4H)-one;
5,5-Dimethyl-2-{(3S)-3-[3-(1-methyl-1H-pyrazol-4-yl)benzyl]morpholin-4-yl}-5,6-dihydro-1,3-benzothiazol-7(4H)-one;
7,7-Dimethyl-2-(morpholin-4-yl)-4,6,7,8-tetrahydro-5H-[1,3]thiazolo[5,4-b]azepin-5-one;
2-[(3S)-3-{[5-(Benzyloxy)-1H-indol-3-yl]methyl}morpholin-4-yl]-5,5-dimethyl-5,6-dihydro-1,3-benzothiazol-7(4H)-one;
5,5-Dimethyl-2-[(3S)-3-{[5-(hydroxy)-1H-indol-3-yl]methyl}morpholin-4-yl]-5,6-dihydro-1,3-benzothiazol-7(4H)-one;
7,7-Dimethyl-2-{(3S)-3-[(5-hydroxy-1H-indol-3-yl)methyl]morpholin-4-yl}-5,6,7,8-tetrahydro-4H-[1,3]thiazolo[5,4-c]azepin-4-one;
3-{[(3S)-4-(5,5-Dimethyl-7-oxo-4,5,6,7-tetrahydro-1,3-benzothiazol-2-Amorpholin-3-yl]methyl}-1H-indol-5-yl methanesulfonate;
2-[3-(3,4-Dihydroisoquinolin-2(1H)-ylcarbonyl)morpholin-4-yl]-5,5-dimethyl-5,6-dihydro-1,3-benzothiazol-7(4H)-one;
2-[3-(3,4-Dihydroquinoxalin-1(2H)-ylcarbonyl)morpholin-4-yl]-5,5-dimethyl-5,6-dihydro-1,3-benzothiazol-7(4H)-one;
5,5-Dimethyl-2-{3-[(6-methyl-3,4-dihydroquinolin-1(2H)-yl)carbonyl]morpholin-4-yl}-5,6-dihydro-1,3-benzothiazol-7(4H)-one;
5,5-Dimethyl-2-{3-[(6-methoxy-3,4-dihydroquinolin-1(2H)-yl)carbonyl]morpholin-4-yl}-5,6-dihydro-1,3-benzothiazol-7(4H)-one;
5,5-Dimethyl-2-[(3S)-3-(3-phenylprop-2-yn-1-yl)morpholin-4-yl]-5,6-dihydro-1,3-benzothiazol-7(4H)-one;
2-[(3S)-3-(1H-Benzotriazol-1-ylmethyl)morpholin-4-yl]-5,5-dimethyl-5,6-dihydro-1,3-benzothiazol-7(4H)-one;
2-[(3S)-3-(1H-Benzimidazol-1-ylmethyl)morpholin-4-yl]-5,5-dimethyl-5,6-dihydro-1,3-benzothiazol-7(4H)-one;

2-[2-(Aminomethyl)morpholin-4-yl]-5,5-dimethyl-5,6-dihydro-1,3-benzothiazol-7(4H)-one;

N-(1-Benzothien-3-ylmethyl)-2-[4-(5,5-dimethyl-7-oxo-4,5,6,7-tetrahydro-1,3-benzothiazol-2-yl)morpholin-2-yl]acetamide;

N-{[4-(5,5-Dimethyl-7-oxo-4,5,6,7-tetrahydro-1,3-benzothiazol-2-yl)morpholin-2-yl]methyl}-1-benzofuran-2-carboxamide;

N-{[4-(5,5-Dimethyl-7-oxo-4,5,6,7-tetrahydro-1,3-benzothiazol-2-yl)morpholin-2-yl]methyl}benzenesulfonamide; or (7E)-5,5-Dimethyl-2-(morpholin-4-yl)-5,6-dihydro-1,3-benzothiazol-7(4H)-one hydrazone.

13. The pharmaceutical composition comprising a compound according to claim 2 and a pharmaceutically acceptable carrier.

14. The compound as claimed in claim 10 wherein $R^{43}$ represents hydrogen.

15. The pharmaceutical composition comprising a compound according to claim 3 and a pharmaceutically acceptable carrier.

16. The pharmaceutical composition comprising a compound according to claim 4 and a pharmaceutically acceptable carrier.

* * * * *